US008911729B2

(12) United States Patent
Lukacs et al.

(10) Patent No.: US 8,911,729 B2
(45) Date of Patent: Dec. 16, 2014

(54) STEM CELL FACTOR INHIBITOR

(75) Inventors: Nicholas W. Lukacs, Brighton, MI (US); Vladislav Dolgachev, Ann Arbor, MI (US); Steven L. Kunkel, Ann Arbor, MI (US); Cory M. Hogaboam, Ann Arbor, MI (US); Sem H. Phan, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/347,459

(22) Filed: Jan. 10, 2012

(65) Prior Publication Data

US 2012/0321629 A1 Dec. 20, 2012

Related U.S. Application Data

(60) Provisional application No. 61/431,246, filed on Jan. 10, 2011.

(51) Int. Cl.

| | |
|---|---|
| ***A61K 39/40*** | (2006.01) |
| ***A61K 39/395*** | (2006.01) |
| ***C07K 16/22*** | (2006.01) |
| ***C07K 16/24*** | (2006.01) |
| *A61K 39/00* | (2006.01) |

(52) U.S. Cl.

CPC ................ *C07K 16/24* (2013.01); *C07K 16/22* (2013.01); *C07K 2317/76* (2013.01); *A61K 2039/505* (2013.01)

USPC .................................... 424/139.1; 424/141.1

(58) Field of Classification Search

None

See application file for complete search history.

(56) References Cited

U.S. PATENT DOCUMENTS

| | | | | |
|---|---|---|---|---|
| 4,816,567 | A | 3/1989 | Cabilly et al. | |
| 4,946,778 | A | 8/1990 | Ladner | |
| 5,225,539 | A | 7/1993 | Winter | |
| 5,641,870 | A | 6/1997 | Rinderknecht | |
| 5,731,168 | A | 3/1998 | Carter | |
| 6,506,559 | B1 | 1/2003 | Fire | |
| 7,144,731 | B2 | 12/2006 | Zsebo et al. | |
| 7,285,640 | B2 * | 10/2007 | Takeuchi et al. | 530/387.1 |
| 7,582,297 | B2 * | 9/2009 | Reed | 424/141.1 |
| 7,893,036 | B2 | 2/2011 | Zamore | |
| 8,278,067 | B2 * | 10/2012 | Longley | 435/69.2 |
| 2003/0194405 | A1 | 10/2003 | Takeuchi et al. | |
| 2005/0112698 | A1 | 5/2005 | Neben | |
| 2007/0253951 | A1 | 11/2007 | Ng et al. | |
| 2008/0025958 | A1 | 1/2008 | Hannon | |
| 2008/0200420 | A1 | 8/2008 | Zamore | |
| 2008/0269147 | A1 | 10/2008 | Tuschl | |
| 2010/0305003 | A1 | 12/2010 | Tang | |

FOREIGN PATENT DOCUMENTS

| | | | |
|---|---|---|---|
| EP | 125023 | | 11/1984 |
| EP | 171496 | | 2/1986 |
| EP | 173494 | | 3/1986 |
| EP | 184187 | | 6/1986 |
| WO | 8601533 | | 3/1986 |
| WO | 8702671 | | 5/1987 |
| WO | 03070966 | A2 | 8/2003 |
| WO | 2005038054 | A1 | 4/2005 |
| WO | 2005054270 | | 6/2005 |
| WO | 2006066048 | | 6/2006 |
| WO | 2008006369 | | 1/2008 |
| WO | 2008043753 | | 4/2008 |
| WO | 2008051306 | | 5/2008 |

OTHER PUBLICATIONS

Powell et al., "Epithelial cells and their neighbors I. Role of intestinal myofibroblasts in development, repair, and cancer." Am J Physiol Gastrointest Liver Physiol. Jul. 2005; 289(1):G2-7.

Powell et al., "Myofibroblasts. II. Intestinal subepithelial myofibroblasts." Am J Physiol. Aug. 1999; 277(2 Pt 1):C183-201.

Remington's pharmaceutical sciences, 17th ed. Edited by Alfonso R. Gennaro. Mack Publishing Co., 20th and Northampton Streets, Easton, PA 18042. 1985.

S.P.C. Cole, D. Kozbor and J.C. Roder. "The EBV-hybridoma technique and its application to human lung cancer." In, Monoclonal Antibodies and Cancer Therapy (vol. 27, UCLA Symposia on Molecular and Cellular Biology, New Series) (eds. R.A. Reisfeld and S.Sell), pp. 77-96, Alan R. Liss, Inc. N.Y., 1985.

Sastry et al., "Cloning of the immunological repertoire in *Escherichia coli* for generation of monoclonal catalytic antibodies: construction of a heavy chain variable region-specific cDNA library." Proc Natl Acad Sci U S A. Aug. 1989; 86(15):5728-32.

Schubert et al., "Local RNA target structure influences siRNA efficacy: systematic analysis of intentionally designed binding regions." J Mol Biol. May 13, 2005;348(4):883-93.

Shalaby et al., "Development of humanized bispecific antibodies reactive with cytotoxic lymphocytes and tumor cells overexpressing the HER2 protooncogene." J Exp Med. Jan. 1, 1992;175(1):217-25.

Shaw et al., "Mouse/human chimeric antibodies to a tumor-associated antigen: biologic activity of the four human IgG subclasses." J Natl Cancer Inst. Dec. 7, 1988;80(19):1553-9.

Sohail et al., "Antisense oligonucleotides selected by hybridisation to scanning arrays are effective reagents in vivo." Nucleic Acids Res. May 15, 2001;29(10):2041-51.

Stumpp & Amstutz, "DARPins: a true alternative to antibodies." Curr Opin Drug Discov Devel. Mar. 2007;10(2):153-9.

Sun et al., "Chimeric antibody with human constant regions and mouse variable regions directed against carcinoma-associated antigen 17-1A."Proc Natl Acad Sci U S A. Jan. 1987;84(1):214-8.

Suresh et al., "Bispecific monoclonal antibodies from hybrid hybridomas." Methods Enzymol. 1986;121:210-28.

Traunecker et al., "Bispecific single chain molecules (Janusins) target cytotoxic lymphocytes on HIV infected cells." EMBO J. Dec. 1991;10(12):3655-9.

Tuschl & Borkhardt, "Small interfering RNAs: a revolutionary tool for the analysis of gene function and gene therapy." Mol Interv. Jun. 2002;2(3):158-67.

(Continued)

*Primary Examiner* — Michail Belyavskyi

(74) *Attorney, Agent, or Firm* — Thomas A. Isenbarger; Casimir Jones, S.C.

(57) ABSTRACT

Provided herein are methods, compositions, and uses relating to inhibitors of stem cell factor. For example, provided herein are antibodies targeting stem cell factor and methods for treating fibrotic and tissue remodeling diseases.

39 Claims, 7 Drawing Sheets

(56) References Cited

OTHER PUBLICATIONS

Tuschl et al., "Targeted mRNA degradation by double-stranded RNA in vitro." Genes Dev. Dec. 15, 1999;13(24):3191-7.

Verhoeyen et al., "Reshaping human antibodies: grafting an antilysozyme activity" Science Mar. 25, 1988:1534-1536.

Vittal et al., "Effects of the protein kinase inhibitor, imatinib mesylate, on epithelial/mesenchymal phenotypes: implications for treatment of fibrotic diseases." J Pharmacol Exp Ther. Apr. 2007; 321(1):35-44.

Vuorinen et al., "Imatinib mesylate inhibits fibrogenesis in asbestos-induced interstitial pneumonia." Exp Lung Res. Sep. 2007;33(7):357-73.

Williams et al., "Identification of a ligand for the c-kit proto-oncogene." Cell. Oct. 5, 1990; 63(1):167-74.

Wood et al., "The synthesis and in vivo assembly of functional antibodies in yeast." Nature. Apr. 4-10, 1985;314(6010):446-9.

Zapata et al., "Engineering linear F(ab')2 fragments for efficient production in *Escherichia coli* and enhanced antiproliferative activity."Protein Eng. Oct. 1995;8(10):1057-62.

Zsebo et al., "Identification, purification, and biological characterization of hematopoietic stem cell factor from buffalo rat liver—conditioned medium." Cell. Oct. 5, 1990; 63(1):195-201.

Andre et al., "c-kit mRNA expression in human and murine hematopoietic cell lines." Oncogene. Aug. 1989; 4(8):1047-9.

Aono et al., "Imatinib as a novel antifibrotic agent in bleomycin-induced pulmonary fibrosis in mice." Am J Respir Crit Care Med. Jun. 1, 2005; 171(11):1279-85.

Beidler et al., "Cloning and high level expression of a chimeric antibody with specificity for human carcinoembryonic antigen." J Immunol. Dec. 1, 1988; 141(11):4053-60.

Berlin et al., "Inhibition of SCF attenuates peribronchial remodeling in chronic cockroach allergen-induced asthma." Lab Invest. Jun. 2006;86(6):557-65.

Better et al., "*Escherichia coli* secretion of an active chimeric antibody fragment." nce. May 20, 1988; 240 (4855):1041-3.

Bohula et al., "The efficacy of small interfering RNAs targeted to the type 1 insulin-like growth factor receptor (IGF1R) is influenced by secondary structure in the IGF1R transcript." J Biol Chem. May 2, 2003;278(18):15991-7.

Brennan et al., "Preparation of bispecific antibodies by chemical recombination of monoclonal immunoglobulin G1 fragments." Science. Jul. 5, 1985;229(4708):81-3.

Brummelkamp et al., "A system for stable expression of short interfering RNAs in mammalian cells." Science. Apr. 19, 2002;296(5567):550-3.

Caplen et al., "Specific inhibition of gene expression by small double-stranded RNAs in invertebrate and vertebrate systems." Proc Natl Acad Sci U S A. Aug. 14, 2001;98(17):9742-7.

Clackson et al., "Making antibody fragments using phage display libraries." Nature. Aug. 15, 1991; 352(6336):624-8.

Coloma et al., "Primer design for the cloning of immunoglobulin heavy-chain leader-variable regions from mouse hybridoma cells using the PCR." Biotechniques. Aug. 1991;11(2):152-4, 156.

Distler et al., "Imatinib mesylate reduces production of extracellular matrix and prevents development of experimental dermal fibrosis." Arthritis Rheum. Jan. 2007; 56(1):311-22.

Dolgachev et al., "Role of Stem Cell factor and bone marrow-derived fibroblasts in airway remodeling." Am. J. Pathol 2009, 174(2):390-400.

El Kossi et al., "Stem cell factor and crescentic glomerulonephritis." Am J Kidney Dis. Apr. 2003; 41(4):785-95.

Elbashir et al., "Duplexes of 21-nucleotide RNAs mediate RNA interference in cultured mammalian cells." Nature. May 24, 2001;411(6836):494-8.

Elbashir et al., "Functional anatomy of siRNAs for mediating efficient RNAi in *Drosophila melanogaster* embryo lysate." EMBO J. Dec. 3, 2001;20(23):6877-88.

Elbashir et al., "RNA interference is mediated by 21- and 22-nucleotide RNAs." Genes Dev. Jan. 15, 2001;15(2):188-200.

El-Koraie et al., "Role of stem cell factor and mast cells in the progression of chronic glomerulonephritides." Kidney Int. Jul. 2001; 60(1):167-72.

GenBank Accession No. NG_012098, Homo sapiens KIT ligand (KITLG), RefSeqGene on chromosome 12.

GenBank Accession No. NM_000899, *Homo sapiens* KIT ligand (KITLG), transcript variant b, Mrna.

GenBank Accession No. NM_003994, *Homo sapiens* KIT ligand (KITLG), transcript variant a, Mrna.

GenBank Accession No. NP_000890, kit ligand isoform b precursor [*Homo sapiens*].

GenBank Accession No. NP_003985, kit ligand isoform a precursor [*Homo sapiens*].

GenBank Direct Submission. B61190 titled "mast cell growth factor, short form precursor-human" (PRI Jul. 21, 2000) <http://www.ncbi.nlm.nih.gov/protein/B61190?report=genpept./.

Goding, Monoclonal Antibodies: Principles and Practice, Academic Press, 1986.

Gruber et al., "Efficient tumor cell lysis mediated by a bispecific single chain antibody expressed in *Escherichia coli*." J Immunol. Jun. 1, 1994;152(11):5368-74.

Harlow & Lane, "Antibodies: A Laboratory Manual" Copld Spring Harbor Laboratory Press, Cold Spring Harbor, NY, 1988.

Holen et al., "Positional effects of short interfering RNAs targeting the human coagulation trigger Tissue Factor." Nucleic Acids Res. Apr. 15, 2002;30(8):1757-66.

Huang et al., "The hematopoietic growth factor KL is encoded by the SI locus and is the ligand of the c-kit receptor, the gene product of the W locus." Cell. Oct. 5, 1990;63(1):225-33.

Huse et al., "Generation of a large combinatorial library of the immunoglobulin repertoire in phage lambda." Science. Dec. 8, 1989;246(4935):1275-81.

Jones et al., "Replacing the complementarity-determining regions in a human antibody with those from a mouse." Nature. May 29-Jun 4, 1986; 321(6069):522-5.

Kohler et al., "Continuous cultures of fused cells secreting antibody of predefined specificity." Nature. Aug. 7, 1975;256(5517):495-7.

Kostelny et al., "Formation of a bispecific antibody by the use of leucine zippers." J Immunol. Mar. 1, 1992;148(5):1547-53.

Kozbor et al., "The Production of Monoclonal Antibodies from Human lymphocytes." Immunology Today. 1983, 4:72-79.

Kretschmer-Kazemi & Sczakiel, "The activity of siRNA in mammalian cells is related to structural target accessibility: a comparison with antisense oligonucleotides." Nucleic Acids Res. Aug. 1, 2003;31(15):4417-24.

Larrick et al., :PCR Amplification of Antibody Genes. Methods: Companion to Methods in Enzymology 1991, 2:106.

Liu et al., "Chimeric mouse-human IgG1 antibody that can mediate lysis of cancer cells." Proc Natl Acad Sci U S A. May 1987;84(10):3439-43.

Liu et al., "Production of a mouse-human chimeric monoclonal antibody to CD20 with potent Fc-dependent biologic activity." J Immunol. Nov. 15, 1987;139(10):3521-6.

Marks et al., "By-passing immunization. Human antibodies from V-gene libraries displayed on phage." J Mol Biol. Dec. 5, 1991;222(3):581-97.

Martin et al., "Primary structure and functional expression of rat and human stem cell factor DNAs." Cell. Oct. 5, 1990; 63(1):203-11.

McCafferty et al., "Phage antibodies: filamentous phage displaying antibody variable domains."Nature. Dec. 6, 1990; 348(6301):552-4.

Milstein et al., "Hybrid hybridomas and their use in immunohistochemistry." Nature. Oct 6-12, 1983;305(5934):537-40.

Morimoto et al., "Single-step purification of F(ab')2 fragments of mouse monoclonal antibodies (immunoglobulins G1) by hydrophobic interaction high performance liquid chromatography using TSKgel Phenyl-5PW." vol. 24, Issues 1-2, 1992, pp. 107-117.

Morrison, "Transfectomas provide novel chimeric antibodies." Science. Sep. 20, 1985;229(4719):1202-7.

(56) References Cited

OTHER PUBLICATIONS

Nishimura et al., "Recombinant human-mouse chimeric monoclonal antibody specific for common acute lymphocytic leukemia antigen." Cancer Res. Feb. 15, 1987;47(4):999-1005.
Oi et al., "Chimeric Antibodies." BioTechniques 1986, 4:214.
Orlandi et al., "Cloning immunoglobulin variable domains for expression by the polymerase chain reaction." Proc Natl Acad Sci U S A. May 1989;86(10):3833-7.
Orr-Urtreger et al., "Developmental expression of c-kit, a proto-oncogene encoded by the W locus." Development. Aug. 1990; 109(4):911-23.
Overhoff et al., "Local RNA target structure influences siRNA efficacy: a systematic global analysis." J Mol Biol. May 13, 2005;348(4):871-81.
Pluckthun, "Antibodies from *Escherichia coli*." in the Phamacology of Monoclonal Antibodies, M. Rosenberg and G.P. Moore Eds., (Springer Verlag, Berlin 1994), 113:269-315.

* cited by examiner

The amino acid sequence of an immunogenic peptide used to produce antibodies specific for SCF (SEQ ID NO: 1)

Ser Ser Ser Asn Arg Lys Ala Lys Asn Pro Pro Gly Asp Ser Cys

The nucleotide sequence corresponding to the amino acid sequence of SEQ ID NO: 1 (SEQ ID NO: 2)

TCG TCG TCG AAC CGC AAA GCG AAA AAC CCG CCG GGC GAT TCG TGC

Ser Ser Ser Asn Arg Lys Ala Lys Asn Pro Pro Gly Asp Ser Cys

STEM CELL FACTOR INHIBITOR

This application claims priority to U.S. Patent Application Ser. No. 61/431,246 filed on Jan. 10, 2011, which is incorporated herein by reference in its entirety for all purposes.

STATEMENT REGARDING FEDERALLY SPONSORED RESEARCH OR DEVELOPMENT

This invention was made with government support under HL059178 awarded by the National Institutes of Health. The government has certain rights in the invention.

FIELD OF INVENTION

Provided herein are methods, compositions, and uses relating to inhibitors of stem cell factor. For example, provided herein are antibodies targeting stem cell factor and methods for treating fibrotic and tissue remodeling diseases.

BACKGROUND

Diseases involving tissue remodeling and fibrosis are a leading cause of death worldwide. Nearly 45 percent of all natural deaths in the western world are attributable to some type of chronic fibroproliferative disease and the associated health care costs are in the billions of dollars. Tissue remodeling is the reorganization or renovation of existing tissues, which can either change the characteristics of a tissue (e.g., blood vessel remodeling) or participate in establishing the dynamic equilibrium of a tissue (e.g., bone remodeling). Fibrosis is the formation or development of excess fibrous connective tissue in an organ or tissue as a reparative or reactive process, as opposed to formation of fibrous tissue as a normal constituent of an organ or tissue. Fibrosis affects nearly all tissues and organ systems, and fibrotic tissue remodeling can influence cancer metastasis and accelerate chronic graft rejection in transplant recipients. Diseases in which fibrosis is a major cause of morbidity and mortality include the interstitial lung diseases, liver cirrhosis, kidney disease, heart disease, and systemic sclerosis, among others.

Stem cell factor (SCF) and its receptor c-Kit have been implicated in fibrotic and tissue remodeling diseases (El-Koraie, et al., Kidney Int. 60: 167 (2001); Powell, et al., Am. J. Physiol. 289: G2 (2005); El Kossi, et al., Am. J. Kidney Dis. 41: 785 (2003); Powell, et al., Am. J. Physiol. 277: C183 (1999)). c-Kit is a type III receptor-tyrosine kinase that is present in many cell types (Orr-Urtreger et al., Development 109: 911 (1990)). It is also expressed in the early stages of differentiation (Andre et al., Oncogene 4: 1047 (1989)) and certain tumors exhibit elevated expression of c-kit. SCF is a ligand specific for the c-Kit receptor kinase. Binding causes dimerization of c-Kit and activation of its kinase activity. SCF was first isolated from the supernatant of murine fibroblasts. At the time, SCF was called mast cell growth factor (MGF) (Williams et al., Cell 63: 167 (1990)) or hematopoietic growth factor KL (Kit ligand) (Huang et al., Cell 63: 225 (1990)). A homologue was subsequently isolated from rat liver cells and designated stem cell factor (SCF) (Zsebo et al., Cell 63: 195 (1990)). The corresponding human protein is designated variously as SCF, MGF, or Steel Factor (SF) (Cell 63: 203 (1990)).

Previous studies have suggested that an inhibitor of c-Kit receptor tyrosine kinase can significantly inhibit aberrant tissue fibrosis (see, e.g., Aono, Am. J. Respir. Crit. Care Med. 171: 1279 (2005); Vuorinen, et al., Exp. Lung Res. 33: 357 (2007); Vittal, et al., J. Pharmacol. Exp. Ther. 321:35 (2007); Distler, et al., Arthritis Rheum 56: 311 (2007)). However, this inhibitor has several disadvantages. It needs to be given systemically by oral administration, it has some toxicity associated with its use, and the compound must be delivered intracellularly for efficacy. Consequently, alternative therapies are needed.

SUMMARY

Provided herein are methods, compositions, and uses relating to inhibitors of stem cell factor. For example, provided herein are antibodies targeting stem cell factor and methods for treating fibrotic and tissue remodeling diseases as well as for research and diagnostic uses.

In some embodiments, the compositions, methods, and uses herein provide therapies relating to inhibiting stem cell factor (SCF). Some embodiments provide an isolated antibody that targets SCF. In some embodiments, inhibiting SCF affects the activity of c-Kit. The compositions, methods, and uses provided herein find use in treating fibrotic diseases and maladies associated with tissue remodeling. Unlike some other therapies that produce undesirable side effects due to interfering with general intracellular signaling pathways, the embodiments provided herein eliminate or minimize such side effects by modulating the activity of SCF. Consequently, toxicity is minimized. Moreover, targeting an extracellular ligand removes the need to deliver a composition into a cell to interact with an intracellular target. In some embodiments, the compositions are delivered into the airway, thus providing an advantage over previous technologies that require oral administration and, as such, resulting in systemic bioavailability.

Provided herein are embodiments of methods for treating a fibrotic or tissue remodeling disease comprising administering a therapeutically effective amount of a stem cell factor inhibitor to a subject with or at risk for a fibrotic or tissue remodeling disease. For example, in some embodiments, provided herein are methods comprising providing an inhibitor of stem cell factor and administering a therapeutically effective amount of the inhibitor to a subject. In some embodiments the inhibitor is an isolated antibody (e.g., a monoclonal or polyclonal antibody) or an antigen-binding fragment thereof (e.g., Fab, Fab', $F(ab')_2$, and Fv fragments, etc.). In some embodiments the inhibitor is a small interfering RNA. In more specific embodiments, the antibody is a monoclonal antibody or a polyclonal antibody. Some embodiments provide that the antibody or antigen-binding fragment thereof specifically binds to stem cell factor. Some embodiments provide that the antibody or antigen-binding fragment thereof specifically binds to a peptide comprising amino acid sequence SEQ ID NO: 1 or SEQ ID NO: 8.

In some embodiments of the methods provided herein, the subject has a disease. Accordingly, some embodiments provide that administering the inhibitor prevents or reduces the severity of at least one sign or symptom of the disease. In some embodiments, the subject has an abnormal activity of stem cell factor or the subject has abnormal collagen production. In some embodiments, the subject has a disease including, but not limited to, fibrosis or a remodeling disease. In additional embodiments, the disease is a pulmonary disease. Some embodiments provide that a subject has a pulmonary disease including, but not limited to, idiopathic pulmonary fibrosis, chronic obstructive pulmonary disease, acute respiratory distress syndrome, cystic fibrosis, peribronchial fibrosis, hypersensitivity pneumonitis, or asthma. In addition, some embodiments provide that a subject has a disease including, but not limited to, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, or radiation-induced fibrosis.

While not limited in the mode of administration, in some embodiments of the method, the antibody is delivered into an airway of the subject, e.g., by intranasal administration.

In some embodiments, administering the inhibitor reduces the activity of a receptor. Some embodiments provide that administering the inhibitor reduces an interaction of stem cell factor with a receptor. In more specific embodiments, the receptor is a receptor tyrosine kinase, and in yet more specific embodiments, the receptor is c-Kit. Importantly, the methods are not limited in the location of the targeted receptor or the origin of stem cell factor. For example, in some embodiments the receptor is found on a hematopoietic progenitor cell, a melanocyte, a germ cell, an eosinophil, a lymphocyte, a fibroblast, a myofibroblast, or a mast cell. Additionally, in some embodiments, stem cell factor originates from a bone marrow cell, a liver cell, an epithelial cell, a smooth muscle cell, or a fibroblast. In some embodiments, administering the inhibitor to a subject results in a direct inhibition of fibroblast activation.

Some embodiments provide a composition comprising an isolated antibody (e.g., a monoclonal or a polyclonal antibody) or antigen-binding fragment thereof that specifically binds to stem cell factor (e.g., a protein or a peptide fragment thereof (e.g., an epitope)). For example, some embodiments provide a composition comprising an isolated antibody or antigen-binding fragment thereof that specifically binds to a peptide of amino acid sequence SEQ ID NO: 1 or SEQ ID NO: 8. Additional embodiments provide an antibody or antigen-binding fragment than binds to the SCF isoform b precursor (e.g., a protein or peptide fragment of the sequence available at GenBank accession number NP_000890 (SEQ ID NO: 4)), or a variant or modified form thereof, or to the SCF isoform a precursor (e.g., a protein or peptide fragment of the sequence available at GenBank accession number NP_003985 (SEQ ID NO: 6)), or a variant or modified form thereof. Some embodiments provide an antibody or antigen-binding fragment that binds to a protein or peptide, or variants or modified forms thereof, that is a translation product of the NCBI Reference Gene Sequence for SCF (e.g., accession number NG_012098 (SEQ ID NO: 7)) or variants or fragments thereof. Some embodiments provide an antibody or antigen-binding fragment that binds to a peptide comprising the first 11 amino acids of the mature form of SCF (e.g., EGICRNRVTNN (SEQ ID NO: 8)).

Some embodiments provide an antibody or antigen-binding fragment than binds to the translation product (e.g., a protein or peptide), or a variant or modified form thereof, of a nucleic acid encoding SCF, or a variant or a modified form thereof. For example, embodiments provide an antibody or antigen-binding fragment than binds to the translation product (e.g., a protein or peptide), or a variant or modified form thereof, of the nucleic acids having sequences comprising a sequence as defined by GenBank accession numbers NM_000899 (SEQ ID NO: 3), NM_003994 (SEQ ID NO: 5), and NG_012098 (SEQ ID NO: 7), or fragments or variants thereof (e.g., mutants, cDNAs, expression-optimized variants, operably linked to a regulatory element (e.g., promoter, enhancer, polymerase binding site, etc.), etc.). In some embodiments, the antibody or antigen-binding fragment binds to a protein or peptide, or a variant or modified form thereof, that is the translation product of a nucleotide sequence that encodes the peptide sequence EGICRNRVTNN (SEQ ID NO: 8). The peptides and proteins (and fragments and variants thereof) and the nucleic acids (and fragments and variants thereof) that encode the peptides and proteins (and fragments and variants thereof) are used in some embodiments to raise antibodies. Also contemplated are vectors, plasmids, expression constructs, cells, cell lines, hybridomas, and organisms used to produce the antibodies as provided herein.

Some embodiments provide a monoclonal antibody and some embodiments provide a humanized antibody. In some embodiments, the composition is used for a medicament or is used for the manufacture of a medicament. In some embodiments, the medicament is used to treat disease. Use of the composition as a medicament is not limited in the disease that can be treated. For example, in some embodiments, the disease is idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, or radiation-induced fibrosis. In some embodiments, the composition is used to study disease in vitro or in a model system (e.g., in vivo).

Embodiments provide herein a method of preparing an antibody (e.g., a monoclonal antibody) targeting stem cell factor comprising the steps of providing a peptide comprising or consisting of an immunogenic portion of SCF (e.g., as provided by SEQ ID NO: 1 or 8), immunizing a host with the peptide, isolating an immune cell from the host, preparing a hybridoma using the immune cell, and isolating the antibody or antigen-binding fragment thereof. Some embodiments provide a method of preparing an antibody (e.g., a monoclonal antibody) targeting stem cell factor, wherein the antibody or antigen-binding fragment thereof specifically binds to stem cell factor (e.g., a protein or a peptide fragment thereof (e.g., an epitope)). For example, some embodiments provide a method of preparing an isolated antibody or antigen-binding fragment thereof that specifically binds to a peptide of amino acid sequence SEQ ID NO: 1. Additional embodiments provide a method of preparing an antibody or antigen-binding fragment than binds to the SCF isoform b precursor (e.g., a protein or peptide fragment of the sequence available at GenBank accession number NP_000890 (SEQ ID NO: 4)), or a variant or modified form thereof, or to the SCF isoform a precursor (e.g., a protein or peptide fragment of the sequence available at GenBank accession number NP_003985 (SEQ ID NO: 6)), or a variant or modified form thereof. Some embodiments provide a method of preparing an antibody or antigen-binding fragment that binds to a protein or peptide, or variants or modified forms thereof, that is a translation product of the NCBI Reference Gene Sequence for SCF (e.g., accession number NG_012098 (SEQ ID NO: 7)) or variants or fragments thereof. Some embodiments provide a method of preparing an antibody or antigen-binding fragment that binds to a peptide comprising the first 11 amino acids of the mature form of SCF (e.g., EGICRNRVTNN (SEQ ID NO: 8)).

Some embodiments provide a method of preparing an antibody or antigen-binding fragment than binds to the translation product (e.g., a protein or peptide), or a variant or modified form thereof, of a nucleic acid encoding SCF, or a variant or a modified form thereof. For example, embodiments provide a method of preparing an antibody or antigen-binding fragment than binds to the translation product (e.g., a protein or peptide), or a variant or modified form thereof, of the nucleic acids having sequences comprising a sequence as defined by GenBank accession numbers NM_000899 (SEQ ID NO: 3), NM_003994 (SEQ ID NO: 5), and NG_012098 (SEQ ID NO: 7), or fragments or variants thereof (e.g., mutants, cDNAs, expression-optimized variants, operably linked to a regulatory element (e.g., promoter, enhancer, polymerase binding site, etc.), etc.). In some embodiments, the antibody or antigen-binding fragment binds to a protein or peptide, or a variant or modified form thereof, that is the translation product of a nucleotide sequence that encodes the peptide sequence EGICRNRVTNN (SEQ ID NO: 8). The peptides, proteins, and fragments and variants thereof; and nucleic acids, and fragments and variants thereof, that encode the peptides, proteins, and fragments and variants thereof, find use in some embodiments in a method of preparing antibodies as provided by the technology provided. Also contemplated are methods of producing vectors, plasmids, expression constructs, cells, cell lines, hybridomas, and organisms that find use in producing the antibodies as provided herein.

Some embodiments provide a method comprising the steps of providing an inhibitor of stem cell factor and administering the inhibitor to a cell or tissue.

In addition, some embodiments provide a kit comprising a composition comprising an isolated antibody or antigen-binding fragment thereof that specifically binds to stem cell factor, a means for administering the composition to a subject, and/or instructions for use.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A shows a plot demonstrating that an anti-SCF antibody reduces the amount of hydroxyproline in bleomycin treated lung; FIG. 1B shows a plot demonstrating that an anti-SCF antibody reduces the amount of IL-25 mRNA; FIG. 1C shows a plot demonstrating that an anti-SCF antibody reduces the amount of IL-13 mRNA; FIG. 1D shows a plot demonstrating that an anti-SCF antibody reduces the amount of soluble SCF present in plasma. FIG. 1E shows a plot demonstrating that an anti-SCF antibody reduces the amount of IL-25 receptor.

FIG. 3 shows an amino acid sequence and the corresponding nucleotide sequence of an immunogenic peptide used to produce antibodies specific for SCF.

DETAILED DESCRIPTION

Figure 1:
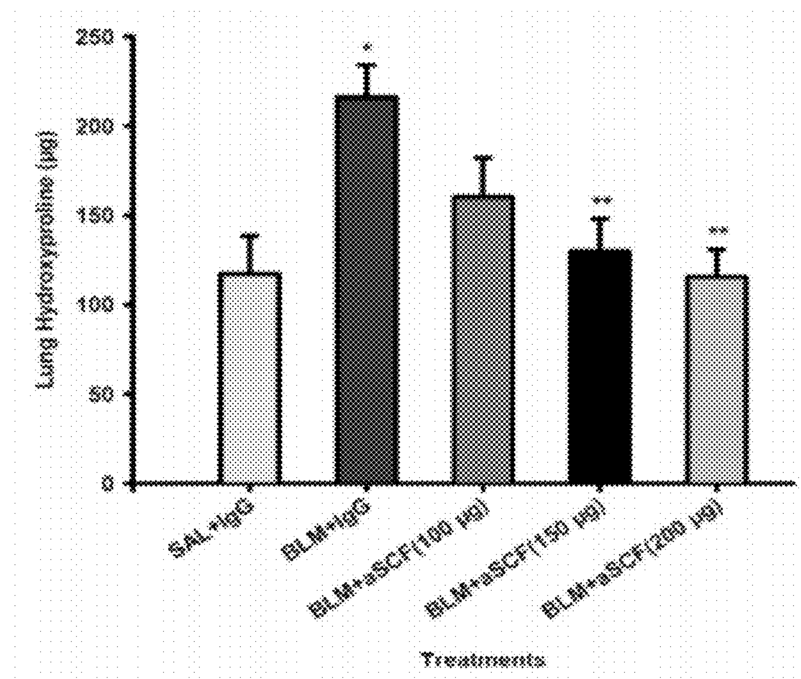
FIG. 1 shows a series of plots demonstrating that inhibiting SCF with an antibody reduces the expression of tissue remodeling mediators.
Figure 1:
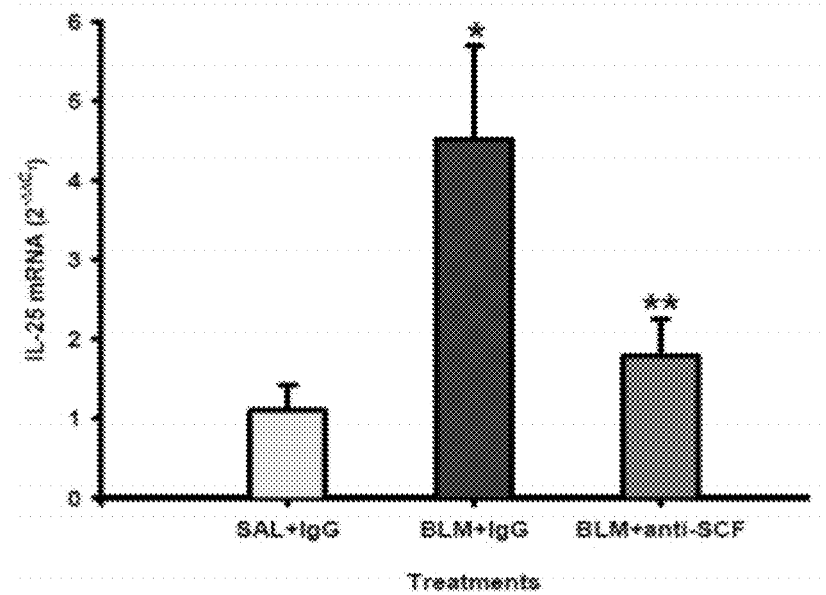
Figure 1:
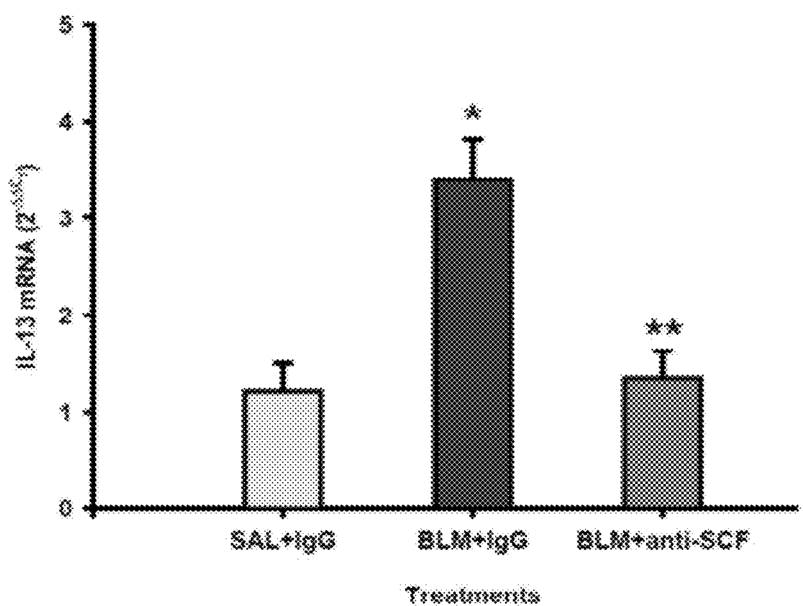
Figure 1:
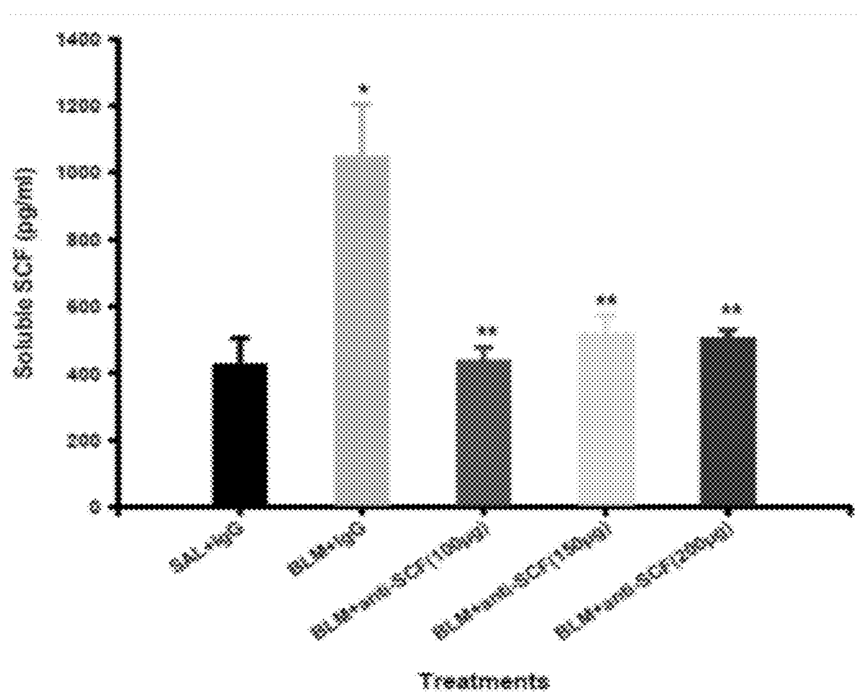
Figure 1:
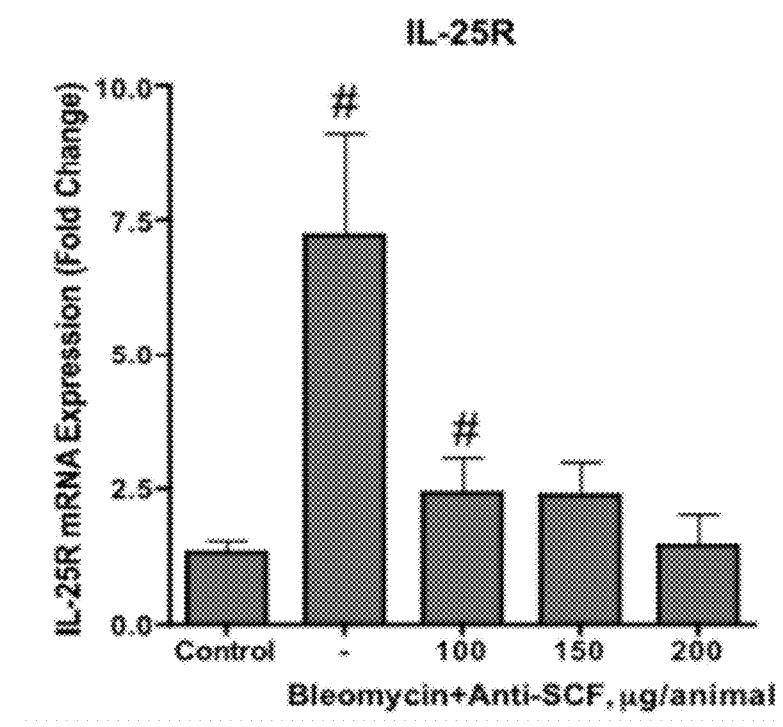

Provided herein are methods, compositions, and uses relating to inhibitors of stem cell factor. For example, provided herein are antibodies targeting stem cell factor, methods of producing antibodies targeting stem cell factor, and methods for treating fibrotic and tissue remodeling diseases as well as for research and diagnostic uses. In some embodiments, the compositions, methods, and uses herein provide therapies relating to inhibiting stem cell factor (SCF). Some embodiments provide an isolated antibody that targets SCF. In some embodiments, inhibiting SCF affects the activity of c-Kit. The compositions, methods, and uses provided herein find use in treating fibrotic diseases and maladies associated with tissue remodeling.

Definitions

To facilitate an understanding of embodiments of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "nascent" when used in reference to a protein refers to a newly synthesized protein, which has not been subject to post-translational modifications, which includes but is not limited to glycosylation and polypeptide shortening. The term "mature" when used in reference to a protein refers to a protein which has been subject to post-translational processing and/or which is in a cellular location (such as within a membrane or a multi-molecular complex) from which it can perform a particular function which it could not if it were not in the location.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include the transmembrane domains, and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "allele" refers to different variations in a gene; the variations include but are not limited to variants and mutants, polymorphic loci and single nucleotide polymorphic loci, frameshift and splice mutations. An allele may occur naturally in a population, or it might arise during the lifetime of any particular individual of the population.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences or fragments thereof may be employed as hybridization probes. In some embodiments, polynucleotide sequences are employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F' $(ab)_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', $F(ab)_2$, and Fv fragments; diabodies; linear antibodies (Zapata et al., Protein Eng. 8(10): 1057-1062 (1995)); single-chain antibody molecules; and multispecific antibodies formed from antibody fragments.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, "inhibitor" refers to a molecule which eliminates, minimizes, or decreases the activity, e.g., the biological, enzymatic, chemical, or immunological activity, of a target.

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, inflammation, etc.).

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive vs. conventional treatment).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "pharmaceutical composition" refers to the combination of an active agent with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject.

As used herein, "carriers" include pharmaceutically acceptable carriers, excipients, or stabilizers which are nontoxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "patient" or "subject" refer to organisms to be treated by the compositions of the present technology or to be subject to various tests provided by the technology. The term "subject" includes animals, preferably mammals, including humans. In a preferred embodiment, the subject is a primate. In an even more preferred embodiment, the subject is a human.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

Embodiments of the Technology

Although the disclosure herein refers to certain illustrated embodiments, it is to be understood that these embodiments are presented by way of example and not by way of limitation.

1. Inhibitors of SCF

Stem cell factor (SCF) is a ligand that is specific for the c-Kit receptor kinase. Binding of SCF to c-Kit causes dimerization of c-Kit and activation of its kinase activity, which is important for hemopoiesis, melanogenesis, and fertility. Through c-Kit, SCF acts to promote cell survival, proliferation, differentiation, adhesion, and functional activation. Aberrant activation of c-Kit can result in disease, including fibrosis and tissue remodeling defects. In particular, there are multiple pulmonary diseases with known remodeling defects as well as other chronic tissue remodeling diseases affecting other organs and tissues. Specific examples of diseases involving fibrosis or tissue remodeling defects are idiopathic pulmonary fibrosis, chronic obstructive pulmonary disease, acute respiratory distress syndrome, cystic fibrosis, peribronchial fibrosis, hypersensitivity pneumonitis, asthma, scleroderma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Accordingly, interfering with the interaction between SCF and c-Kit can be used to treat or study diseases involving aberrant activation of c-Kit that causes fibrosis and tissue remodeling defects. The c-Kit receptor is found on hematopoietic progenitor cells, melanocytes, germ cells, eosinophils, lymphocytes, and mast cells. Thus, preventing SCF interaction with c-Kit can alter the activation of several disease-associated cell populations that have been implicated in fibrosis and tissue remodeling disease phenotypes.

Additionally, SCF induces key mediators in the fibrotic response, IL-25 and IL-13. Data suggest that IL-25 can drive IL-13 expression in a T-cell and antigen-independent manner. Therefore, these processes can progress without an antigen-specific response and consequently chronically perpetuate remodeling and fibrotic disease. It is contemplated that a complex cascade is established in which SCF induces IL-25, which in turn induces production of IL-13, myofibroblast differentiation, and collagen production. IL-4 has also been identified as a fibrosis-associated cytokine.

2. Antibodies

In some embodiments, inhibiting the ability of SCF to interact with c-Kit is accomplished by means of an antibody that recognizes SCF. The antibody can be a monoclonal antibody or a polyclonal antibody, and may be, for example, a human, humanized, or chimeric antibody. Monoclonal antibodies against target antigens are produced by a variety of techniques including conventional monoclonal antibody methodologies such as the somatic cell hybridization techniques of Köhler and Milstein (Nature, 256:495 (1975)). Although in some embodiments, somatic cell hybridization procedures are preferred, other techniques for producing monoclonal antibodies are contemplated as well (e.g., viral or oncogenic transformation of B lymphocytes).

It is contemplated that antibodies against SCF find use in the experimental, diagnostic, and therapeutic methods described herein. In certain embodiments, the antibodies provided herein are used to detect the expression of SCF in biological samples. For example, a sample comprising a tissue biopsy can be sectioned and protein detected using, for example, immunofluorescence or immunohistochemistry. Alternatively, individual cells from a sample can be isolated, and protein expression detected on fixed or live cells by FACS analysis. Furthermore, the antibodies can be used on protein arrays to detect expression of SCF. In other embodiments, the antibodies provided herein are used to decrease the activity of cells expressing c-Kit by inhibiting SCF either in an in vitro cell-based assay or in an in vivo animal model. In some embodiments, antibodies are used to treat a human patient by administering a therapeutically effective amount of an antibody against SCF.

For the production of antibodies, various host animals can be immunized by injection with the peptide corresponding to the desired epitope (e.g., a fragment of SCF, e.g., a fragment comprising the sequence provided by SEQ ID NO: 1 or 8 or immunogenic portions thereof) including, but not limited to, rabbits, mice, rats, sheep, goats, etc. Antibodies to SCF can be raised by immunizing (e.g., by injection) with an antigen comprising a peptide, a portion, or the full protein of the SCF isoform b precursor (e.g., a protein or peptide fragment of the sequence available at GenBank accession number NP_000890 (SEQ ID NO: 4)), or a variant or modified version thereof, or a peptide, a portion, or the full protein of the SCF isoform a precursor (e.g., a protein or peptide fragment of the sequence available at GenBank accession number NP_003985 (SEQ ID NO: 6)), or a variant or modified version thereof. Antibodies can also be raised by immunization with a translation product of the NCBI Reference Gene Sequence for SCF (e.g., accession number NG_012098 (SEQ ID NO: 7)) or variants or fragments thereof.

In some embodiments, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

Polyclonal antibodies can be prepared by any known method. Polyclonal antibodies can be raised by immunizing an animal (e.g., a rabbit, rat, mouse, donkey, etc) by multiple subcutaneous or intraperitoneal injections of the relevant antigen (a purified peptide fragment, full-length recombinant protein, fusion protein, etc.) optionally conjugated to KLH, serum albumin, etc., diluted in sterile saline, and combined with an adjuvant to form a stable emulsion. The polyclonal antibody is then recovered from blood, ascites, and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

For preparation of monoclonal antibodies, any technique that provides for the production of antibody molecules by continuous cell lines in culture may be used (see e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein and the trioma technique, the human B-cell hybridoma technique (See, e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In some embodiments provided herein, the antibodies are prepared from a hybridoma. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated in vitro (e.g., in culture) using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known. Embodiments of the technology herein provide antibodies (e.g., monoclonal antibodies) produced from a hybridoma prepared by immunizing mice with a peptide that is a portion or fragment of the SCF protein. For example, some embodiments provide an antibody or antigen-binding fragment than binds to SCF by immunizing with, e.g., a protein or peptide fragment of the sequence available at GenBank accession number NP_000890 (SEQ ID NO: 4)), or a variant or modified version thereof, or by immunizing with, e.g., a protein or peptide fragment of the sequence available at GenBank accession number NP_003985 (SEQ ID NO: 6)), or a variant or modified version thereof. Some embodiments provide an antibody or antigen-binding fragment that binds to a protein or peptide, or variants or modified versions thereof, that is a translation product of the NCBI Reference Gene Sequence for SCF (e.g., accession number NG_012098 (SEQ ID NO: 7)) or variants or fragments thereof.

For example, embodiments of the technology herein provide monoclonal antibodies produced from a hybridoma prepared by immunizing mice with a peptide of amino acid sequence SEQ ID NO: 1 or 8. Also contemplated are methods and compositions related to antibodies prepared using a variant of SEQ ID NO: 1 or 8 comprising one or more substitutions, deletions, insertions, or other changes, as long as said variant produces an antibody specific for SCF. Producing polypeptides of SEQ ID NO: 1 or 8 and similar sequences thereto can be accomplished according to various techniques well known in the art. For example, a polypeptide of SEQ ID NO: 1 or 8 or a variant thereof can be produced using a bacterial expression system and a nucleic acid encoding a polypeptide of SEQ ID NO: 1 or 8 or a variant thereof. As an example, a polypeptide according to SEQ ID NO: 1 can be produced using the nucleotide sequence according to SEQ ID NO: 2.

Moreover, human monoclonal antibodies directed against human proteins can be generated using transgenic mice carrying the complete human immune system rather than the mouse system. Splenocytes from the transgenic mice are immunized with the antigen of interest, which are used to produce hybridomas that secrete human monoclonal antibodies with specific affinities for epitopes from a human protein.

Monoclonal antibodies can also be generated by other methods known to those skilled in the art of recombinant DNA technology. For instance, combinatorial antibody display has can be utilized to produce monoclonal antibodies (see, e.g., Sastry et al., Proc. Nat. Acad. Sci. USA, 86: 5728 (1989); Huse et al., Science, 246: 1275 (1989); Orlandi et al., Proc. Nat. Acad. Sci. USA, 86:3833 (1989)). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers to a conserved 3' region can be used to amplify and isolate the heavy and light chain variable regions from a number of murine antibodies (see. e.g., Larrick et al., Biotechniques, 11: 152 (1991)). A similar strategy can also been used to amplify human heavy and light chain variable regions from human antibodies (see, e.g., Larrick et al., Methods: Companion to Methods in Enzymology, 2: 106 (1991)).

Alternatively, monoclonal antibodies can also be made using recombinant DNA methods as described in U.S. Pat. No. 4,816,567. The polynucleotides encoding a monoclonal antibody are isolated (e.g., from mature B-cells or hybridoma cells), by, e.g., RT-PCR using oligonucleotide primers that specifically amplify the genes encoding the heavy and light chains of the antibody, and their sequences are determined using conventional procedures. The isolated polynucleotides encoding the heavy and light chains are then cloned into suitable expression vectors, which, when transfected into host cells such as *E. coli* cells, simian COS cells, Chinese hamster ovary (CHO) cells, or myeloma cells that do not otherwise produce immunoglobulin protein, cause monoclonal antibodies to be generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

For example, also contemplated are chimeric mouse-human monoclonal antibodies, which can be produced by recombinant DNA techniques known in the art. For example, a gene encoding the constant region of a murine (or other species) monoclonal antibody molecule is digested with restriction enzymes to remove the region encoding the murine constant region, and the equivalent portion of a gene encoding a human constant region is substituted (see, e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 (each of which is herein incorporated by reference in its entirety); Better et al., Science, 240:1041-1043 (1988); Liu et al., Proc. Nat. Acad. Sci. USA, 84:3439-3443 (1987); Liu et al., J. Immunol., 139:3521-3526 (1987); Sun et al., Proc. Nat. Acad. Sci. USA, 84:214-218 (1987); Nishimura et al., Canc. Res., 47:999-1005 (1987); Wood et al., Nature, 314:446-449 (1985); and Shaw et al., J. Natl. Cancer Inst., 80:1553-1559 (1988)).

The chimeric antibody can be further humanized by replacing sequences of the variable region that are not directly involved in antigen binding with equivalent sequences from human variable regions. General reviews of humanized chimeric antibodies are provided by S. L. Morrison, Science, 229:1202-1207 (1985) and by Oi et al., Bio Techniques, 4:214 (1986). Those methods include isolating, manipulating, and expressing the nucleic acid sequences that encode all or part of immunoglobulin variable regions from at least one of a heavy or light chain. Sources of such nucleic acid are well known to those skilled in the art. The recombinant DNA encoding the chimeric antibody, or fragment thereof, can then be cloned into an appropriate expression vector.

Suitable humanized antibodies can alternatively be produced by CDR substitution (see, e.g., U.S. Pat. No. 5,225,539; Jones et al., Nature, 321:552-525 (1986); Verhoeyan et al., Science, 239:1534 (1988); and Beidler et al., J. Immunol., 141:4053 (1988)). All of the CDRs of a particular human antibody may be replaced with at least a portion of a non-human CDR or only some of the CDRs may be replaced with non-human CDRs. It is only necessary to replace the number of CDRs important for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs using oligonucleotide site-directed mutagenesis.

Also contemplated are chimeric and humanized antibodies in which specific amino acids have been substituted, deleted, or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In certain embodiments provided herein, it is desirable to use an antibody fragment. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). For example, papain digestion of antibodies produces two identical antigen-binding fragments, called Fab fragments, each with a single antigen-binding site, and a residual Fc fragment. Pepsin treatment yields an $F(ab')_2$ fragment that has two antigen-combining sites and is still capable of cross-linking antigen.

However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

Fv is the minimum antibody fragment which contains a complete antigen-recognition and antigen-binding site. This region consists of a dimer of one heavy-chain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. $F(ab')_2$ antibody fragments originally were produced as pairs of Fab' fragments which have hinge cysteines between them. Other chemical couplings of antibody fragments are also known to the skilled artisan.

The technology herein provided also contemplates modifying an antibody to increase its serum half-life. This can be achieved, for example, by incorporating a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The technology embraces variants and equivalents which are substantially homologous to the chimeric, humanized, and human antibodies, or antibody fragments thereof, provided herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

An additional embodiment utilizes the techniques known in the art for the construction of Fab expression libraries (Huse et al., Science, 246:1275-1281 (1989)) to allow rapid and easy identification of monoclonal Fab fragments with the desired specificity.

Also, this technology encompasses bispecific antibodies that specifically recognize SCF. Bispecific antibodies are antibodies that are capable of specifically recognizing and binding at least two different epitopes. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

Techniques described for the production of single chain antibodies (U.S. Pat. No. 4,946,778; herein incorporated by reference) can be adapted to produce specific single chain antibodies as desired. Single-chain Fv antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the single-chain Fv antibody fragments to form the desired structure for antigen binding. For a review of single-chain Fv antibody fragments, see Pluckthun in The Pharmacology of Monoclonal Antibodies, vol. 113, Rosenburg and Moore eds., Springer-Verlag, New York, pp. 269-315 (1994).

3. Other SCF Inhibitors

It is also contemplated that inhibiting SCF can be accomplished by a variety of other types of inhibitors. For example, in some embodiments a small interfering RNA (siRNA) can be designed to target and degrade SCF mRNA. siRNAs are double-stranded RNA molecules of 20-25 nucleotides in length. While not limited in their features, typically an siRNA is 21 nucleotides long and has 2-nt 3' overhangs on both ends. Each strand has a 5' phosphate group and a 3' hydroxyl group. In vivo, this structure is the result of processing by dicer, an enzyme that converts either long dsRNAs or small hairpin RNAs into siRNAs. However, siRNAs can also be synthesized and exogenously introduced into cells to bring about the specific knockdown of a gene of interest. Essentially any gene of which the sequence is known can be targeted based on sequence complementarity with an appropriately tailored siRNA. For example, those of ordinary skill in the art can synthesize an siRNA (see, e.g., Elbashir, et al., Nature 411: 494 (2001); Elbashir, et al. Genes Dev 15:188 (2001); Tuschl T, et al., Genes Dev 13:3191 (1999)).

In some embodiments, RNAi is utilized to inhibit SCF. RNAi represents an evolutionarily conserved cellular defense for controlling the expression of foreign genes in most eukaryotes, including humans. RNAi is typically triggered by double-stranded RNA (dsRNA) and causes sequence-specific degradation of single-stranded target RNAs (e.g., an mRNA). The mediators of mRNA degradation are small interfering RNAs (siRNAs), which are normally produced from long dsRNA by enzymatic cleavage in the cell. siRNAs are generally approximately twenty-one nucleotides in length (e.g. 21-23 nucleotides in length) and have a base-paired structure characterized by two nucleotide 3' overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, an RNase III enzyme (e.g., Dicer) converts the longer dsRNA into 21-23 nt double-stranded siRNA fragments. In some embodiments, RNAi oligonucleotides are designed to target the junction region of fusion proteins. Chemically synthesized siRNAs have become powerful reagents for genome-wide analysis of mammalian gene function in cultured somatic cells. Beyond their value for validation of gene function, siRNAs also hold great potential as gene-specific therapeutic agents (see, e.g., Tuschl and Borkhardt, *Molecular Intervent.* 2002; 2(3): 158-67, herein incorporated by reference).

The transfection of siRNAs into animal cells results in the potent, long-lasting post-transcriptional silencing of specific genes (Caplen et al, *Proc Natl Acad Sci U.S.A.* 2001; 98: 9742-47; Elbashir et al., *Nature.* 2001; 411:4 94-98; Elbashir et al., *Genes Dev.* 2001; 15: 188-200; and Elbashir et al., *EMBO J.* 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA and their protein products, frequently to undetectable levels. The silencing effect can last several months, and is extraordinarily specific—a one-nucleotide mismatch between the target RNA and the central region of the siRNA is frequently sufficient to prevent silencing (Brummelkamp et al, *Science* 2002; 296: 550-53; and Holen et al, *Nucleic Acids Res.* 2002; 30: 1757-66, both of which are herein incorporated by reference).

An important factor in the design of siRNAs is the presence of accessible sites for siRNA binding. Bahoia et al., (*J. Biol. Chem.,* 2003; 278: 15991-97; herein incorporated by reference) describe the use of a type of DNA array called a scanning array to find accessible sites in mRNAs for designing effective siRNAs. These arrays comprise oligonucleotides ranging in size from monomers to a certain maximum, usually Co-mers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, e.g., to retain efficacy and target specificity (Sohail et al, *Nucleic Acids Res.,* 2001; 29(10): 2041-45). Additional methods and concerns for selecting siRNAs are described, for example, in WO 05054270, WO05038054A1, WO03070966A2, J Mol. Biol. 2005 May 13; 348(4):883-93, J Mol. Biol. 2005 May 13; 348(4):871-81, and Nucleic Acids Res. 2003 Aug. 1; 31(15): 4417-24, each of which is herein incorporated by reference in its entirety. In addition, software (e.g., the MWG online siMAX siRNA design tool) is commercially or publicly available for use in the selection and design of siRNAs and RNAi reagents.

In some embodiments, the present invention utilizes siRNA including blunt ends (See e.g., US20080200420, herein incorporated by reference in its entirety), overhangs (See e.g., US20080269147A1, herein incorporated by reference in its entirety), locked nucleic acids (See e.g., WO2008/006369, WO2008/043753, and WO2008/051306, each of which is herein incorporated by reference in its entirety). In some embodiments, siRNAs are delivered via gene expression or using bacteria (See e.g., Xiang et al., Nature 24: 6 (2006) and WO06066048, each of which is herein incorporated by reference in its entirety).

In other embodiments, shRNA techniques (See e.g., 20080025958, herein incorporated by reference in its entirety) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

The present invention also includes pharmaceutical compositions and formulations that include the RNAi compounds of the present invention as described below.

SCF exists in both transmembrane and soluble forms. Upon cleavage of the SCF soluble domain from the transmembrane form, SCF is released from the cell surface to function as the ligand of c-Kit. Thus, it is contemplated that SCF activity can be altered by inhibiting the release of soluble SCF from the membrane-bound form, for example, by inhibiting or otherwise reducing the activity of a protease that cleaves the soluble domain from the membrane-bound form.

In addition, it is contemplated that SCF can be inhibited by chemicals (e.g., a small molecule, e.g., a pharmacological agent) or other biological agents that bind or modify SCF. For example, one of ordinary skill in the art can design and produce RNA aptamers or other nucleic acids that specifically recognize and bind to SCF, for instance by using SELEX or other in vitro evolution methods known in the art. Furthermore, SCF activity can be inhibited by specifically degrading SCF or inducing an altered conformation of SCF such that it is less effective in interacting with c-Kit. In some embodiments, the SCF inhibitor is a "designed ankyrin repeat protein" (DARPin) (see, e.g., Stumpp MT & Amstutz P, "DARPins: a true alternative to antibodies", *Curr Opin Drug Discov Devel* 2007, 10(2): 153-59, incorporated herein in its entirety for all purposes). In some embodiments, SCF is inhibited by a small molecule, e.g., a small molecule that binds to SCF and blocks its function (e.g., inhibits its binding and/or other interaction (e.g., an activating interaction) with the c-Kit receptor).

It is contemplated that altering SCF activity can be effected by inhibiting the expression of SCF, for instance, by inhibiting the transcription of SCF, by inhibiting the translation of SCF, by inhibiting the processing of the SCF mRNA, by inhibiting the processing of the SCF polypeptide, by inhibiting the folding of the SCF polypeptide, by inhibiting trafficking of SCF within a cell, or by inhibiting the insertion of SCF into the plasma membrane. SCF activity can be altered by changes in chromatin structure or other means of epigenetic regulation of SCF (e.g., changes in DNA methylation). Also, SCF activity may be altered by specifically sequestering SCF in a vesicle or other cellular compartment that hinders its action upon c-Kit.

4. Therapies Using Inhibitors of SCF

Inhibiting SCF finds use in therapies to treat disease. Accordingly, provided herein are therapies comprising inhibiting SCF to benefit individuals suffering from disease. In particular, as shown herein, disease states involving fibrosis and tissue remodeling demonstrate aberrant SCF activity. For example, fibroblasts isolated from diseased individuals with fibrotic or tissue remodeling phenotypes directly respond to SCF, which results in the generation of a more severe phenotype that includes increased collagen production. As such, as shown herein, inhibiting SCF can significantly affect the generation of severe disease consequences including inflammation and remodeling of target tissue. Also contemplated are therapies targeting SCF during the generation of fibrosis associated with acute and chronic disorders that have either a dynamic disease course or a more predictable disease course. Indications that can benefit from therapy inhibiting SCF include, but are not limited to, idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Importantly, therapies targeting SCF reduce or eliminate toxic effects associated with other similar therapies, for example those targeting c-Kit. These undesirable toxic effects are associated with targeting an intracellular, rather than extracellular, target, and the more widespread and general changes in cell signaling that result. While the therapies are not limited in their route of administration, embodiments of the technology provided herein deliver the SCF inhibitor via the airway by intranasal administration. Such administration allows direct delivery of the therapeutic agent to target tissues in pulmonary diseases involving fibrosis and tissue remodeling, rather than relying on systemic delivery via an orally administered composition.

In certain embodiments, a physiologically appropriate solution containing an effective concentration of an antibody specific for SCF can be administered topically, intraocularly, parenterally, orally, intranasally, intravenously, intramuscularly, subcutaneously, or by any other effective means. In particular, the antibody may delivered into an airway of a subject by intranasal administration. Alternatively, a tissue can receive a physiologically appropriate composition (e.g., a solution such as a saline or phosphate buffer, a suspension, or an emulsion, which is sterile) containing an effective concentration of an antibody specific for SCF via direct injection with a needle or via a catheter or other delivery tube. Any effective imaging device such as X-ray, sonogram, or fiberoptic visualization system may be used to locate the target tissue and guide the admistration. In another alternative, a physiologically appropriate solution containing an effective concentration of an antibody specific for SCF can be administered systemically into the blood circulation to treat tissue that cannot be directly reached or anatomically isolated. Such manipulations have in common the goal of placing an effective concentration of an antibody specific for SCF in sufficient contact with the target tissue to permit the antibody specific for SCF to contact the tissue.

With respect to administration of a SCF inhibitor (e.g., an antibody specific for SCF) to a subject, it is contemplated that the SCF inhibitor be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

In some embodiments, a SCF inhibitor (e.g., an antibody specific for SCF) according to the technology provided herein is administered in a pharmaceutically effective amount. In some embodiments, a SCF inhibitor (e.g., an antibody specific for SCF) is administered in a therapeutically effective dose. The dosage amount and frequency are selected to create an effective level of the SCF inhibitor without substantially harmful effects. When administered, the dosage of a SCF inhibitor (e.g., an antibody specific for SCF) will generally range from 0.001 to 10,000 mg/kg/day or dose (e.g., 0.01 to 1000 mg/kg/day or dose; 0.1 to 100 mg/kg/day or dose).

Pharmaceutical compositions preferably comprise one or more compounds of the present invention associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro ed., 1985).

In some embodiments, a single dose of a SCF inhibitor (e.g., an antibody specific for SCF) according to the technology provided herein is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years; e.g., for the lifetime of the subject). In such embodiments, compounds may be taken on a regular scheduled basis (e.g., daily, weekly, etc.) for the duration of the extended period.

In some embodiments, a SCF inhibitor (e.g., an antibody specific for SCF) according to the technology provided herein is co-administered with another compound or more than one other compound (e.g., 2 or 3 or more other compounds).

5. Kits

Some embodiments provide herein kits for the treatment of a subject. In some embodiments, the kits include an inhibitor of SCF and appropriate solutions and buffers. Embodiments include all controls and instructions for use.

EXAMPLES

Materials and methods

SCF Nucleotide Sequences and Proteins

The human gene encoding Stem Cell Factor (SCF) is also known as kit ligand and has the official symbol KITLG and HGNC number HGNC:6343. SCF is also known as SF; MGF; SCF; FPH2; KL-1; Kit1; SHEP7; and kit-ligand. Two transcript variants encoding different isoforms have been found for this gene. The SCF (kit ligand) isoform b precursor is available at GenBank accession numbers NM_000899 (mRNA transcript; SEQ ID NO: 3) and NP_000890 (protein sequence; SEQ ID NO: 4). The SCF (kit ligand) isoform a precursor is available at GenBank accession numbers NM_003994 (mRNA transcript; SEQ ID NO: 5) and NP_003985 (protein sequence; SEQ ID NO: 6). The NCBI Reference Gene Sequence has accession number NG_012098 (SEQ ID NO: 7). For both isoforms, the first 25 amino acids comprise the signal peptide and the mature form begins at amino acid 26. The first 11 amino acids of the mature form are EGICRNRVTNN (SEQ ID NO: 8).

Bleomycin Model

Interstitial pulmonary fibrosis was induced in specific pathogen-free (SPF) female, CBA/J mice (6-8 weeks old; The Jackson Laboratory, Bar Harbor, Me.) by the i.t. injection of 0.003 U of bleomycin (Blenoxane, sterile bleomycin sulfate; Bristol-Meyers Pharmaceuticals, Evansville, Ind.; 0.15 U/Kg of mouse body weight) dissolved in 60 μl of phosphate-buffered saline (PBS). Controls received 60 μl of PBS by the same route. All procedures were conducted in a sterile environment and were approved by the institutional animal care and use committee.

Whole Lung Histology

Following anesthesia-induced euthanasia, whole lungs from bleomycin-challenged mice were fully inflated with 10% formalin, dissected, and placed in fresh formalin for 24 hours. Routine histological techniques were used to embed the entire lung in paraffin, and 5-μm sections of whole lung were stained with hematoxylin and eosin.

Production and Administration of Anti-SCF Polyclonal Antibodies

Anti-SCF antibodies were generated by immunizing rabbits with recombinant (whole protein) SCF and generating polyclonal SCF-specific antibodies. Polyclonal antibodies were isolated from the serum using a protein G column. The isolated IgG portion was quantified and used at the specified concentrations suspended in saline. IgG from pre-immune serum was isolated in a similar fashion for use as a control. Briefly, 100, 150 or 200 μg of control or anti-SCF was given to mice by intranasal administration 7 days after treatment with bleomycin. This treatment was repeated on a daily basis until 12 days after bleomycin administration. Thus, the treatment protocol is considered therapeutic.

Generation of Mouse Anti-human Monoclonal Antibodies

After identifying an immunogenic human peptide (e.g., SEQ ID NO: 1 or 8), mice were immunized with a standard protocol. The determination of high titer serum antibodies indicated the appropriate immunization and fusion hybridomas were made. Culture supernatants were analyzed from individual clones for SCF-specific antibody and chosen based upon specificity. Five hybridomas producing specific monoclonal antibodies against the peptide were propagated and the monoclonal with the highest titer was subsequently tested in biologically relevant cultures. In some embodiments, a peptide having the sequence EGICRNRVTNN (SEQ ID NO: 8) was used to generate an antibody (e.g., a monoclonal antibody). In some embodiments, any peptide fragment (e.g., an antigenic fragment) of the SCF protein sequence (e.g., as provided by SEQ ID NO: 4 and/or SEQ ID NO: 6) is used to generate antibodies. In some embodiments, mutant or variant forms (e.g., comprising one or more amino acid substitutions with respect to the sequences provided by SEQ ID NO: 4 and SEQ ID NO: 6) of SCF are used to provide a peptide for generating antibodies. It is to be understood that these embodiments comprise additions, deletions, substitutions, post-translational modifications (e.g., glycosylation, cyclization, N- and C-terminal modification, etc.) and other variations of proteins and peptides that are known in the art of molecular biology as applied to provide a peptide for antibody generation.

Testing Mouse Anti-human Monoclonal Antibodies

To demonstrate that monoclonal antibodies inhibit SCF, mast cell lines that are sensitive to SCF were tested. The HMC-1 cell line, a mastocytoma cell line that expresses c-Kit and responds to SCF was first used. In brief, HMC-1 cells were cultured in specific growth media and plated in 24-well tissue culture plates at a concentration of $1\times10^6$ cells/ml. Recombinant human SCF (1-100 ng/ml) was mixed with monoclonal anti-SCF antibody (12 μg/ml) and incubated at 37° C. for 30 minutes. After incubation, the antibody/SCF or SCF alone was added to the HMC-1 cells. After 1 hour or 24 hours, the cultured HMC-1 cells were harvested and mRNA and protein levels were measured as an indication of SCF inhibition by the monoclonal antibodies.

Analysis of mRNA Expression by Quantitative PCR

Cells or tissue to be tested were dispersed in 1 ml of Trizol reagent (Invitrogen). RNA was isolated as described (Invitrogen), and 5 μg of mRNA was reverse-transcribed to assess gene expression. Detection of cytokine mRNA was determined using previously available primer/probe sets (PE Biosystems, Foster City, Calif.) and analyzed using an ABI Prism 7500 Sequence Detection System (Applied Biosystems, Foster City, Calif.). GAPDH mRNA was measured as a control for normalizing mRNA expression. Changes in gene expression were calculated relative to gene expression in unchallenged mice.

Determination of Cytokine Production

Protein levels of cytokines were quantified using a Bio-Plex bead-based cytokine assay purchased from Bio-Rad Laboratories (Hercules, Calif.). Using standard protocols, the level of cytokines can be quickly and consistently assessed with this methodology.

Statistical Analysis

Data were analyzed using Prism GraphPad software. Unless otherwise specified, data shown are representative of two or more experiments. Statistical significance in all experiments was determined by one-way ANOVA, followed by a Newman-Keuls post test. Significant differences were regarded as $p<0.05$.

Isolation and Propagation of Pulmonary Fibroblasts from Patient Populations

The Institutional Review Board at the University of Michigan Medical School approved this study. All patients underwent clinical evaluation, including chest radiography, lung function measurements, and thin-section computed tomography before fiber optic bronchoscopy. In these patients, interstitial pneumonia was determined from a compilation of symptoms, physiological symptoms, and radiographical findings. Surgical lung biopsies were obtained via the Clinical Core at the University of Michigan Medical School from patients suspected of having interstitial pneumonia between May 2000 and May 2002. Histologically normal lung was obtained from resected specimens in patients undergoing thoracic resection. Each biopsy was processed separately using sterile technique in a laminar flow hood and processed for culturing primary fibroblast lines. Two pathologists who were unaware of any other clinical findings independently reviewed each biopsy and histological classification was based on previously published criteria for idiopathic interstitial pneumonia.

Interstitial pneumonia and normal biopsies were finely minced and the dispersed tissue pieces were placed into 150-$cm^2$ cell culture flasks (Corning Inc., Corning, N.Y.) containing Dulbecco's modified Eagle's medium (DMEM, Bio-Whittaker, Walkersville, Md.) supplemented with 15% fetal bovine serum (DMEM-15, BioWhittaker), 1 mmol/L glutamine (BioWhittaker), 100 U/ml penicillin (BioWhittaker), 100 μg/ml streptomycin (BioWhittaker), and 0.25 μg amphotericin B (Fungizone; BioWhittaker). All primary lung cell lines were maintained in DMEM-15 at 37° C. in a 5% $CO_2$ incubator and were serially passaged a total of five times to yield pure populations of lung fibroblasts. All primary fibroblast cell lines were used at passages 6 to 10 in the experiments outlined below and all of the experiments were performed under comparable conditions.

1. Anti-SCF Antibody Reduces Fibrosis and Inflammation

Experiments conducted while developing embodiments of the technology demonstrated that anti-SCF antibody reduced fibrosis and inflammation. Pulmonary fibrosis was induced in mice as described. On day 7 following bleomycin injury, mice were subjected to treatment with anti-SCF antibodies delivered into the airway by intranasal administration. Treatment continued until day 12 following bleomycin exposure. Lungs were harvested on day 16 and examined by microscopy and a series of micrographs were taken. Lung histology demonstrated that anti-SCF antibodies reduced overall inflammation. In addition, Masson's trichrome staining, which designates collagen deposition, was reduced.

2. Anti-SCF Antibody Reduces Levels of SCF, Hydroxyproline, IL-25, and IL-13

Levels of hydroxyproline and particular cytokines were monitored while developing embodiments of the technology. Lung tissue sections from the above experiment were examined for the presence of hydroxyproline, a collagen precursor. The data demonstrated that the anti-SCF antibody reduced the production of hydroxyproline and plasma levels of SCF in a dose-dependent manner (FIGS. 1A and D). Also, IL-25 and IL-13 expression, measured as a function of mRNA levels, were reduced, as was expression of IL-25 receptor (FIGS. 1B, C, and E).

In particular, the experiments tested the effect of anti-SCF antibody treatment in the BLM model (FIG. 1). Mice were treated with saline (FIG. 1, "SAL") or BLM (FIG. 1, "BLM") on day 0. On days 8 and 12, different groups were also treated intratracheally with non-immune (FIG. 1, "IgG") or anti-SCF antibodies (FIG. 1, "aSCF") at the indicated doses. H&E stained lung tissue sections from each treatment group were acquired and examined. Fibrosis was quantified biochemically as lung hydroxyproline content (FIG. 1A). Lungs were then analyzed for IL-13 mRNAs by real time PCR (FIG. 1C). Plasma and lung tissue collected from SAL- or BLM-treated mice were then analyzed for soluble SCF by ELISA (FIG. 1D) or IL-25 mRNA by real time PCR (FIG. 1B). Values represent the means+/−the standard error with an n=7. A single asterisk (*) indicates statistical significance ($P<0.05$) when compared to the saline control group, while double asterisks (**) indicate significance with respect to the BLM+IgG control group.

3. IL-4 Stimulates c-kit Expression in Human Fibroblasts

Figure 2:
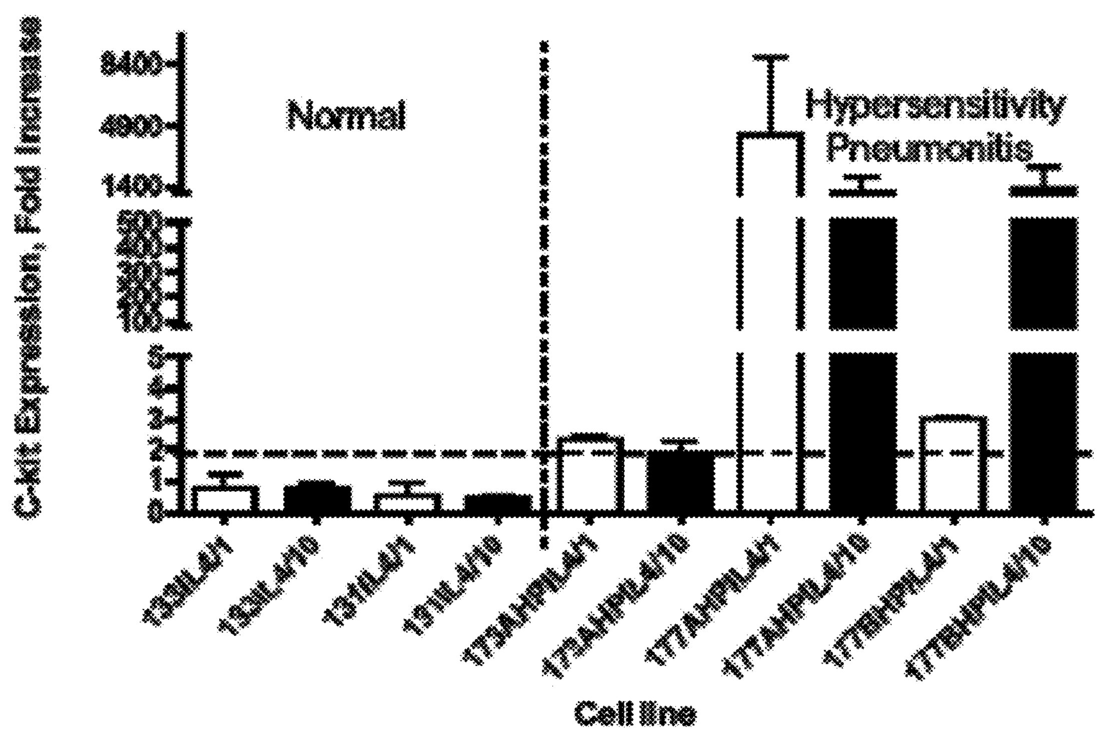
FIG. 2 shows a plot demonstrating that IL-4 stimulates c-kit expression in human fibroblasts.

Experiments conducted while developing embodiments of the technology demonstrated that IL-4 stimulated c-kit expression in human fibroblasts. In addition to the mouse model of pulmonary inflammation, SCF receptor is expressed in fibroblast populations from patients diagnosed with hypersensitivity pneumonitis and who thus have a pro-fibrotic environment. Pulmonary fibroblasts were grown from normal areas of lungs from patients (normal) and those diagnosed with hypersensitivity pneumonitis. Expression of c-kit was measured after stimulation with IL-4 at 1 or 10 ng/ml. Individual cell lines (133, 131, 173, 177A, 177B) were assessed using real-time PCR. Compared to lung fibroblasts grown from patients with non-fibrotic disease, fibroblasts from the hypersensitivity pneumonitis patients displayed significant upregulation of c-kit when stimulated with IL-4, a fibrosis-associated cytokine. The data demonstrated that SCF activated fibroblasts from inflammatory lesions, but not those from normal tissue, and promoted the expression of fibrosis-associated genes including collagen (FIG. 2).

4. A Mouse Anti-human Monoclonal Antibody Blocks SCF-induced HMC Mast Cell Activation.

Figure 4:
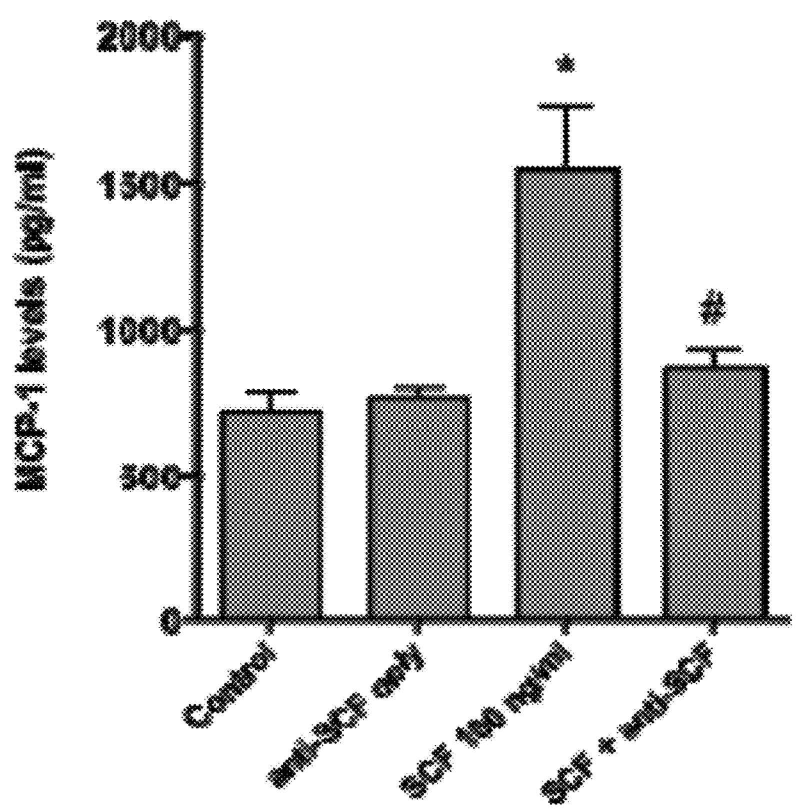
FIG. 4 shows a plot demonstrating that a monoclonal antibody specific for SCF inhibits the activation of HMC-1 cells for MCP-1 production.

Experiments conducted while developing embodiments of the technology demonstrated that the monoclonal antibody specific for SCF inhibited the activation of HMC-1 cells for MCP-1 production. The activation of mast cells is a classic SCF-induced response that can be used to monitor antibody neutralization of SCF-mediated cytokine responses. Previous studies have demonstrated that monocyte chemotactic protein (MCP)-1 is strongly upregulated by SCF in mast cells. A monoclonal antibody was produced against SEQ ID NO: 1 (FIG. 3). The efficacy of this antibody was tested using a human mast cell line, HMC-1, stimulated with 100 ng/ml of SCF. The monoclonal antibody (6 μg/ml) was preincubated with the recombinant SCF for 5 minutes prior to placing the SCF or the SCF plus anti-SCF onto the cultured HMC-1 cells ($1\times10^6$ cells/ml). The cells were subsequently incubated for 12 hours, after which the cell-free supernatant was collected and MCP-1 was analyzed by Bio-Plex. The data illustrate that the monoclonal antibody specific for SCF inhibited the activation of HMC-1 cells for MCP-1 production (FIG. 4).

5. SCF-deficient Mice Subjected to BLM-induced Injury have Reduced Fibrosis.

Figure 5:
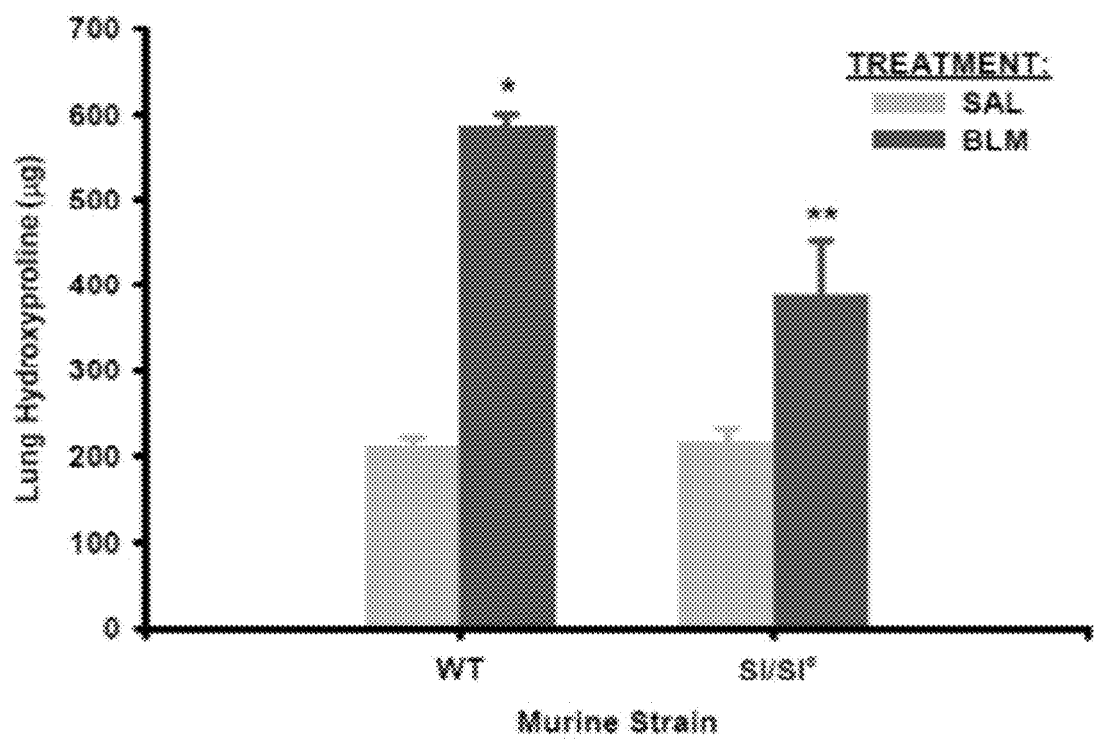
FIG. 5 shows a plot demonstrating that a lower amount of hydroxyproline is detected in a mouse deficient in SCF production after bleomycin injury.

During the development of embodiments of the technology provided herein, the effects of SCF deficiency in $Kit1^{S}1$/$Kit1^{S1-d}$ mutant mice were examined (FIG. 5). These mice have a complete deletion of the SCF gene in one allele (S1) and a deletion of the membrane-bound ligand in the other ($S1^{d}$), which significantly decreases the expression of soluble SCF. When these mice and their wild type controls (WT) were subjected to BLM-induced lung injury, there was a significantly reduced fibrosis in the mutant mice compared to wild type mice, both morphologically (Masson trichrome stain) and biochemically by hydroxyproline analysis (FIG. 5).

Wild-type and SCF deficient mice were treated with saline ("SAL") or BLM ("BLM") on day 0 and lungs were harvested 21 days later. Fibrosis was quantified biochemically as lung hydroxyproline content. Values represent the mean+/−standard deviation with an n=3. A single asterisk (*) indicates statistical significance ($P<0.05$) when compared to the WT saline-treated control mean, while double asterisks (**) indicate significance when compared to the WT BLM-treated group.

Similar suppression of cytokine expression and telomerase induction was also noted in S1/S1d mice. These data taken together indicated an essential role for the SCF/c-Kit signaling induced pulmonary fibrosis.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

31623-US-2-ORD_ST25.txt.

We claim:

1. A method of treating a disease that is a fibrotic disease or a tissue remodeling disease comprising administering a therapeutically effective amount of an anti-stem cell factor monoclonal antibody that specifically binds to SEQ ID NO: 1 or an antigen-binding fragment of said anti-stem cell factor monoclonal antibody to a subject with or at risk for a disease that is a fibrotic disease or a tissue remodeling disease.

2. The method of claim 1, wherein the subject has an abnormal activity of stem cell factor or abnormal collagen production.

3. The method of claim 1, wherein the disease is fibrosis, a remodeling disease, or a pulmonary disease.

4. The method of claim 1, wherein the disease is idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediastinal fibrosis, nodular subepidermal fibrosis, fibrous histiocytoma, fibrothorax, hepatic fibrosis, fibromyalgia, gingival fibrosis, or radiation-induced fibrosis.

5. The method of claim 1, wherein the anti-stem cell factor monoclonal antibody or the antigen-binding fragment of said anti-stem cell factor monoclonal antibody is administered to the subject via a respiratory route, an intravenous route, or a subcutaneous route.

6. The method of claim 1, wherein said administering the anti-stem cell factor monoclonal antibody or the antigen-binding fragment of said anti-stem cell factor monoclonal antibody reduces an activity of a receptor and/or reduces an interaction of stem cell factor with a receptor.

7. The method of claim 6, wherein the receptor is a receptor tyrosine kinase.

8. The method of claim 6, wherein the receptor is c-Kit.

9. The method of claim 1, wherein administering the anti-stem cell factor monoclonal antibody or the antigen-binding fragment of said anti-stem cell factor monoclonal antibody to a subject results in a direct inhibition of fibroblast activation.

10. A method comprising providing an anti-stem cell factor monoclonal antibody that specifically binds to SEQ ID NO: 1 or an antigen-binding fragment of said anti-stem cell factor monoclonal antibody and administering the anti-stem cell factor monoclonal antibody or the antigen-binding fragment of said anti-stem cell factor monoclonal antibody to a cell or tissue.

11. A method of treating a disease that is idiopathic pulmonary fibrosis, chronic obstructive pulmonary disease, acute respiratory distress syndrome, peribronchial fibrosis, hypersensitivity pneumonitis, sclerodoma, renal fibrosis, hepatic fibrosis, fibromyalgia, or radiation-induced fibrosis, the method comprising administering a therapeutically effective amount of an anti-stem cell factor monoclonal antibody or an antigen-binding fragment of said anti-stem cell factor monoclonal antibody to a subject having or at risk for having the disease that is idiopathic pulmonary fibrosis, chronic obstructive pulmonary disease, acute respiratory distress syndrome, peribronchial fibrosis, hypersensitivity pneumonitis, sclerodoma, renal fibrosis, hepatic fibrosis, fibromyalgia, or radiation-induced fibrosis.

12. The method of claim 11 wherein the anti-stem cell factor monoclonal antibody or the antigen-binding fragment of said anti-stem cell factor monoclonal antibody specifically binds to SEQ ID NO: 1.

13. The method of claim 11, wherein the subject has an abnormal activity of stem cell factor or abnormal collagen production.

14. The method of claim 11, wherein the anti-stem cell factor monoclonal antibody or the antigen-binding fragment of said anti-stem cell factor monoclonal antibody is administered to the subject via a respiratory route, an intravenous route, or a subcutaneous route.

15. The method of any one of claim 1 or claim 11, wherein the anti-stem cell factor monoclonal antibody or the antigen-binding fragment of said anti-stem cell factor monoclonal antibody is administered to the subject as a dry powder or in a nebulized form.

16. The method of claim 5 or claim 14, wherein the anti-stem cell factor monoclonal antibody or the antigen-binding fragment of said anti-stem cell factor monoclonal antibody is administered to the subject via inhalation.

17. The method of claim 11, wherein said administering the anti-stem cell factor monoclonal antibody or the antigen-binding fragment of said anti-stem cell factor monoclonal antibody reduces an activity of a receptor and/or reduces an interaction of stem cell factor with a receptor.

18. The method of claim 17, wherein the receptor is a receptor tyrosine kinase.

19. The method of claim 17, wherein the receptor is c-Kit.

20. The method of claim 11, wherein administering the anti-stem cell factor monoclonal antibody or the antigen-binding fragment of said anti-stem cell factor monoclonal antibody to a subject results in a direct inhibition of fibroblast activation.

21. The method of claim 11 wherein the disease is idiopathic pulmonary fibrosis.

22. The method of claim 11 wherein the disease is chronic obstructive pulmonary disease.

23. The method of claim 11 wherein the disease is acute respiratory distress syndrome.

24. The method of claim 11 wherein the disease is peribronchial fibrosis.

25. The method of claim 11 wherein the disease is hypersensitivity pneumonitis.

26. The method of claim 11 wherein the disease is scleroderma.

27. The method of claim 11 wherein the disease is renal fibrosis.

28. The method of claim 11 wherein the disease is hepatic fibrosis.

29. The method of claim 11 wherein the disease is fibromyalgia.

30. The method of claim 11 wherein the disease is radiation-induced fibrosis.

31. A method of treating a disease that is a fibrotic disease or a tissue remodeling disease comprising administering a therapeutically effective amount of an anti-stem cell factor monoclonal antibody that specifically binds to a transmembrane form of stem cell factor or an antigen-binding fragment of said anti-stem cell factor monoclonal antibody to a subject with or at risk for a disease that is a fibrotic disease or a tissue remodeling disease.

32. The method of claim 31, wherein the subject has an abnormal activity of stem cell factor or abnormal collagen production.

33. The method of claim 31, wherein the disease is fibrosis, a remodeling disease, or a pulmonary disease.

34. The method of claim 31 wherein the disease is idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediastinal fibrosis, nodular subepidermal fibrosis, fibrous histiocytoma, fibrothorax, hepatic fibrosis, fibromyalgia, gingival fibrosis, or radiation-induced fibrosis.

35. The method of claim 34 wherein the disease is asthma.

36. The method of claim 31, wherein the anti-stem cell factor monoclonal antibody or the antigen-binding fragment of said anti-stem cell factor monoclonal antibody thereof is administered to the subject via a respiratory route, an intravenous route, or a subcutaneous route.

37. The method of claim 31, wherein administering the anti-stem cell factor monoclonal antibody or the antigen-binding fragment of said anti-stem cell factor monoclonal antibody to a subject results in a direct inhibition of fibroblast activation.

38. The method of claim 31, wherein the anti-stem cell factor monoclonal antibody or the antigen-binding fragment of said anti-stem cell factor monoclonal antibody is administered to the subject as a dry powder or in a nebulized form.

39. The method of claim 36, wherein the anti-stem cell factor monoclonal antibody or the antigen-binding fragment of said anti-stem cell factor monoclonal antibody is administered to the subject via inhalation.

* * * * *

```
                     SEQUENCE LISTING

<160> NUMBER OF SEQ ID NOS: 8

<210> SEQ ID NO 1
<211> LENGTH: 15
<212> TYPE: PRT
<213> ORGANISM: Homo sapiens

<400> SEQUENCE: 1

Ser Ser Ser Asn Arg Lys Ala Lys Asn Pro Pro Gly Asp Ser Cys
1               5                   10                  15


<210> SEQ ID NO 2
<211> LENGTH: 45
<212> TYPE: DNA
<213> ORGANISM: Homo sapiens

<400> SEQUENCE: 2

tcgtcgtcga accgcaaagc gaaaaacccg ccgggcgatt cgtgc                   45


<210> SEQ ID NO 3
<211> LENGTH: 5460
<212> TYPE: DNA
<213> ORGANISM: Homo sapiens

<400> SEQUENCE: 3

gggcttcgct cgccgcctcg cgccgagact agaagcgctg cgggaagcag ggacagtgga     60

gagggcgctg cgctcgggct acccaatgcg tggactatct gccgccgctg ttcgtgcaat    120

atgctggagc tccagaacag ctaaacggag tcgccacacc actgtttgtg ctggatcgca    180

gcgctgcctt tccttatgaa gaagacacaa acttggattc tcacttgcat ttatcttcag    240
```

-continued

```
ctgctcctat ttaatcctct cgtcaaaact gaagggatct gcaggaatcg tgtgactaat    300
aatgtaaaag acgtcactaa attggtggca aatcttccaa aagactacat gataaccctc    360
aaatatgtcc ccgggatgga tgttttgcca agtcattgtt ggataagcga gatggtagta    420
caattgtcag acagcttgac tgatcttctg gacaagtttt caaatatttc tgaaggcttg    480
agtaattatt ccatcataga caaacttgtg aatatagtgg atgaccttgt ggagtgcgtg    540
aaagaaaact catctaagga tctaaaaaaa tcattcaaga gcccagaacc caggctcttt    600
actcctgaag aattctttag aatttttaat agatccattg atgccttcaa ggactttgta    660
gtggcatctg aaactagtga ttgtgtggtt tcttcaacat taagtcctga gaaagattcc    720
agagtcagtg tcacaaaacc atttatgtta ccccctgttg cagccagctc ccttaggaat    780
gacagcagta gcagtaatag gaaggccaaa aatccccctg gagactccag cctacactgg    840
gcagccatgg cattgccagc attgttttct cttataattg gctttgcttt tggagcctta    900
tactggaaga agagacagcc aagtcttaca agggcagttg aaaatataca aattaatgaa    960
gaggataatg agataagtat gttgcaagag aaagagagag agtttcaaga agtgtaattg   1020
tggcttgtat caacactgtt actttcgtac attggctggt aacagttcat gtttgcttca   1080
taaatgaagc agctttaaac aaattcatat tctgtctgga gtgacagacc acatctttat   1140
ctgttcttgc tacccatgac tttatatgga tgattcagaa attggaacag aatgttttac   1200
tgtgaaactg gcactgaatt aatcatctat aaagaagaac ttgcatggag caggactcta   1260
ttttaaggac tgcgggactt gggtctcatt tagaacttgc agctgatgtt ggaagagaaa   1320
gcacgtgtct cagactgcat gtaccatttg catggctcca gaaatgtcta aatgctgaaa   1380
aaacacctag ctttattctt cagatacaaa ctgcagcctg tagttatcct ggtctctgca   1440
agtagatttc agcttggata gtgagggtaa caattttttct caaagggatc tggaaaaaat   1500
gtttaaaact cagtagtgtc agccactgta cagtgtagaa agcagtggga actgtgattg   1560
gatttggcaa catgtcagct ttatagttgc cgattagtga tatgggtctg atttcgatct   1620
cttcctgatg taaaccatgc tcacccatat cccactatac aaatgcaaat ggttgcctgg   1680
ttccatttat gcaagggagc cagtactgaa ttatgccttg gcagagggga gactccaaaa   1740
gagtcatcgc aggaagaagt taagaacact gaacatcaga acagtctgcc aagaaggaca   1800
ttggcatcct gggaaagtcc gccttttccc ttgaccacta tagggtgtat aaatcgtgtt   1860
tgcaaaatgt gttatgatgt gtttatattc taaaactatt acagagctat gtaaagggac   1920
ttaggagaaa atgctgaatg taagatggtc ccatttcaat ttccaccatg ggagagccta   1980
aaaataaatt atgacattta gtatctaagg ttagaaaacc acgcccacat gctaatatgg   2040
gtgttgaaaa ctaggttact tataatgcaa ggaatcagga aactttagtt atttatagta   2100
taatcaccat tatctgttta aaggatccat ttagttaaaa tcgggcactc tatattcatt   2160
aaggtttatg aattaaaaag aaagctttat gtagttatgc atgtcagttt gctatttaaa   2220
atgtgtgaca gtgtttgtca tattaagagt gaatttggca ggaattccca agatggacat   2280
tgtgctttta aactagaact tgtaagacat tatgtgaata tcccttgcca atttttttta   2340
taataagaaa acatctgact aaagtcaaag aatgatttct tatggtttat tttgatgaaa   2400
gttcttttaa catgtcttga atgtacacat aaaggaatcc aaagctttcc attctaactt   2460
aatctttgtg ataacattat tgccatgttc tacaaccgta agatgacagt tttcaatgta   2520
gtgacacaaa agggcatgaa aaactaactg ctagctttcc tttcatttca aaagtccaag   2580
aatttctagt atatttggat tttagcttct gttcaaagca aatccagatg caactccagt   2640
```

```
aagtggcctt tgctcttttt tgtaccaaag agcccagatg attcctacag tccctttctt   2700
ctctaacatg ctgtggttcc ttaaatatga gtaatttctc taagatataa cccaggtgct   2760
ttgagaagct gcattaaggt gttcaggccc tcagatatca catggtacac ttgattagta   2820
ataaaaccag agatcaattt aaattgctga taggtcctgt ctcagtgtgt ggcattgact   2880
gttttcagga aaatagatac agattaatat gagttatgcg tgtaggttgt gtatagattg   2940
agaagataga tacttctcaa tctagtagtt tgatttattt aaccaatggt ttcagtttgc   3000
ttgagcatat gaaaatcctg cttaatgtgc ttaagagtat aataaatgtg tacttttgtc   3060
ctcaaaccta gtagctgggt tttaacactc atggacatgg tcttaatcaa tggagttaaa   3120
taaacaaatt cagcaagtta ttaaatctga catggtagga gaggggagat gtgtcctgct   3180
tattaaatgt gttggtccat tgaaagttac atggattgcc aatttttaaa acactaaagt   3240
tgaataaaat gcatgaacaa tagaaaaatg ctgaacatta ttttggatgc tagctgcttg   3300
gacattaact gtgttatttc tgctttgaga tgaaaatata tatttatctt tgcttatttt   3360
atcccagatg tgttctgaat atccttcttc ataaatcatg gaaaactcac tgctgagata   3420
gtaaaccatg aaatcgcctt ttcagttggt gccatgtatc tgacagttcc atcttggaag   3480
gtttcaaaat tacctttttaa aatgatctca gaagtctgta gattctcaat gatactgaaa   3540
gctttgcacc tctttggtag aaaccaggtc tatttagaaa atggctttat gataaatgtt   3600
gcctcctgag tgataatgaa gtgttcctgg atattgtatt gtaatttaat gtgcttacca   3660
cactgccaca ttttaatgag tcagagaaaa attaattttt cttcaataca ataatagaac   3720
aagtagccta ttctcttaaa aagtatgtga aaagaaaatt atgaaaaaat atgcatacct   3780
aatgaagtat tggttttagt aagaattaaa tacatttcat tgagctttaa agtactttgg   3840
agaaactttg gggcacgttt tcctactcta attcaactaa agttataaat aaagagaaaa   3900
actcattcag aaatcatgga ttttaaaaat attttactgc agccaagttt tcatttcaaa   3960
atgtaatttc agtttggagc ttttaggcat tatgtatatt taaaaaatat attcttcaaa   4020
aatgcatttt ggcatggtgg gatggatgtt gcaaaagata tccggagcct ccagtctgtc   4080
attaactgat atggtaaatc acctctcttc tttgggtctc aatttttat ttatctatat   4140
ggtaaactca gagatcactc cttaggggtg agtcctattg caatatgacc gacaaagaag   4200
acaaaatagc attgaaacta acccatacaa aatatccaac tctggattct gtgaataagt   4260
atcttgacca taaaaagtca ttgctgttct tgtttctaat gtaaatagtg tccattagta   4320
aaagtgaaat tcagtcttaa gtagggtgaa ttggatcacc atttacacaa gagatggctt   4380
tttcctttgc ttgaataaac attttggatc acctccaaag aatgaaaacc agtagtacgt   4440
tttagtcata ttagtcagga tgagaaacta taagatgtgt gtaacatttg gaaatgcacc   4500
aaagtgagcg tttaaatctt ctcattttat tgaaaactaa gagcagaaaa tgtaaaatgc   4560
tcatgaaggt tttgaatgcc aaaagatatt ttagaatcaa tttataaagg ggtaattcat   4620
taattacact ttaaaattgg aaagtgggat aagaaatcta aagtaaacca gcttatcttt   4680
gaaacaatat tattttgaaa ttggctttaa aataaaacca ttcagattga aattctaatt   4740
agctcatttg tggagtttga tcacacaatt cataatgttg ctgctttcca ttaactagtc   4800
ttgaaatgcc tttgtttgta aaaataaaat aatggtactt tcattttata acaaggtgtt   4860
tttttcaaga aataatccat gctaaaatgg atatttgtga tcctgaaatg tttactaagc   4920
attgtaaatt tatttataac tgccatctcc aactacatcc ttatgatgtt tttaacaata   4980
```

```
aaattaaaac aactgttaaa ctaaaaacca caccgttttc cagtacttga tctctgagct   5040

acaatactca ctaaatataa ttttccaatc aaaatattct attctatatt ctaagggtta   5100

atatgtgatt atagtgtcca cttgccacca tttttttaaa tcaatggact tgaaaagtat   5160

taatttagat ggatgcgcag atataccctc agttcagtca tagattggag tttgcatata   5220

ataatgtaaa tgtatgtcga cactattcta aatagttcta ttatgactga aatttaatta   5280

aataaaaaag gttgtaaaat gtgatgtgta tgtgtatata ctgtatgtgt actttttaaa   5340

ataggtgtat gtcccaaccc tttttatac aggtttgaat ttaaaattac atgatatata   5400

catatacttt attgttctaa ataaagaatt ttatgcactc tcaaaaaaaa aaaaaaaaaa   5460


<210> SEQ ID NO 4
<211> LENGTH: 273
<212> TYPE: PRT
<213> ORGANISM: Homo sapiens

<400> SEQUENCE: 4

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val


<210> SEQ ID NO 5
```

<211> LENGTH: 5376
<212> TYPE: DNA
<213> ORGANISM: Homo sapiens

<400> SEQUENCE: 5

```
gggcttcgct cgccgcctcg cgccgagact agaagcgctg cgggaagcag ggacagtgga     60
gagggcgctg cgctcgggct acccaatgcg tggactatct gccgccgctg ttcgtgcaat    120
atgctggagc tccagaacag ctaaacggag tcgccacacc actgtttgtg ctggatcgca    180
gcgctgcctt tccttatgaa gaagacacaa acttggattc tcacttgcat ttatcttcag    240
ctgctcctat ttaatcctct cgtcaaaact gaagggatct gcaggaatcg tgtgactaat    300
aatgtaaaag acgtcactaa attggtggca aatcttccaa aagactacat gataaccctc    360
aaatatgtcc ccgggatgga tgttttgcca agtcattgtt ggataagcga gatggtagta    420
caattgtcag acagcttgac tgatcttctg gacaagtttt caaatatttc tgaaggcttg    480
agtaattatt ccatcataga caaacttgtg aatatagtgg atgaccttgt ggagtgcgtg    540
aaagaaaact catctaagga tctaaaaaaa tcattcaaga gcccagaacc caggctcttt    600
actcctgaag aattctttag aatttttaat agatccattg atgccttcaa ggactttgta    660
gtggcatctg aaactagtga ttgtgtggtt tcttcaacat taagtcctga gaaagggaag    720
gccaaaaatc cccctggaga ctccagccta cactgggcag ccatggcatt gccagcattg    780
ttttctctta taattggctt tgcttttgga gccttatact ggaagaagag acagccaagt    840
cttacaaggg cagttgaaaa tatacaaatt aatgaagagg ataatgagat aagtatgttg    900
caagagaaag agagagagtt tcaagaagtg taattgtggc ttgtatcaac actgttactt    960
tcgtacattg gctggtaaca gttcatgttt gcttcataaa tgaagcagct ttaaacaaat   1020
tcatattctg tctggagtga cagaccacat ctttatctgt tcttgctacc catgacttta   1080
tatggatgat tcagaaattg gaacagaatg ttttactgtg aaactggcac tgaattaatc   1140
atctataaag aagaacttgc atggagcagg actctatttt aaggactgcg ggacttgggt   1200
ctcatttaga acttgcagct gatgttggaa gagaaagcac gtgtctcaga ctgcatgtac   1260
catttgcatg gctccagaaa tgtctaaatg ctgaaaaaac acctagcttt attcttcaga   1320
tacaaactgc agcctgtagt tatcctggtc tctgcaagta gatttcagct tggatagtga   1380
gggtaacaat tttctcaaa gggatctgga aaaaatgttt aaaactcagt agtgtcagcc    1440
actgtacagt gtagaaagca gtgggaactg tgattggatt tggcaacatg tcagctttat   1500
agttgccgat tagtgatatg ggtctgattt cgatctcttc ctgatgtaaa ccatgctcac   1560
ccatatccca ctatacaaat gcaaatggtt gcctggttcc atttatgcaa gggagccagt   1620
actgaattat gccttggcag aggggagact ccaaaagagt catcgcagga agaagttaag   1680
aacactgaac atcagaacag tctgccaaga aggacattgg catcctggga aagtccgcct   1740
tttcccttga ccactatagg gtgtataaat cgtgtttgca aaatgtgtta tgatgtgttt   1800
atattctaaa actattacag agctatgtaa agggacttag gagaaaatgc tgaatgtaag   1860
atggtcccat ttcaatttcc accatgggag agcctaaaaa taaattatga catttagtat   1920
ctaaggttag aaaaccacgc ccacatgcta atatgggtgt tgaaaactag gttacttata   1980
atgcaaggaa tcaggaaact ttagttattt atagtataat caccattatc tgtttaaagg   2040
atccatttag ttaaaatcgg gcactctata ttcattaagg tttatgaatt aaaaagaaag   2100
ctttatgtag ttatgcatgt cagtttgcta tttaaaatgt gtgacagtgt ttgtcatatt   2160
aagagtgaat ttggcaggaa ttcccaagat ggacattgtg cttttaaact agaacttgta   2220
```

```
agacattatg tgaatatccc ttgccaattt tttttataat aagaaaacat ctgactaaag   2280
tcaaagaatg atttcttatg gtttattttg atgaaagttc ttttaacatg tcttgaatgt   2340
acacataaag gaatccaaag ctttccattc taacttaatc tttgtgataa cattattgcc   2400
atgttctaca accgtaagat gacagttttc aatgtagtga cacaaaaggg catgaaaaac   2460
taactgctag ctttcctttc atttcaaaag tccaagaatt tctagtatat ttggatttta   2520
gcttctgttc aaagcaaatc cagatgcaac tccagtaagt ggcctttgct ctttttttgta  2580
ccaaagagcc cagatgattc ctacagtccc tttcttctct aacatgctgt ggttccttaa   2640
atatgagtaa tttctctaag atataaccca ggtgctttga gaagctgcat taaggtgttc   2700
aggccctcag atatcacatg gtacacttga ttagtaataa aaccagagat caatttaaat   2760
tgctgatagg tcctgtctca gtgtgtggca ttgactgttt tcaggaaaat agatacagat   2820
taatatgagt tatgcgtgta ggttgtgtat agattgagaa gatagatact tctcaatcta   2880
gtagtttgat ttatttaacc aatggtttca gtttgcttga gcatatgaaa atcctgctta   2940
atgtgcttaa gagtataata aatgtgtact tttgtcctca aacctagtag ctgggtttta   3000
acactcatgg acatggtctt aatcaatgga gttaaataaa caaattcagc aagttattaa   3060
atctgacatg gtaggagagg ggagatgtgt cctgcttatt aaatgtgttg gtccattgaa   3120
agttacatgg attgccaatt tttaaaacac taaagttgaa taaaatgcat gaacaataga   3180
aaaatgctga acattatttt ggatgctagc tgcttggaca ttaactgtgt tatttctgct   3240
ttgagatgaa aatatatatt tatctttgct tattttatcc cagatgtgtt ctgaatatcc   3300
ttcttcataa atcatggaaa actcactgct gagatagtaa accatgaaat cgcctttttca  3360
gttggtgcca tgtatctgac agttccatct tggaaggttt caaaattacc ttttaaaatg   3420
atctcagaag tctgtagatt ctcaatgata ctgaaagctt tgcacctctt tggtagaaac   3480
caggtctatt tagaaaatgg ctttatgata aatgttgcct cctgagtgat aatgaagtgt   3540
tcctggatat tgtattgtaa tttaatgtgc ttaccacact gccacatttt aatgagtcag   3600
agaaaaatta atttttcttc aatacaataa tagaacaagt agcctattct cttaaaaagt   3660
atgtgaaaag aaaattatga aaaaatatgc atacctaatg aagtattggt tttagtaaga   3720
attaaataca tttcattgag ctttaaagta ctttggagaa actttggggc acgttttcct   3780
actctaattc aactaaagtt ataaataaag agaaaaactc attcagaaat catggatttt   3840
aaaaatattt tactgcagcc aagttttcat ttcaaaatgt aatttcagtt tggagctttt   3900
aggcattatg tatatttaaa aaatatattc ttcaaaaatg cattttggca tggtgggatg   3960
gatgttgcaa aagatatccg gagcctccag tctgtcatta actgatatgg taaatcacct   4020
ctcttctttg ggtctcaatt ttttatttat ctatatggta aactcagaga tcactcctta   4080
ggggtgagtc ctattgcaat atgaccgaca aagaagacaa aatagcattg aaactaaccc   4140
atacaaaata tccaactctg gattctgtga ataagtatct tgaccataaa aagtcattgc   4200
tgttcttgtt tctaatgtaa atagtgtcca ttagtaaaag tgaaattcag tcttaagtag   4260
ggtgaattgg atcaccattt acacaagaga tggctttttc ctttgcttga ataaacattt   4320
tggatcacct ccaaagaatg aaaaccagta gtacgtttta gtcatattag tcaggatgag   4380
aaactataag atgtgtgtaa catttggaaa tgcaccaaag tgagcgttta aatcttctca   4440
ttttattgaa aactaagagc agaaaatgta aaatgctcat gaaggttttg aatgccaaaa   4500
gatattttag aatcaattta taaaggggta attcattaat tacactttaa aattggaaag   4560
```

-continued

```
tgggataaga aatctaaagt aaaccagctt atctttgaaa caatattatt ttgaaattgg   4620

ctttaaaata aaaccattca gattgaaatt ctaattagct catttgtgga gtttgatcac   4680

acaattcata atgttgctgc tttccattaa ctagtcttga aatgcctttg tttgtaaaaa   4740

taaaataatg gtactttcat tttataacaa ggtgtttttt tcaagaaata atccatgcta   4800

aaatggatat ttgtgatcct gaaatgttta ctaagcattg taaatttatt tataactgcc   4860

atctccaact acatccttat gatgttttta acaataaaat taaaacaact gttaaactaa   4920

aaaccacacc gttttccagt acttgatctc tgagctacaa tactcactaa atataatttt   4980

ccaatcaaaa tattctattc tatattctaa gggttaatat gtgattatag tgtccacttg   5040

ccaccatttt tttaaatcaa tggacttgaa aagtattaat ttagatggat gcgcagatat   5100

accctcagtt cagtcataga ttggagtttg catataataa tgtaaatgta tgtcgacact   5160

attctaaata gttctattat gactgaaatt taattaaata aaaaaggttg taaaatgtga   5220

tgtgtatgtg tatatactgt atgtgtactt tttaaaatag gtgtatgtcc caaccctttt   5280

ttatacaggt ttgaatttaa aattacatga tatatacata tactttattg ttctaaataa   5340

agaattttat gcactctcaa aaaaaaaaaa aaaaaa                             5376
```

<210> SEQ ID NO 6
<211> LENGTH: 245
<212> TYPE: PRT
<213> ORGANISM: Homo sapiens

<400> SEQUENCE: 6

```
Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Gly Lys Ala
                165                 170                 175

Lys Asn Pro Pro Gly Asp Ser Ser Leu His Trp Ala Ala Met Ala Leu
            180                 185                 190

Pro Ala Leu Phe Ser Leu Ile Ile Gly Phe Ala Phe Gly Ala Leu Tyr
        195                 200                 205

Trp Lys Lys Arg Gln Pro Ser Leu Thr Arg Ala Val Glu Asn Ile Gln
    210                 215                 220

Ile Asn Glu Glu Asp Asn Glu Ile Ser Met Leu Gln Glu Lys Glu Arg
```

225 230 235 240

Glu Phe Gln Glu Val
245

<210> SEQ ID NO 7
<211> LENGTH: 94673
<212> TYPE: DNA
<213> ORGANISM: Homo sapiens

<400> SEQUENCE: 7
agaatactct gtgaacttat tatgtatttc atcattttca aggctggtaa aatcacacgc 60
cttcacatag gcaaagagaa cttcacattc ttgtagtttg gaaactccat aggaaggaga 120
tactgttccc cattagctca agcacaaaag tcccacagtg gattctgatt ggcccatctc 180
atgtgatgta cccattcctc caccaatcag gactggacag atcagggtac taagcctatc 240
tccgatagtg gaaggaggtg ggaaaacaga accatgtgaa tgacagtctc tcttgaaaga 300
taaggaatag tctgaattct ctaagtgaaa gtgagtgcta ataatggaag aagagtgaca 360
ggaaagtgtg ctaagcaaat aaaaaaaaaa aaaatctaag ccgggcatgg tggctcacgc 420
atgtaattcc agcactttgg gaggccaagg cgggcagatc acctgaggtc agcagttcga 480
gaccagcctg agcaacatgg agaaaccccg tctctactga aaatacaaaa cttagtcagg 540
catggtggtg catgtctgta atcccagcta ctcaggaggc tgaggcagga gaatcgcttg 600
aacctgggag gcagaggttg cgtgagccaa gatcatgcca ttgcactcca gattgggcaa 660
caagagtgaa gctctgtccc cccccgacaa aaaaaaattc ctaaccacag tccatatgtc 720
taggttagat catggttttc ccatttatca attgagggat cttgagcaaa tcaccatact 780
tctttgatcc tcagtttcct tatttatcaa gtagaaaagt taaaaattac ctctcttaca 840
tgattgtcat aagaagttat tgacagaata taaactaagg gcttagacca attcctggct 900
tatatgggca acagcaacct aattgaccaa tatttaaggg attcgctctg ttctttcccc 960
tgtgacagat attgacaata aaataatgag caagggcagt cataattact ttaaccaaat 1020
agtcaaacaa acaaatacaa aactgcagtt gttttataaa aaataggtaa ttcatgctcg 1080
actttatagt aagaggagaa ttgaacaaag caaagagatc agggaaaacc tccctgagga 1140
agaaaatata gggaatactg agttgagatc tacatgataa atgcatactt actgggcaca 1200
atgatagggt gaaacaaagt ggtccaaaca gaggcagaaa ggagggtatt tgcaaatggc 1260
ctgaggtgag aattatgagg acagaagggc cttggccctg gaaaaaaggg agcacataat 1320
gaattgacct tggagaagga gggagaggcg agatcctgga ggccttgaag gctttgctaa 1380
ggtgctaatt tctttattcc aagagcaatg gcaagccacc aaagagcttt cagcagagga 1440
aatttcatga tcaaagaggc attcttctcc ttttccccct cctctagtca ctcaaagaca 1500
gatatagaca gtctgtctcc ggtctggctt ggtcaggcaa taagtttcag tttgtgagag 1560
acatttttta aaagaaaaat attgaaaaca atatgtgtgt ctaaaagaag atatccacaa 1620
aatagtgaat gaacaagaga tatttcacat gcacaaagca agataagact tatttggtaa 1680
attacacctg cctcttaaca acaaaaacga taaagctcag gaaaaaagct tttcaaaatt 1740
ggattaatca ataatagcat gagtgacgaa tagtattgaa agtattcaag taaaaattag 1800
ataatcatga aataactttc tacccagtgt gttaaatgtt gaattccctg agttgtataa 1860
tggtagcctg ctatttccat aagaaaacat cccccatccc tcctgtccac ctgggacata 1920
gccctgcctc ttgttcagtt taaaggaact ccttggtttt tcttctgcga atcaactgaa 1980

```
tgctggcctg catcccctat caaaagccag tcttaaggag agatctcagt cattctgacc   2040
catttgtgac ttccatataa gcctacccaa aatctttcat ttgcatatta gctctttcta   2100
atcccttgga tatttgcttc gacattctct tgattcaagt aacattatta cacaacaaaa   2160
ctgtaatgca gcagtatgag ggaaacaaaa gatacagtta cgtatgagaa agtcagtgat   2220
attaagaaag ctagaaccag ggaatggtgg aggtgggagg aggagacaga actgagaggg   2280
aaaaaaaatg gaaagaggga gaaagagaga ggagaatgag aatgcattgt aggagatgaa   2340
cgtagcatgt attattgagt tgaatgaaaa gaaattgaac tgaatttctg ttaggaacac   2400
tgccttgttt ctttaaacct ggtacaacaa attaggccat tcctttctat tggtctcata   2460
aaatccgtat ggttagattt atgattccca ggcttcagta actctcatac cattttgatt   2520
atttttgtcg tatctgtcct cctttagtac tacttgttat ttacttaatg ttatacatga   2580
aagtgagttt atattgacac taaatatttc ttttcttggg gggaaaatgg tggtaaaggg   2640
gtacaaagtt ttagttagac aggatgaata agttctggag atttattgta cagcatgata   2700
actacagtta atgtactgta tacagttaac ccttgaacaa cacaggtttg aactgtatgg   2760
gtctacttat atgcaatttt tttttcaaac tcagatggaa aatacagtgt tctagagatg   2820
taaaacccat gtataagcag ggctgacttt tgtgtctgca cgttctgcag ggttgactgt   2880
gggacttgaa tatatgtaga ttttggtata cctgaaaggt ctaggaatca atcccctgaa   2940
tatactgagg tactccaaaa ctacaaagag tagatgttaa atactctcag ctcccaaaaa   3000
tgatgagtat gtgaggtgat ggatatacta tttagcctga tttaataatt tcacaatgta   3060
tacataagca gaacatcaca ttgtacgtgg taaatagata ctatttttgt caaatataac   3120
ttaataaagc tggagaaaaa aaataaaatt ctccacttca aaaaagcctt aaaggggccg   3180
ggtgcagtgg ctcacgcctg taatcccagc actttggaag gctgaggcag gcggatcacc   3240
tgaggtcagg agttcgagac cagcctggcc aaaatggtga aaccccgtct ctactaaaac   3300
aacaacaaca acaacaaaaa tacctgggcg tggtggtggg cacctgtaat cccagctact   3360
tgtgagactg aggcgggata atcgcttaaa cctgggaggc ggaggctgca ttgagccgag   3420
attgcgtcat tgcacttcag cctgggagac agagcgagat tccatctaaa aaataaaaaa   3480
taaaaataaa tcttgaagaa aaaaaaaaca atcatttgct atgcctccag tatccaaatt   3540
aagctcattt tgatatttga tgttcgatat atttgtacta agagtaccta atgtataaaa   3600
atctttctaa gcaactatca acttggaatc atgattgatg tgctgtctat acatattttt   3660
tctaacatga gaaagtgaga acgcagtccc ccactaaatt atgcagtcga gtttcccaca   3720
tttggggaaa tcacagaagt cagcacatct ggagtgaaat aaacaagctt cgccctgatt   3780
acaggtttgg catattcatg tttaacaaac gcaccggaac taattaaagc aaatttggac   3840
tcctactcta ttattaaaat aactaattcc taaactcata cattattctt tcttttaaag   3900
atcactgatg ttaatgttca gctaatattt tcttttaaaa aattaatgaa atgctttgga   3960
atgttctcca gttatacaaa caaaaacaga cacattctgg agaatcaata aaatatttga   4020
agtatttttt aagactgtac agctggagct ccaggtttaa attagagctc tgccatttac   4080
tagatatggt tggtcaagaa aattaacctt gtatttcatc gtccataaaa tgggaataaa   4140
ataataagat ctacactaat agatttgatg aaagaattta atgagataat ctatgcgaag   4200
ttcttagtct ggcacctggc acatgaataa gtgcatcaca taatgatgtt agctattatt   4260
attgtggttg cattatcttt ccgttcaaaa aagtacaact ttcaaagcct tgctgtgttg   4320
gcgacctgta gtttaataat ctatcgcttc tctttcaatc ttaatttcta aagacacagt   4380
```

```
aacaaaccat tccaaatgaa gcgtctcccc ttgcaatact taaccttgag tcaacaattc   4440
ttgtaattat taaatattca ttcactaaag taattgtttt ttttaaaaaa tagaggtgat   4500
aggacaatgg cctaactaca gatcgcaatt aaactttatt tctctaaggc aggcagggtg   4560
aattctttgc tccgaacctc ccggactcct ctccctctcc gactttgtat aacagaggga   4620
gctccgagcc ctctctggcg cgcgaggtat ttcgtctgtc cccgggggtg ccaggtgagc   4680
cccagcggat ccgggagggt aagctgggac tcctcgcgag cagtagctgc agggtaccaa   4740
gcttcgccct ctgcgtcccc gcgccttcgc ggtctcccgc cagtgcaggt ccggggcccc   4800
caggcgagcg gacaaggttg gcctaatctg ccaaacttct ggggcattta ccgtgctctg   4860
gccgccctcc cgattcttcc ctccgcgccc ttgcctgctt ctcgcctacc ccgggctccg   4920
gaagggaagg aggcgtgtcc ggagcaggcg ggcgggaact gtataaaagc gccggcggct   4980
cagcagccgg gcttcgctcg ccgcctcgcg ccgagactag aagcgctgcg ggaagcaggg   5040
acagtggaga gggcgctgcg ctcgggctac ccaatgcgtg gactatctgc cgccgctgtt   5100
cgtgcaatat gctggagctc cagaacagct aaacggagtc gccacaccac tgtttgtgct   5160
ggatcgcagc gctgcctttc cttatgaaga agacacaagt gagtagggcg cgcccgggag   5220
ctcccaggct ctccaggaaa aatcgcgccc ggtgccccgg ggaagccggc gctccctggg   5280
acttgcagct ggggcgtgca gggctgtgcc tgccgggtga gacaagagga tgcgggggag   5340
gccggcgtgg tgtgtgatcc cgagccgagc cgggtgagcc agggagaaaa ggagtgggag   5400
tgctgagagg gagccagtgt caagtttgga gcctcagcag ttaagttttg agctgtcagt   5460
cggaaaccgt aattcccgtc tggtggaaag attggctttt gggccatgga atgttaagtt   5520
atcacgggaa ggcatgtctt tgcataggag acggttttcc cgtggattcc aggagattat   5580
gaaacagcac cccacgcgcc accctcacta gctctctcac tcagatttat ttgtgtagcc   5640
ccgaggtggg cgccgggcac caggagcggc gcgaacgcgg gtgcagccgc gggagcgaag   5700
ccaacgcgga actcctaagc ggcagctctc ggcggggcgg gaacctgccc gcctgcccgg   5760
gaaacttggc tctcggcggt gtctgcctag tttgcagctc tgtgtgggct ctaaagagct   5820
ctagtacctc cacaatgcac gcaccttttt ccatttcaaa agggataaag gctttttata   5880
aaataggcac ctctgaatga tagtgattga gataattccc agtgctgcta aattctgcat   5940
tatacataaa gcactgtggg taaagcgctg cctgggggga caattagatt tttttttccc   6000
ttgaagaaaa tacctggttc ttcgtttaga aagggccgcc acggtgcccc tatccacagt   6060
tctcttcacc attgttgatt gttacctcct ctcactttcc cccttagaaa ttgttatgtg   6120
ttatctgccg cggttggcta agggttgccc tttcaccccc cagaggttct gttggagatt   6180
gcagttcctg aaatgtgtgg aaggggtgga agtggtgggg aaaaaggaaa ccggggtgtt   6240
tgtacacatc gttggtgtag aatgaaggca tcaatgtgct caaaatgctt tatcaaatga   6300
cctgcttagc atcatatttt aaacagatat ctaggcctgc aaaaagttgc aagactctag   6360
ccccttgtac cggtgtggta aaaggcaggg gaaagggaca ttgcctggct aaaagaggct   6420
tgcatagtct ctagagcact ctctaagaga aaagacgcga tgtgcctctc ccctctctta   6480
caagcaggtt agctttcagg caaggcattg agcaccgcac ctggaatcac cacagcgtgc   6540
tgtcgaaatg caaatgttaa agattcttgc aacaaaagaa aagttttatt gtaatctctt   6600
gatttagaca agctttctgc gaaattataa gaagggtaga gacctattcc ttcttatagt   6660
agcatctgct cccatggatg gtggtgagat ctgggggaag aagctgctac cttctagttc   6720
```

-continued

```
aggaaaagag cctaaacctt cctatttaaa caagaacaca ggagacagat aaggttaatg   6780
tccaacactc caaagccagg ggatgtacta tcaagtcact ttgagaggca gtaggattga   6840
ttatccttgc acccttgctt tgcaaaacaa atgtgagctc tgtaatctcc tttctcgctt   6900
tgattaaatg gctgtgtaaa tcggattaca tggaataatt ccattgaaaa ctagaaagag   6960
gtcaatctag tctgaaacat tgtgactgtg gcattagtga ctcagtgctg ccgaccagag   7020
aaatttgaga aagctaagta ttttagatat gtgacctgtt cggtcacaca tcacacaagt   7080
taaagtgcag gccctttggg ggaacttgct gatgttaaac ggcttgtagg caaaggaggg   7140
cagtaccctt gttgaatgaa ggcattcatt gcctaggatc taatgacctt caaggttttt   7200
tttaagaata cttctagcga ttccacagtc actgaaaaag gggacactgg aaatagccca   7260
aaatcaataa aataatctgc agaaatggag gaggggatta gatctttcat attgttaaat   7320
tttctaatcc aaaaattaca aagacatttt ctgtgcaatg ctgcatggat ggaaggtagc   7380
ctatgtaaat tggacattaa gaaataggat cgattgttct gattctaatg ttatcctcac   7440
cagggaagaa tatctattaa tatttagtag tttaaatagt catttataaa catggcatca   7500
ataccatggt tctattataa agcaacttgt tctgtactct cctactaccc cacatataaa   7560
aaaaatttat agtaatattt taaaatgggg tttgatttga attacacagc tctccaagaa   7620
tcatggggac tccaggtatt ctggcctttc cgtcaagcta agtaagtgtg aaaattccat   7680
caacaaccac ttggggtttg atgaatgatt cattcattta gcatgttggt acacttcagt   7740
atttccaata taatgacaca ggcaataaat ttaagcacag ttctacagaa atgaatgtct   7800
tttgaatttt tcagatttct gtttgatttt attttattca gattgtgtgg ttttacagtt   7860
ttctagaggt gtttgtggct tgggcttaga aaaaacatct ctttcaatgt gtaactattt   7920
tttaaacata atattctgat acaccatatt ggataacaat caaggcacca tattttgcaa   7980
cactgattaa gatttggtta aaagtgccat tagcttaatg tgcctggtgt tacatttatc   8040
aatgttgtgc ttacatttta gtttggggat ggtttgtgag aagtgtcata actcctgtca   8100
atttcagaaa tactgagata agaaagattg atcttgcaaa caatgtaaaa aaggccattt   8160
taggcatact aactctcaga gaataagcaa atagaatgct aattttcact actccaaaga   8220
aaatatctct tttatgtctg tatgaagttt gtcatgtggg tgatgatgca agtttacttt   8280
gtagaagaaa attaacatac ttatgaaaag agcatttttt tagtcttgtc cttaagatca   8340
ctcaatttgg aatgtatgct ttgaataatt ccaatttatg tagcttttaa ttgatacatt   8400
ctgccaagac tttaaaaccc aagtgctaag ttgattacat ttaacataaa acaaggaaaa   8460
taaccatatg gaaatctgaa agtctgggcc aaaccaatta aaattgctaa attttattta   8520
cgtctaactg ctgatttgaa gatagcaaat tctgggtcac attttttttt taataatagg   8580
tgactgaaat gtttccatca ccataaatca cataaaaatt tctcactcaa atagcaagtg   8640
tgggtattgg aggtttttta catggattgg caaattccac tacatgtggc cttcgcttta   8700
tatctgagaa taaaccatat ctgagcatat atgagaaaca cctaaaatat ggttggtaga   8760
aggattctag gttctagctt ctgaagactt agattctaat tcctgtttta ctactcatga   8820
gacaaatgac cttaggcaaa tatttgttaa actttttggg atttctgttt tttgtaatct   8880
gtatgatgat tataaaagtt ataaagattt ttctcgcatg gtggttttaa ggactaaatg   8940
aaattttata tgtgtcttta taccagcata gtagcttact atatgtacag tttgaattta   9000
ttgttcctga gaagagagtg cctgctggcc tacttttaca agccagagaa aaactgactt   9060
attgcaggta aattatgcct aatgaaccaa gcacagagac caagttttcc taaatctacg   9120
```

```
tctgtcgatt tggtgactcc catgataggc taatatctgt ttatagacta taattaagac   9180
acatcaatcc aggaatatgt gaagacaaag gtgatatgtg ggcttaagag gtgctacgtt   9240
tttgaaggtt tttcttttaa agtacaaatg aatgagataa ttagaataga aaatagaaat   9300
ggaaaatgga aatattatct ttatcgctga ctcagtttca tatttctaca ctcttgctaa   9360
gttctccttg tatgattcta aggaattatt tcattttatt ttattttatt ttggactaaa   9420
gagacttggt tagtttccca tccctaatgt tctcgcactt gcttttctga gtgaggccat   9480
gcattcattt ctgtggggtg tctttgttgt ctttaccagg caacgtgcag tgacattttt   9540
ttttcattat gctagtttga gacttttatt tttcttttct ggattatctt aatgttccct   9600
tttgtaaatt atttttattc ccttttgtaa attttattcc cttttgtaaa ttagggcaag   9660
gcatttggat ataaatctct gaagagtgat cttttatctt tctttctagc acataaatca   9720
tgagcagctg caagaaactg ttcttggtct tacacactgt tcttggtctt agtcacgtgt   9780
gtagacagaa caatttacaa aacaagttga gggaacacca agatattttt ataatatatg   9840
ctgctttcag ggttgttttg tataggctct gtttcataga aacaattgac tgcagccttt   9900
ctgatttata gatgcagcaa gatgtgtttg ccttttcact taattatggg tatactaaaa   9960
actgtttaca ggggctggga gtttaagaga attgtcatga tctcatctct acctatttct  10020
ttctctatag aaaaaagagg tgggggagtg attttctcat agttggggct catggttctt  10080
tctttaaaat cataatgtgt gtcatctaaa ggaagactgt tctttatgta cctgtctttg  10140
tcctttggct acattttact atttttgtag gctgccactt tggcttggat attaggaggc  10200
tgatttcttt tattaacctg gataataagt agtagtaatt tgggaaatta tttgaactcc  10260
agatcttagt ttgctcaact gtaaaatgag taagtgagac taggtgattt ctaagtgcct  10320
tctggttcta aaattctcta tttctaaagt actagtaaaa tagatatttg aaccagatgg  10380
tatttaagct tccttcagtt ctcagattta tgcagccatt gcttcagtgt gaatgcacat  10440
tataaccatt gttttatgat tatgaataag ccaatgggga gaaatgaagg agatttaaat  10500
ttagactgtt ctacttttat gcatttcacc tactgcttga tatttctttg taaaaagaat  10560
ggtatttaca ctttcctgtt ttagcaaaat ccatagttaa agaggatctt tactttctct  10620
gttctaaatt tttaagttct atgaaaaaga attctaagat aaagtcagct aaccagagga  10680
gataagctta caaaaggtaa tgcttccctg tatttgcctg tttttttct gtccctttaa   10740
cttccagtac gtgtgtgcat ggagttgaaa tggagaaaga aaaccaagaa gggatctgat  10800
gatgtagtag aaagagcact gaggggagaa tcagaggaac tgatcctacc ctttgctctg  10860
cctcaagatg tgtgaccttg gactagtctc ccagtcttag tatctctgaa tcatgcccaa  10920
gatagttaat cctgagaaga tagtgaagat gagaggctgc agctggagac acggaggtgg  10980
aaagaggagg gagcctcagg gaaaggcagt tcctgcagat gatactatgc caaatctctc  11040
cttggctggc ttttgtctgg gtccagtacc atccttggaa cagtgcttgc ttacctcctt  11100
tccttagctg agagctggag caaacccagc agctagccgt agccctttc tttttttctt   11160
ttttttttt tcttttagca gtcagaagct atggcagtct tttcttgttg acatgagaat   11220
attccaagat cagctggacc ctcctcaagc taggagaaca cacatttctc agaaaacagg  11280
gccacaacca tgaagataat gttcttctct aatcactggc attgcccact gagctatcca  11340
ctaaaacaaa gtttagaatt gaggcaatag tctagaaaat ttaaaaaaaa aaaaaagtag  11400
caatggctat tattgggata tttggatgca gaaattcagc acttgacttt gtgcctgtag  11460
```

-continued

```
ctgttgccct ggggctcttg aatgctgctg attagaacat gggtaaattg ggagggagcg  11520
gggcaataag gtagcctttt ctgtgttcca ggtacacaga cagcagctca aactttgtct  11580
gttgctcaca aagaatgcct ttgctcttta gggtgaccat gtaaaaggac atgaaaggac  11640
caccgcaaac tcatcggtgc tcacttgaaa aagcaagcct tgttcacctt tgcagaaagg  11700
gcatccccac tgcataattg catccctgtg caaacctggg aagaaagagc acaggttgga  11760
ggggggcgtt gtgtttgtct tgtatgccca tactgtgttg ccttttcagg agcagaagtt  11820
catctgctga acataagccc tgtgagtgct tagaactttt ccctcttttt caccttgaca  11880
taaaatccct aaagctgagg acctttccct ttcaatgtct tcactctgct ccagggctga  11940
attgcatctc attattggct tgtttcacct aaatgtgagt atttgagtgg cagtgaacca  12000
ggttgcctct aaggaataca actgaataat ggtggtctat tgtgaaggaa cctcttaggg  12060
ccctacagtg ctgagttttc tactgtttac ttggagttcc tttctcagtg ccttcccaaa  12120
caactgcctt gggaaaacac acagattctt tggcttccaa gaagagtgtg acagagaaag  12180
tgtgctttgt tataaaggcc ttgtcaccct cctggatgtg ttatccatat cgatgtactg  12240
gctgttaaaa ttcatgttca ctgcagaact ctagatggag gagtggtaag aagggagggt  12300
agagatgttt tcatataaaa ttgtttctaa tgtgatctag aaaacccaag gattgcaaca  12360
cagacctcag cagtcataca tcattattta tggttctgtg taaatgtaca atttaacgct  12420
tctgaaatag taaacacatt agggatttcc ttttttgatg aacaaccaaa agctctgtga  12480
ttgctttagt ttggatttct cgcaacttta gaaaactgct gtattccgtg ggccctactc  12540
ataaatcttt gatgtgctct gttagtcaga ggactgacct tagcacattt gtcattctgc  12600
tgtttgaaag atacattatc acagtatagg agaatggctg gtgctttcta cttccaggtg  12660
gtccaaagtg ggaactaaac aaaatgaggg gataataaag ggattaggca acattcatga  12720
aaaattcaga ggaaattatt agcataatgt ttttactatt tggatgacat taattgtatg  12780
tagaaaagca ctgaactaca aaatagggct tacataattc ttccaatatc tttgtaacaa  12840
attatatata tatatatata tatataataa tgtatataat atatatataa tgtacatatt  12900
tatatttatt cttagcccct gcccagaaaa gtgtttttaa aactttactt cctgtttgta  12960
atgtactgaa gccacagtac tctatgcttt aataatactt taaaaataat gtaccttttt  13020
ttaaaatatg aaactagggt ctttaagaaa aaaatgtatt taggcattta ttaggcttgc  13080
ttgatttatt tcatatatag atacacatat gactgtagct aattttaatt taaaattata  13140
agtagcttct aataatacta gcaaatcctt atataatgct cacaatgtca ggacctgttc  13200
taagccgttt gcatttattt atttatattt ttcaataatg agacttttaa atccaagact  13260
gatttgacca tttattgttt gcacttctgt acaaatgtca cacataatga ttcaacttga  13320
agagatgaaa tttactgtac tatgtgtcaa gtgtttggca tttaaatgtg tagccatttt  13380
aaatagcttc tatcattata ttataaaatc aaaccatcct gataatagat catgccaaaa  13440
tggcacttag tagaaaacag ttccaagatt aattaattca cagcactttt ccgctgagag  13500
gtagttatta ttttttttaaa ccccatttca cagataggaa aactaagaca aggtctttct  13560
cctgccaatc ccaggtgttt attgcaaaag agactcagct ggcattaacc acagcgcatt  13620
agtgtggctt atttaatacc tcaaagatat gcattctgtt tacatgaaca ttgaatcaaa  13680
aacaaatgca actcagatgt tcaaaaaagc tgccagtaat agaatttgga caacaaaaat  13740
ttcatgattg cagttgcctc aaagagtggc tcctgccaac tgctcagtaa atacacttgg  13800
aatgttgtga aatgaatgga gacctaattc aggttgttag atactgatac attttttata  13860
```

```
agcctttttt ctaatggcaa aattttaaca attgtgctag gtctgttata cacacaaatg  13920
tgtttggtgc atgactggca aggctacttt gtttactatt ttacagcatt aattttcagt  13980
gaatgcataa catcatttac ttagtgaaac tggagacaat gtgagagaat agcaaaggtt  14040
tgaatggata tagatcaaat gtagtattgg ttctgccact taccaacccc agtaagtttt  14100
tctctttgaa cttcactttc tcaatattta aaatgggcac agaagtaacc acctagtagt  14160
agtattgatg tgataattaa aagagataga ctgtctaaca tcacagcaac tggcacttac  14220
ttaatagagc attgtttcct tctctaaaag aatagtaaat cacacagaac attatacaaa  14280
tctgtatgct gtaagaaata acttcagtgt tagtaattcc tggctttggc tatagggctt  14340
tcataaataa aaaaattaaa accaatcctt agagactaat agcttaactc tcttatttat  14400
acgttatcta tcttatttga cactcataaa cacccttagc aaatttttag aaaatttttcc  14460
caattttatc ttctttactt ttctcccctt tctgttgaaa agaaataaca aagtaggcca  14520
aagacaagct gtttaagaag taagagcagc ttactgaata aggaaatata agacaaatta  14580
ataagttaat aactgtgaat tactccccat gggtgaaaca ccatgccaca aactgcacaa  14640
gtgtatctca ttcgattgta gcaaaatgtt gtaaaataca tattattatt tggcatcatt  14700
tttttaacaa aagaaaaata aaaaccctga agttcagaga gattaagaaa acttgcccaa  14760
aatgagaatt taaaaagtgc aagtggaaga gtttgtattt gaagccaagc ctatttaaat  14820
ctaaaggcca gattccttct aatcactaca atataatgca ccaatataga cacgcatgca  14880
tacacataca aactgaaagg gttgaacttc tttgtttttt ttttgttgtt gttgttgttt  14940
tttctaattt atttgtggag aagaagatgc aatttaactt tacaccagaa agactgagag  15000
caggcaaagc tgagtcctct ggttgagtga tgagttgctt ctgaccccac actcctcagt  15060
acttaccaga agtgtaaatg gctgtatgtg agcaacactc ccacaggtca gggagcctgg  15120
gtttcctcat caggctttcc cacccatctc cccagcagtc aaatggaaac cccttgcctg  15180
actcatctga ctgttgtgag ggaatctcat tgtaaactct aaagatgtcg tcttacttta  15240
tggaatcagg aattacttca ttgccaaaaa gctttctgtc tttcaaataa agtggtactt  15300
tgttggcaga gggcagattt taaaatattt taaagttatg tttcaaaata acttcttgga  15360
aatagaaaga tacttcagaa agtactttta tcaatttgct ctgatcctct ttacatgatg  15420
ttttggaaga tggttttaaa tgtctgtgat catattagga aattatttga taataatgtc  15480
gtttatgtct ggcttttaaa gctaccagcc atttatattg tggcctttgt tttgttcatt  15540
tcttatcaat ccaactgcat taatattaaa aaaaatattt tctgcattaa tatcgcaaga  15600
ttttaaatgg gtgattgtca gcacaacctt atcagcagca tcaccttgta acatactcaa  15660
tagcagttta gtacaaatga aaatgttggc taaaaagtcc tggcatcatc tcaacacagg  15720
taaaggagac aacagaacag agatgtgctt aaccaaactc tgcagtcaga tggtctgctt  15780
tggttgccta agaacgaaaa cctcttagcc tcaatttccc catctgccaa acagaatgag  15840
caatggtaca tttatcatag gtagttataa ggataaaatg aaataatcca caaaaaagca  15900
cttagtccag tgctggacac caagaaaata ctaaataaac atttactctt gctattacca  15960
ttaaacaaat ggtaatgtaa tgcttatcaa tagtgatggc tcctttctta aagaaagtga  16020
ctttaactgc aaaatctcca ctaccagagt gaaagggaaa gttgaagcaa tttatccaag  16080
taactccagc ctcaaattca cttttgtcct gagtaatgta gttgttttta ttcttttttt  16140
aaaacaaaaa ctgaaaaaga aaaatgtgta taattagaat cacaaaagag tttacctaga  16200
```

```
gcaaagttac ttctttctat catgtgccca agatcgcggc accaatatgt ggtggctggc  16260
ttatgaaaca gattcggatt cagagctcgc attcccaagc tctttgcttt acctggaatt  16320
agggggacag aacatgagtc attcccattt tgaatcagtg agtgattgcc tacttttccc  16380
tatatgagtg aagtcatttt cagcatccat agaaatatag ccacttgtca aaagaaaatg  16440
gaaagaacat ggcttttgtg tcaaaagcat atagatttta cctctggctc ttgactctag  16500
cttgacatgg gaccttaggc aatttattta tctttcctta accttctctt aaacttctgt  16560
aaaatggaag aataatactt tgcagcttcc ttctcttgtt tcctcactct tttttctctc  16620
ccttctttcc ttgttctttc ccttcttttt tttaaaaacc tggaaataat gttatatacc  16680
taatttgtaa tcacgattca caatcactca aataattgta ctattagaaa acaatgtttt  16740
tcagaattaa cacggtttcc tgctctaatt ttaagaagta aattatattt ctcaaagtgt  16800
ttggctcatt ggccttgtgt agactggaag aagcatgggg tttggagtta gacagaatga  16860
gagttaaatc ttagctccac tattatgatt acaacatgat atttatttcc ttcctctagg  16920
ccccaatatc ctcattggtg taatggggtt gtaggggtaa tagtacatag ttggaagaac  16980
acaagaatta aatgagatta tagtctgggc atggtggttt atgtctgcaa tccaaacact  17040
ttggaagaca gaggcaggag gattgcttga gcccaggagt ttgagaacag cctgggcaac  17100
atagtgagac cttgtctcta caaaaatatt ataaataaaa taaataaata aataaataaa  17160
taaataaata aataaataaa tgagataata tgtggaaatt gtctgaccca gaagtgatgc  17220
tcaataaatt gtatctgtaa gctttaggga atggattatg ccagcagaca catcagtatg  17280
tattagactg tctgctctgt gtctgtaagg atgttgacac atgttggcga cctcacaagt  17340
tgtgaaagtc aagagagtta attaactgag cagtgctcta catactatac tgtccattca  17400
gaggcctagt gttgttgtat tgttctcaga cttgagcaat aaaaaatata aattttccaa  17460
gtacatgaaa actttagttt attaatgtct tctaaaatga gcctcaaatt agtttttgta  17520
tagtatgatc atgaatagct ttggagactc ataaatctgg aatcatctct tcaaactgta  17580
tgactttgag tcacttgatt cttcggataa cattctgatt ttctcacttg taaaatgagg  17640
tttataatag tgtctaagtc ctaaggtgac tgtgaggatt aaatgagcta atgcataaga  17700
agggcattag gacaggtacc agaaaacctc ggtaaatgtt agctcctttc aaataaaatg  17760
cagttttgca ttcaaaggtt gttcgtttgt tgtttttatt ttttttgcat gtgttgaatt  17820
taataacttt atagaatcaa cagtttggaa atgtttccat tatgaattca ggttttattt  17880
tcttgtcagt gactctgttt agtttaaggg cttggttgtc cagattcatc tttgagtaag  17940
ttttgtatca atcaagacag atgcaagtta cttttatcag tccattactt caggtaaaca  18000
agcattccat tctttgacag aacattaaac tgttatgttc tttttgatgg agtgctgatt  18060
tgttcaaaac acttgtgaaa gagagaaaac agctcctgtt ttataactct tttgtaatac  18120
aaagtttgtt tccaaaggtt ttctggaagt ttcttgattg aatctttgat tgtggatacc  18180
acagtgatta atttaccaag ccggaaaatg tgggaagtaa ttttgggttc agttcagagt  18240
gggatctaac acaacacttt gaaccaatat taaaatgcag aaatctcttt tagatattga  18300
aaaagaaaaa caaatatata tatattaaag tccctgcttt taaggcctaa aggagaatgt  18360
agtagaaaca ctgacatgtg taatttttgt gaattgctta ggaacagaat tagatttaaa  18420
aaggaattcc ttttgcactt ttccctgaag atttgtgtcc tagcatttga ggagtaatac  18480
aggaaagtca gaacaagaac ttactgacag cgcaggagat ccatgtccta aattcatgta  18540
tgtggtactg tattgctatg cagctttcag gatgtccatt ttattgtcca tcaaaatgta  18600
```

```
ggggtagatc ctataatttt aaaggttctt tctaatgcac acaatctaga gttattaaca  18660
gaagtctgac tgtgtcatta ccctggctaa aatcctctac cgactttaca ttaccctcag  18720
gataaagtcc aaaccctcag cacactatac aaggtcctct gtggtttggc tgttgcttat  18780
ctccaccact cccgagtggt aagtttcatt ccagcgtcac ctaactatgt acaatgacat  18840
accaatattg ctgcacttgg tttccaaggc cctgagggcc tcgcatttgg gtagctttga  18900
tggtctctac tccaggaagt cctccctgac ttttgtttgc tctttttcct cagcccctct  18960
ccctactatg ttgtttagtg atcttaccct gagctcctgt agcatttaaa aaaacaatca  19020
tatcacttat cacattatat tgaagttatt tttttactta cctagctaag ttgtctaaca  19080
ctggtatccc tagctagtgg cacagtgcca aaatattgat aaaggttttc tgaactaaac  19140
tatgaattta atgccaaatg tctctttgag ggacaacatc cacctgtcag cattctaaga  19200
atggatccag acatttgaca attttgtgcc tgctgacctc agcagacaca tgaaactgca  19260
tgtaacactg tcctgtataa acatacatac attgttcaaa cagaattttc ctcagagaga  19320
gaaatgataa atgagccact ttgggtggta gaagagaatg gagacagtaa attaaaaata  19380
aataaataaa taaaggagaa ggtgaggcca ttgcttgcca ttcttaagga aatgacacaa  19440
taggctgaat gacaagggcc agttaaaact cgctaatgcc agatatatga agacttaaga  19500
accagaaagg attttagggc agaatattgt tgatgatgat gaagaggaaa aatgttgatt  19560
tccgatgctt attctctgtg ccaggtcctg agctaaatgt gttacatact ttatgtctcc  19620
tgattctccc cacctgtgag ggtggtggta gtgtgattat tccatttgat acaagaggag  19680
gaatctgagc tcacagaggt tgagcaaatt tctcagcatc ttacaactct cagtcatcaa  19740
acctgatctg tttgttccta atttcttgct tagtattagt actgttgaca ttttattttc  19800
tcacctagag attttgtttg tttgtttctt tgtttgttta aatggagtct cgctctgtca  19860
ccaggctgga gtgcagtggt gcaatctcag ctcactgcaa cttccgcctc ccaggtttaa  19920
gtgattctcc tgcctcagcc tcctgagtag ctgggattac aggcacgtgc caccactccc  19980
ggctaatttt tgtattttta gtagagatgt ggtttcacca tgttggccag gatggtctcg  20040
atctcttgat ctcgtgatct gcctgcctca acctcccaga gtgctgggat tacaggcctg  20100
agccaccgtg cccagccgag attttttttg atacataata attcatgaga ctattacaaa  20160
tatggtaaat ggattcttcc ttcccagctc acccacactc aagatgcttc ctttaaaatt  20220
ctgttaacaa tttgtgctag ttaataggta gctagtgcaa tactcaagta aaggatgttg  20280
tgtagttttg gatactgaga tgtatagtct ttgtctaaaa ggagttgaaa gacagaaata  20340
tgacaatatg agagggttta gatgattcta ttagaatgat atttatgtat ttaaaacaga  20400
tatggttaag gagttcagca aaaataatgt ctcaatacat aagatcagag attaagcgtg  20460
gaggaagaaa gttggagaag gattaacaag aagtgatgtt ttcaaatttc atgtgtggtt  20520
agaagccatc atcttagtga ctcaaggcag taatactact gctttacaat acagtgctct  20580
aaaataatgt tacagatatt gcatgtactt ttaaaaacat atatcatttt ggggatactc  20640
tttgatgcca agtttaaaaa attctgaagt gtttaaaatg atacaaactt agagcatgat  20700
ctgtgttcct ttttttttta atcaggtaag cttcttggtt ttgggtgtag atctgaaaag  20760
ttaacatttc ttgaaccaat aaaatgtttc cagttttata taattatatc acaaagtcta  20820
ccttctgcct tgatttgcaa agaaaagctc caaaaaggac cataaagaag aggagataac  20880
acacaaatgg tgagcaatga agtagatgta caaaatggtt tgtgcagatt tggcacttaa  20940
```

```
aacatacagc agccgaagta catcttaaat ttcatttagt gaatatattg ctcacgagtc  21000
cctctcttca tttcctgagg aagtagatcc ctattctctc ccatatggtg agaaaatctc  21060
tttgctatcc agtttccctg tttacatttg ttcttccatc cccttctgat tcctcagcaa  21120
agcagctgct ttgaaaagaa gctcaaagga ttaccttgaa atggttaccc actctccccc  21180
ttttctgctc caagaagaaa gtttctttct gtattttccc agcattatta agagtcaaga  21240
cttgaggcct taaggtacat ttcctatatt cttcttttgt tttaaacttg aaagcaaaat  21300
aatcttccca agtctaccat gaggatgaat ttcagaatgc acaataactt acatttaccg  21360
agaaaactgt taagtcagaa tcttctaaaa tagagataac aataacaagt gtgatgccag  21420
tactcctatc ctgatacatt gtaaaaaatc atctccttcc ttactgtgtc ctacatcctt  21480
ttttcttttc tttttttttg agatggagtt ttgctcttgt tgcccctgct ggagtgcaat  21540
ggtgcaatct tggcttactg taacctctgc ctcccgggtt caagcaattc tcctgcctca  21600
gcctccctag tagctgggat tacaggtgcc caccaccatg cccagctaat tttttgtatt  21660
tttagtagag gtggggtttc cccatgttgg ccaggctggt ctcgaactcc tgaccttagg  21720
tgatccgccc accttggtct cccaaattgc tgggattaca ggtgtgagcc actgcgcccg  21780
gccacatctt cctttcttaa tgaatttaga gtctcctcct acatcaaaat ggtattagag  21840
agaatgctaa ggataattcc atggatctca cgataaacaa ttggaataaa agagcttgcc  21900
acttagtcat gattattagc atgaaaatgt gatgatgcag cctattttgg gggagggatg  21960
aagtgtcatt gaatcagctc atgagtagtc tggcatgcga ctttctgttt cttgcaaaca  22020
agttgcatga taggggaaca tcaacactat gccagtgtgt ccctgaagaa aaggtagctg  22080
gttttgtttt ggtcaaagta ggaatgagtc tggaaaggga ttcagtttta tgaacattgt  22140
tttgcctgct ttagaaaaga tgacagatag ataagagtca accaatgctt tgggaagaga  22200
taagattagc atttaaaagc ttaacccatg tcatcacttc tgggtatgtc ttccctgagt  22260
gaaatcttat tctttgcatg cattttgaat gctgaatcac catgaataat ttttatgaat  22320
ggctacttta gaaatgttaa tggattgcaa ctcattgggg aaataaaaaa tttatggttg  22380
cgtattacaa taaattctaa ataaagcagt atatggaatt gttgacttct cagagacttc  22440
cagtgaactt actgcaggac agtgtctaca tttcagctct gtgtgatact ttcagtgttt  22500
tcgctttttt aatatgcccc tttttgtcaa taaaggaaag aaactccact ttatacttac  22560
gtagtttctt cagaaaggga gctctgggga ttttatagcc aggtcagccc ttcaattttg  22620
ggccacatct accaggagaa gcatttttca atgattgttc attcattaaa attgtctatt  22680
tacgttgtcc ctgcccttct tggagcttgt agtctactca tggttttata gcctagtttt  22740
ccacttacat ggacctaggg aagtattaaa ggtacaaaga aaatggttaa aagttcaaac  22800
tgagaagcat ttagctaatc gtcactattt gaatttagaa gttattgagc ctaagagtga  22860
gaaggatgac aatggtttat acccaactga tgaacaaaac cctcctgttt atccttcact  22920
cattcattct aaatatattt acgaggggct tcttcacacc tgccattgcc ttagtcagtc  22980
tgacaaaaca gggagggact gaaagtccat atggcacctt atggtgctca cagtcaagtg  23040
taagaaacag ataataagca aaactggttg gcgatgttgc aattctattg tgtaaatatg  23100
gaaaccagct gctgaggatt gaattgtaca ttgtccagcc ttcatctctg ccccattata  23160
tgtacctggg tttattctct agtaacacaa tttagatagt gccagtacct tggtctgtac  23220
catataaaag agaattttat tgaaggagaa cttttatgag caattcagta gcagttagca  23280
atacatacaa tccacaaata tggaggatta tgtactatga gaaaggacca aatcaaggtg  23340
```

```
ctagaggtaa gaatgacgga taagaataat ataatcctca ttcttatacc atgtatattc  23400
ttgttgggag gaacagatga taagagtaaa ctaattgggt aatcaaaata atttctgaga  23460
atgaaaagtg cttaagggaa agcaaaactg tgatgtgatg tgatgtgata agaggtgctc  23520
cttaagacag gttacctggg aaggcttctc tgagaaggtg atatttgaac tgagtcctga  23580
atgatgagaa caacttgcca ttggcaaagc ccaaaaagga gaaaactggc agcagcaagt  23640
acaaagggct tgaggcagga attaccttcc aggtatttca ggaacataaa ggaggccagt  23700
gtggctagag catggtggga agataaaggt tactaaggcg taaacatgga gttggacaag  23760
tctgtcttcc gaaggtctct gtaggccttg attaggagtt ggagtcttac tgtaaatgta  23820
atgggaaggc attgggagat tttaagcagg tagtgatcat gttttatata ttcccagaag  23880
aagatactat tgtgagtaat aagtctgaaa gcaaagaagg ctatttagag gatccctgta  23940
atcttccagt aagagtgtgc taagagctta gcacaagcta aagttgtaca agatgaaatg  24000
gagagaaatg agttttgaga tttattttgc tggtagaaaa tatgatcaga tgtggaaata  24060
ggggactggg aagaatcaag gatagtgccc agatttttgg cttaaaccac cattcttcaa  24120
gtttgggcat gatgttacta ggaatgcttg ttctagacag caatgacaat agccatagca  24180
aacatttata aaggtgtatt atttgacagg tactatacta aatgcccact tacataacta  24240
tatttaatcc tcagcaaacc tataaagtca gttctgttat tacacccatt tacagatgag  24300
gaaactgagg cccagaatga taaaataact ttccaacggc cataaggatt gtgtcaaagt  24360
agaaattaag atatgggcag tctgattcta aggttgatgt tttccaaccc cctcctctat  24420
accacttctc tgtgcatgag taaacacact gttttcttc tttctttctt ttttttttt  24480
ttttttttt ttttgagaca gagtctcgct ttgttaccca ggcttgagtg cagtggtgcg  24540
atctcggctc accgcaacct ccgcctccca ggttcaagcg attctcctgc ctcagccccc  24600
caggtagctg ggactacagg cgcatgccac catgcccggc taattttttt atttttagta  24660
gagacggggt ttcactgtgt tggccaggct ggtctcgaac tcctgacctt gtgatccgcc  24720
cgcctcagcc tcccaaagtg ctgggattac aggcgtgagc cacagcgccc agccaacaca  24780
ctgttttcta aagctgtttt ggatatatta gtgaagctga agttgacttt tgaaactttg  24840
ctatttaggt taacattcac ctgttgccca aacaattttt gcctcacttt tatactaggt  24900
agaaaagagc ctgcctgctt ggaagagcgg atccaaatcc aagctcaggg ggcagtttca  24960
caacctcttt atttcacttt ccagggctga tctttaatct atggggaggc agaggataaa  25020
tgagattgtt tacaattatt atgtgcaatt aaaaagaaaa cacatttttt aaaaaatggg  25080
ttgtattgtg aatgattgta tagtcattta ctgttagcaa agcttttaga atatttaagg  25140
gatcaataaa gataaaatta taactgtagc atcaactgtg gtttaactgt agctaactga  25200
actagctata gttaactatt aactgtaatt aacaaaataa taattagagc attaatagtc  25260
atgtaatgtt ctcatagatc tgccaattgg cttgtgagtg ctttacataa cattgtctta  25320
tgtaatcttt tcaaaactgc aaaaacatgt tatcatcaca agaaaactga gtctcagaga  25380
ggttacataa tttgctctgg attacaacac gtgacagcac caggatttga atccatatct  25440
tactttgata acgttctctg ttttaaatgt catcatcttc ataaacagtg agcctgcaat  25500
tgacatatat tgttatcaga agaacaagtc ctgggcatgt cattgaacct gcagttgtag  25560
agtattgtta ccagagaaat gtgtctcagg catgtcaatg aatctgcaat tgaagtttat  25620
tgttaccaga ggaacttgtc ccaggcatgc caactgtaaa tgctttgctg tgtttcagct  25680
```

-continued

```
ggtagaattg tattaaactc tcatggattg cctataaaaa attggtcttt tttaaaattt  25740
aaaataatcc ttatttttca acttgaattg tgaaacacta atgggaaatt tctaaggaaa  25800
attttgacca cccttaggag aaataaatgc ttaattactg ggcttttttcc ccttgttttg  25860
cttaggattt aattttggac aatatagtct actctgcctg attgaaacct gggatatact  25920
tcaaagagta tattgaagtg catttgatgg cctgtggaat ttttggaagg gccgtaggag  25980
cagactgcaa gctgagcttc cagaacactc ccagcactca gaacttaagt ccactacagt  26040
ctgtaaatat gttgcggcca gtgcagaaag ctgttactgc tgctgactgg agggtcttgc  26100
tgcccgcagt accaactaag ccaataaaat gcatgcccac agccagcctg tcttctcgag  26160
tatttccttc ccatatcaga tcttgcagtc acgcctaatt ggcagaaccg aagtcccatc  26220
tacaaccctg gataacttaa agggcgtctg ataaatggag tttttagctt tccagccatg  26280
atagtttaga gggatatgct aggagaatat tggaatggca attgaaagag acaatcaaca  26340
gtattctgtg cactcaatac acttaacttt tcttatcttt tttgttttta atttccatag  26400
gttattgggg aacagggggt gtttggttac atgagtaagt tctttagtgg tgatttgtga  26460
gattttggtg cacccatcac ccaagtagta tacactgtac ccaatttgtc atcttttatc  26520
cctcaccccc ctcaagttac tctaaatcaa gagcacctag tatgtagccc ttcaatcaaa  26580
tacaacgttg tatatctttt aagacatttt tgttttgttt gttttcttta acaatataac  26640
actcatgaac tatctaaaat attatatctc agactttata gagtacctaa taatcacata  26700
gagggcttac taaaagatgt gctttcctga gatgcaccct cagaaatttg gattccctct  26760
gacatgcagg aatctgtatt ttaattaaac accccagatg attacacttt catctaaaca  26820
taacacagct gactcccttg gtttcagttg gaacaccttc agtgaaagaa ggaacatttt  26880
aacagtttat tccatcccac taaaaaggca gttggtatgt ctcacacaca ttgcataatt  26940
cgcaaagcca gtttgtgacc tttgccaatc aagcttgtca tctgatgtga cagagaaaac  27000
gatcaagatt gtgaacgttc tttgagctca tgtctctagc tccactcatt ttgatgatat  27060
ttggaagcag ttaaagtaga gtataaagat ttagtttatt ctcatgtagt aaaagatcca  27120
ggttggtggg tggcgggtcg tgaggggtgg ggggaacttt gttgaaaatt ttctgagctg  27180
cttcctcaga tttttattta tttatttatt tatttaaaag gtcttgtgag actaaacttg  27240
tcagattttc agtagcagat gtgaaaatac atatgagcac attaattaca tccatagtgg  27300
gaaaaaaaca caaaaaggtt ctaggaaatt caggcattca gtctcagatt gggcacttgg  27360
gatcagatgg caactgaagc ctatgctcat ttcacatcac caaatggttt ggagttcaaa  27420
atattttaga gattttaaat aattacataa tttttgattt acatgagatc tcactttcag  27480
aagcaagtca cgtatttgaa agagtataaa ttatgattta tgtttctgta gctgttttta  27540
gagagctaca gccctcagat tcttgtacat cagggtgatg tacaaccctc agattcttgt  27600
acatcagggt agttcaattt taagagcagc tagttggcat aagagtaaac ggtgcccgtg  27660
tccatggagt gctgaagatg cagatttcag aactttcatg aatttttaaa attatgtttc  27720
catactttgg ccggtgttgg gggaggtctg ctcgtcttat ttctttgaaa atacacactt  27780
attgcagaga gttggcggta gatatataaa cctagctaac ttaaagggca tctgagaaat  27840
ggcgttttta gttttccaga cgtgatagtt gagaattaaa ctagtaccca tcagttttct  27900
agactagctc agtctgttac acatcattat cctcacagaa attagaatta gtcattagct  27960
cgcatctcct taaaattaag tggattatac tgtgtagggg atttttttcc cctctgcttt  28020
gtataactgc taaagagctt tatgaatagc taatgatcta ctttttaaac cattgttact  28080
```

```
aattagatag tctatactgc tgtcacaaat gcttactcta ttatgtacat ctttattaaa  28140
attagtaaca gtaaaaacct gaacactcag gccctatatt cttgcctgag gtaccagtct  28200
tttatcaggg atttttacac agggtcaaaa cttctgagct cacctggctc tgttaacccc  28260
aggtgagttg ttccctattc ctaggccatt taaaaaagag aaatgctgag tttattattt  28320
tagtcccact ctttcagggc tgtgtgttcc cttctaccaa gaccgaagtg aacttttcta  28380
gccctttcca tgatcactca ctctcttctt tctttttgg caaactgtag taatataccc  28440
ttgaaattcc ctcatactca ttcactcctg tagtccatcc actgtgattg acttttagtt  28500
ccatcaactc aatggcaact gccctcatta aggtcagctc cattaagtac tctttagtaa  28560
acatcatatt gacatctttt agtgcttgtt ttattcattg ccctctccct ttggtatttt  28620
ttttccattg gctgctgtac cccacaatca actgatttcc ctctcatgta tttggcttca  28680
cattctctca tctcctacac agatagttca tgatagaatg gtatctatct atggtatggt  28740
agtattcact aaggtttttg gtgataaact cccagactcc tgctgcctct tctcttccta  28800
catatctgga tcagcagata gcaccacttt ttacacagtc acccaaactg gaacctggaa  28860
gtcatttgtg cctcttcccc ttttgaccct accctctttt cattagtcac caagatcttc  28920
cgttctactt ccatatcctg ttgaacgtgt tcatttctct ccattctcac tgccactgcc  28980
ctagttaagg cccttatcat ctcagctttg gattacttca gtgacctcct aatgggcctc  29040
atgcccccag gtttgttgcc ctctctcccc cagtccatcc ttcattctga tgcctgataa  29100
accttttaac aataaatcag atcttgacac tcccttgctt aaaatcattc caggtctccc  29160
cagtgctttt aaaatgaaat ctaaatcaat tagcaaggag ggcctctgca tatctctcta  29220
gccttgcctt tttttttttt tttgcttatt ctttgaaact tattttccaa tggagtaaaa  29280
aaatcacaga attctaagaa catgccttgt ttccacactt ctgtgggcac ctgctacttc  29340
ctctctcagg ggtcttctcc ctcactaact ttgagttggc tgcccccgat cacctttgga  29400
gaagcttctc cccccagaaa ctatcagccc ctccctcaaa tgcccctgtc ccccaaatgc  29460
ccccctcccc aagtcaggtt tagctgtact tggggcaggg ggcagttgag ggaggggctg  29520
ggccttttct ctctgactcc caccactgtg ctgtgttctc tagtagcttg agcttcctga  29580
ggccagtgat catagtcttt ctgtctttat cttatgtatt tattagatac tccatacatg  29640
tctgttaaat gaagaagtgg cccctgggat aatgttacta gaagtctgaa agcacccaat  29700
tttgttttta taagaagaaa caacttatcg ctttattttt tgggtttctc ccctccctct  29760
agctatgtaa atttttgttt aagctatagc taagtgtaac ttgatttacc tgctcgactc  29820
atttattcaa cctggtaata acttgacatg taatttcaat ttgaaactga ttgagttaaa  29880
gagacctata tgccttctgt aacatgaccc tttaaaataa aatttagtag ttcattaaat  29940
ataaatgaag tcagttttat tatctaactg gcctagtatt tttctttcca gcatagatag  30000
tgtaggtttt ggtttatatc caatccagca atttcctagc aaagtggcca taaggaagtt  30060
acctaatctc tcccgaattg tgttttgctc acctgcagag tagggtaata atatctacct  30120
ggttgatggg aggattacag gaaataatat ctgcaaactg cttgtcctat gcacagcccc  30180
ttagaagtca atatattttg agttatttcc actttaagta gtatttacat gtagaacgag  30240
gactgattat taaagggtga atttccccaa atttttctca tgcattgaat accttgaaat  30300
ctttaaattc ccgttacatt aaattccctt attatattac attgtctgcc ttttcatatt  30360
aagcaacttc tttctagttt ttttttgtta taagagcata ttcattacat attttaatga  30420
```

```
tcacccatat tttaaaacat ttttagctta cttcttcaca aaagggaagt tagaagagta  30480
tctttacaag attttggcac ccaccaattt ggactccaag ttggtctgag tttcaattag  30540
ttactctggt aacatctgtt ttattgatag tagttaagtt tcaaaaacta acaaatctac  30600
taaatgtttc agttgtccct ttaagattac ttaacagtgc ttagagaaga attttagtct  30660
gtgtaagatg attaggtatt ttccttataa tgtttaatgg taaattttta agcaattaaa  30720
aagatctgaa aaaagaagtc atatagaact gaatggttat tcaccaaatg aggatcctgt  30780
tgttggttta catagattat ttttggaaga tatggttcat atgagttaag aagacctgaa  30840
ctcaggacca attaccatac ctgtatcttg gtaacttgct ttcctgtctt tgggtagttg  30900
agccagttgg ctctcttcca aaatacattt gggctacaag ggaactgcct gcttcaatag  30960
ctggtatgca ggattaaaga gaagatgaat gttgtttttg gcagcagctg ctgttttgtt  31020
cagggcagct ctaataccat ttcgtaggtc tgtgcataaa gaaaatgagc tacacaaaca  31080
cttaactctc tttttgactt tgtgacgtct gtaatatgga ccctgacaat gcatatttta  31140
aaatcacttc tcatattcat agagaaaaaa aggctttttt tctgtatttt attttttttgt  31200
ttttccaagt ttagaggatt ggtatcttct ggtttcttga acagcatatg tccccctgat  31260
attcttaggc tgcatgcatt ttaatttcta ctgaaggaaa ggaatctgca gtgtgactta  31320
tgtgttgcaa cacacgttca gattaagtcc atggtttgtt ttgggtgttt gtagctcctt  31380
ttcctggcat gtggcctttt actgtaagga aagctctgtg ttcaggaggg attggttatt  31440
gagtgaatag tccactggag tctgctgatg tttgttctca acaaaaatga aaattaagca  31500
agacctttgc ctttgaggtc ttcaacctca tcttcttgta aatccctccc accccagact  31560
tctttaaagt acttttctag tactgtctgc tactgtctgc tcccagaaaa ggaccagcca  31620
catctgtcac tgatgttaac ataaatttta gtcagtatta cttccctcta ccagaactgt  31680
ttctactgca tgccttggtt gtaacagtgc acacagattt ctcattattt tttttcctaa  31740
tcatgtaaat gatttgaagg caacatttag caatgaaagg attattggaa ttttgtgtgt  31800
tgtgggggaa taaacggggg acacttttga tgcatgtttc tgaaaacaaa aatcgagaac  31860
tacccaggac gatatgtgtc tatacaatga aagactatcc agaaatgagg ggttatcaca  31920
caatgagctt gacctagaga gaaaagttgt acaatgataa aacaaagtag ccaaagaaaa  31980
atgtcatata cagctgcaga gaatgttaac agaaaaaaaa aatagatgat tacccaaact  32040
gaaaagatac attttagagc agaagtcaca aacacaggga cattttgctt cagtgtatct  32100
ccattagggt gtgtgtgagc gtgtgtgcac acccacatat ttaggcaccc tattccctca  32160
gagtttccag aaattggaag aagaggaaga gaaaacaaag ataaatattt tgttgatata  32220
ttggaacatg tcatttaatt ggaagtcagt tgtctgttaa ctgaagctac tctaaacaca  32280
gttcagaact aagaaataaa tgaaaaaggt gtgtgaactc aaagtcagtg tcaaaatatt  32340
catgtgctaa aggtcatact ctttgtatat gggagatcta ctctataaag tcttttctca  32400
gaaagtttta ctcaaacatt tttgaagtac ttgtcttctg gtttcctagc cgatgcaaag  32460
cccataaacc acacaacaaa taattgcata acacccatag tttgaatagt ttctcatttg  32520
attcttacta ctagttcatg agatgggtaa ggcaaaaatt atttttacta tcattttata  32580
ggctgataaa tggatactca gggagattag ctgacttgtt tgaagtcaca tgggaaggga  32640
ctgagaggtt ttctggatcc atgttctgcc catggtttcc aaaagcgttt ttttttttta  32700
atttcttctt gcccttggaa acctttgttt aaacagaatc ttactcagag gcatgaacaa  32760
ataaaacaac aaaaaaagct gagctgctct gcttaaaata aagggtgcgg gccaataatt  32820
```

```
ctggcagagg caattcactt tcctcatttg gaatagcttg accatcacta cactacacct  32880
ttcattcatt cattcattcc aaaagtattt caattgagct gtgttttatt tttctattgc  32940
tgctgtaata aattaccaaa aatttagtga ctggccgggt gcagtggctc atacctgtaa  33000
tctcagcatt ttgggaggct gaagtgggtg gattacctga gctcaggagt tcaagaccag  33060
cctggccaac atggtgaaac tctgtctcta ccaaaaatac aaaaaaaaaa agaaaagaaa  33120
aaggccagcc atggtggcag gcacctataa tcccagctac ttgggaggct gaggcaggag  33180
aatcacttga atctgggagg cggaggttgc agtgagccga gattgcacca ctgcatccca  33240
gcctgagcaa cagagagaga ctctgtcaaa aaaaaaaaaa aaaaattatc ataattttga  33300
agatcaaatg ttcaaaataa ggctcactta catcaaagta tcagttggac tatgttgctt  33360
tccaaaggct ctaggggaga atctatttct ttctcttttg cagcttctag aagctgccta  33420
catttcttga ctcttggtcc cttctctcta ttttcaatgc cagcaaggac atgttgagtc  33480
cttttcaggt cacatttccc cgacccttct tccatcatcg cacctctctc tgaacagagc  33540
tggaaaatag tctccatttt taaggaccat ggggattaga ttggacccag ggaatctagg  33600
atagtctctt catctctagt tcttaacgta atcatgtctg gaaagtccat tttgccatgt  33660
gtggtgatgt attcacaagt tccaagaatt aggacatgga catctttggg gccattatac  33720
ttcctgctgt aagctcccat atgggacaca tgttgtgttc atcatcaaga gtgcaggaga  33780
ctagaaatag gcatgttagc agtaacaata tgttgcaagt aatgacctga caatctgggg  33840
gaaacaggaa aactaaggaa caaacaaatg aaacctaaaa taaattttta aaagttatac  33900
aaacaagtac agtaatttgg aaccacttgg agaagggaag ctacaactac ataactgaga  33960
tactttgaaa gtcttccttt tatttgatga acctgaaccg tcacagaaaa gcaaagttta  34020
atatttcaat tcactgttta agaaatcaaa gtgtgtgtac aatattagaa agacttctgt  34080
gtagaaaagt taatactgaa aagtttcttt tttatataaa gaagtaagct ctgcatttca  34140
gctctctcct gagtatactg atgaaggagg tgtcattact gcttggcaaa aatctcaata  34200
tttctaactt gattatctcc ctgtcctaat gtttagctat gccagaatga attctttaat  34260
tttatgaaag gtggatattt ttaatggtag caaagtatat gcaaaattaa attacaatat  34320
gaatttattt ataatggctt taaaataaag ggctttaaga aatataggtt tttcagagat  34380
atttgaatgt tcataagcta acatagattt aattttagca ttgacccagt ggatttttac  34440
aaaatgaaca aaactgtgtc tttgtaagat atttgaattt aactgatgca aaaaaaattt  34500
atgttgccct gatcaaatca ttcttcaatt attatagcag tctgtgttga tatattttaa  34560
ggaactatca aaggacatat attaaaaatt atgatgactt gaataatata gactattcag  34620
ctgtggcatg gaatatggaa cagacttgtc tccatatgct tgatatttgc aaaagtatta  34680
aagttttaga gatctgctat cgcatcacag ttctcacaaa ccatctaaca gatttgcagg  34740
agttctggga cagtgtagag gggctaaaag gacaggagtt agaattggac agacctgggc  34800
ttactgattt caccactcag aagtcaccaa acctccctgt acctcaactc cttcatcttt  34860
aaaattagga tatatgaaag ttattttttt ccttattaga tatccaagat gcttggtgta  34920
tagtaaatgt tcagtaactt ttagctctat tcatggaatt gttcccaaaa cacaaccagc  34980
atctgcattc acattccagc gctctgcctg atagcattga actacctata ctcctattta  35040
aagccacact tcctacttga gaactgaatc tcaccccttc tttcctgctc aaggctgttg  35100
cccaagcagt cccctctctt ctgacctata ttgccaattg cttcctccta ctggatcatt  35160
```

```
cccataggca tacactcatt ctggtatttc aaccttctta caaataaaac tctcttcacc  35220
cccaatttct tgccagctac ttccccatct tggttttatt tatttatgtg tttgtttatc  35280
cagttgctct cctttgaagg aaaactcttc aaaacagctg ttcatactca ctgtttctgg  35340
ttaatctcat ctcctgcttt ctaaaaccca ctgtagactg gctttttccc ataccacttc  35400
aataaaactg ctcttgttaa tattaccagt gaccttaatg ttgccaaacc agtggtcagt  35460
tatcagtcct tatcttactc ggcctataac tggcatttga catagtttga ccctattttc  35520
cttaaagtac tttttaaag tcttggcttc cttccatgat ctttttgctt tgctctcttg  35580
gactcttttg tgggttctca ctcttctgtc agatccctta aggttagaac accatagcat  35640
gcgcagttct ttgttctttt ttatactttt actcactccc ttggtgatct catccactca  35700
tttgcttata tatggaaggt tatcatattt atatctgcac cccaagtttc cctcctaagt  35760
ccagatttaa atatcttgac ctggcattat cactagaata tctcaaagac atcttaaact  35820
taacatactc aaaatttaac tcctgatctg cctcccaaac cttctctacc cccagtcttc  35880
cccatatcag ttgatggcaa caccatcttt ccataccaaa gttcttatag tcatctttga  35940
ctctttctct caaatcgtac tctgtcagga aattctcatg gttcagcctt cagaagatgt  36000
ccagaatcta accactttca gtcaatgtat tactataacc ctttcttgat tggattacag  36060
cagcaacctc ccaacttgtc ggtttcattt tctacctgtt gtcaccctaa agtctatttt  36120
tattatagca atcagactga tcttatttaa ttaatttatt tttattctga agtatatatc  36180
cctcctctgc tcaaaatctt gcaatgaatc ctattttatt caagtaagag tcaatgtctg  36240
ggcaataggc ttcaacgccc tacatgagct gtcctctcca ttgtctctct gacatcatca  36300
tcttctactg ctccctaatt tactcttgct atgtcttaaa taacagatgc cttaaataga  36360
ccttaggacc ttggcaccag cttttctctc tgtatgcagt actcttccca cagatgtctg  36420
cgtggatcac tgccttagct ttgtccaatc tttggtgaaa ttttgtcttc ttaatgagac  36480
acttatcaat attaccctgt taaaaatttc aagctgtttc cacccatact gcaatctctg  36540
gaaagaaaag agtacagtta gttctatggc tcttctcgag actcagagat gcctggtgat  36600
ttgaccctcc ctataagtct tctttcaaca aggactcaag aaacttttag gtgtacatct  36660
atacttcctc caagggaatt cagctgaagt tactaggtag caggcactga tgtgtgcttt  36720
attacaagca tatgtcatgc actgatatgt attaatattt tattgttgag actggtactg  36780
gtgggggtag ctgctctaga aaatgaatag aagttcatgc catatcccta aaaagctgct  36840
cagctagcaa ggtataagca gaaggaatga ttctacctac ccaacatcac ctatcattgc  36900
cacacgtatc ttgagtgttc agtgactttc tgatattaga gatggcctgg gagtctgctc  36960
tgcttgtgct gtatgtactc ttttgttatc taactttttt ttttttggt gatgtagtct  37020
agcttttgtc gccaggctag agtgcagtgg cgcaatcttg gctcactgca acctccgcct  37080
cacgggttca aacgattctc ctgcctcagc ctcccgagta cctgggatta caggcatgca  37140
ctgccacacc cagctaattt ttgtattttt agtagagatg gggattcacc atgttggcca  37200
ggctggtctc gatctcctga cctcgtgatc cgcccacctc ggcctcctaa agtgctggga  37260
ttacaggcat gagccaccac gcccggccaa cctaaccttt cttaaaactc agcagtacac  37320
ttggtgctgg gcaaagcctt ggtgctgggc aaagcagtac acatggtgac tcatgactgt  37380
gattgtcact ctgaacccaa gatcaccagt aaggcagagt agacattatg atcccaatcc  37440
cctttacctt gctctaatct tatttttccc atagcttttg acaccttttg acatactgta  37500
taacctagtt acttatgttt gttgattaag ccttatgagg gcaggaattt tgttcattat  37560
```

```
ataggcctag cacctaggac aatgcctggt atacaccaga tactcaataa atacttgtta  37620
gatgaatgag aaaacaaacg tttctttagt atttattcaa tgccaggcgt aaaggattgc  37680
gaagaccagt aacagaattt ctgccattac atttctttga gcaaaggata tgattatggt  37740
catttctgag attggtccat tacagagatc cttagagaaa gttcccaaat cacatcagaa  37800
agaggggttt agagaaatat atttccaggg aggttacgtc ttagcaatga caatataaaa  37860
gaaagctgac tttaataaat tatatttaca catgtgaagg aagactgtta ttaagggaca  37920
gtttgtatgt aggggttgtc tgtccaaaaa gaagaatcct caaacagaaa taatttatac  37980
aacttagtct tcactgtggt ccaagaaaga tgatactatg aagagtgtga ccccacaatg  38040
ctagaagtag ccttaaataa aattatgcag gattactgct aaaatagacc atggtggtaa  38100
gggaataaaa ggatttcaat cttgaataca aaccactata tccatgtaat tagcattgta  38160
gttttagaaa ttttagcaaa taataatcat tatttgttct agtataatat ctagttagca  38220
tgcagatatt aattgaaaat aataatccag ttcctttttta atatggctag ctatgtaaat  38280
agagaagatt tctagccatg tgcatctgga ctcttgtgta attttaagat tttacagaag  38340
aatggtatct cataaaagaa tgtgcacata ttttaagatg tcttcacatc tgcatggttt  38400
tgtcatgctg tttatttttc ctggaacgtt catcttttct ttgtcagccc ttgcaagtcc  38460
tccttgtcct cctaaatcca gccacagtca cattttcttt ctggcttttc ttggcactgt  38520
cttcctgcaa ctggttctcc cccttaaggt taattgatta attgcttcct cttctgtgtt  38580
ccgaaagtgt ttatcacaag atgtgagtgt tatttattta cctgcctctg agtttcaagg  38640
gcatcttcaa catctttgtt accctagtga ctggcgttgt tcctgttgca taatatatat  38700
tcaataaatg gttattgaat ttgagcatca ggatatattt ttaccttgac cactgattga  38760
cccagcaaat atttattcag gactttttat atgcaagaca ctgtgttatg tgttgtgaag  38820
atactacaaa gataaatcag ttgcacaagt tcttgaaact ctacagtgta ataaggaaaa  38880
ataagtcatg cataaaagca actataatac ataatagaaa atgttatttt caagccgatg  38940
tgtaggttat gtgtgttcga gagagagaga gagaagacag attactttct gctagggttc  39000
aagaatgcct tcctgttggc taaggaaata ttttccttaa gtggctaaaa agctgtgttt  39060
caaaatattc ttttgatgtc tcacaaattc agtggaattc tcttaggtct aaaaatatac  39120
atctctctca ctttaacttg gtgtgctatt gtagattatt ggattaaagc actgctcagg  39180
gattatgctg cttcttgcca agcagtctac atttaaagta gaaataagat gtttcttttg  39240
gtgccataag gtatacattt tatgcattct ctagttttta gaagataccc taagggctaa  39300
gtctttaaca tgctgctaca agtttattcc taattgccat tgggaaattg gctgaagaaa  39360
gtttttaaca aaagttaaca atattgtcat tgagagaata attcaaaatg gattttaact  39420
aaaagctttt aaaaactttg gtgagcatag cttgaatgcg taatatttaa ttgcatttaa  39480
gccaataaca tatattagac tggtcttttt gtgcatcaag gcattagatg ttaaaagttt  39540
gaatgattac agatcttaac tgatgatcac caagcaattt ttctgttttc atttagactt  39600
ggattctcac ttgcatttat cttcagctgc tcctatttaa tcctctcgtc aaaactgaag  39660
ggatctgcag gaatcgtgtg actaataatg taaaagacgt cactaaattg gtaagtaagg  39720
aatgctttac cgtgctgtgt aaaaaagagc tgtggctctt tttcctgtgc ttgttgataa  39780
aagatttaga tttttcttgc cccaaagtaa tgttttccta aagtggggaa agtaatcact  39840
gggttacaat aaagggttta tagaaagcag gtagtgagat atttagggtc atggataatt  39900
```

```
tgttggtaaa actggctagt tgcacaccac tgctgtgact gcttctttgc tggtcttctc  39960
cccatccttc ataggcagtg aaggaccttg gagagttcgc tgtgtgctga tgggcttgcc  40020
ccagcttgtt ccccataatc tctccagtgg gtttcccagc atgttctatt ccccttcaca  40080
tgtcttccta ctcttcttta aaaagtctaa cgaaaggaaa tctgaaatgg ctattctccc  40140
aattcaatca gcaggaagac cctgtcacat gtcagtgggt gtttgctcct tcagggaaca  40200
tagagaggtg attcattgcc cacatgttga agggactcat ctccctggtt tgtcacattg  40260
aactcttccc tcagcgaaag catttgcatt gcttccccaa gtcactgcca gctccatgct  40320
atgcttctcc agatgctttc tctcaagatc aagccacaga gtgggcataa cacatctgga  40380
atgcatcctt cccaaccgtc acgatctagg ggagatctta catgcttttt tgaaccatgt  40440
atgatttcgg gatgaacaaa gcttgagaag caatttttaa attcctagtt atttaaatac  40500
tgactagaga acggaggtga tgcgagaata ggtaagaaat gagggttgtg atatggagaa  40560
aaggatgaaa agtttatttt ttgaggtact gggataagga gtagaagggg ctctatttat  40620
cttccctcct cttgatatat attttctggt gtatatgtct tattttgggt ttataataga  40680
acttcaaaac agaagtttaa ggccactgtt gaagtcttgc tagcttagcc tcaatataga  40740
attagaaaca cacagacaca atttatacaa attccttagg acccagagag ttcaggttta  40800
aaagcattct tccatgcagc agcagcagat gtatcagtat gtcttacttg agggaactgt  40860
gagcaaagcc atgcaagagt tgtctgctat atacccagtt agctattgtg tatagggatg  40920
ggggtgaggg gggagtactt tttttttttt aaaaacatac tgtttaaaaa tagatcatgt  40980
tttttttcct tgagttgctt gttagtttgt gacccaagaa acaatactaa aaggacagta  41040
tgtgtttaaa atctaacttt tgtgaatgac ctggattcta gtctagactt aacatgtgat  41100
ggctgtgtga ccttagtcaa ggcacttgac cccttctagc ctcagtttct tcatctgtta  41160
aatagagata atatgtcagc gggatctgag gataaattgt aataatgcag cctaagccca  41220
tagtgagcac agtgcctagc acatagtaaa tatttgacac acagcacata gtaaacagtg  41280
ttagacactg ttactatttt atgattatgt gaacttaggg aagaggaacc atactaagtg  41340
cctcagttca gagctgaaat gagtgtcagg tggcattact ggaagtagga tggtagtaag  41400
caccatgaga tcagtcacta tcttagctcc catctgacta cttacgccca tgcctaaatt  41460
catttatcaa taaattgttc tcagattcta gaagctattg acaagaccaa gcaggatcat  41520
acagaaaatg ttatagtaaa cttgtgcgag atgacctagt ctagcaaaca tgcacatgat  41580
cttagctttc tataaggaag ataaagtttt tagagacaag atgaaggaaa aaaataagtc  41640
tacaaagcaa gatagaccct tgaagatgta atggtgcaaa actacttttt aatgtatgtt  41700
atcttaatac ccaatggtct aagtcagttg ttggctaaat ttttcatctg ggaattttaa  41760
tggtgatatg agaagggcgg ggaaagcaaa gtagatgatg ttcattaaat gtttgctggg  41820
tgagtgaaga agaggaaatg atgtgcttta ctttagtgag catcacaatc acctgtcatg  41880
ctgatgaaaa ttatgggtac ctctattcac aatagcaaag acttggaacc aacccaaatg  41940
tccatcaata atagaagact ggataaagaa aatttcacaa atatacacca tggaatacta  42000
tgcagccata aaaaaagatg agttcatgtc ctttgaaggg acatggatga agctggaaac  42060
aattattctc agcaaaatat cacaagaaca gaaaaccaaa caccgcatgt tctcactcat  42120
aagtgggagt tgaacaatga gaacacaagg acacagggag gggaacatta cacactgggg  42180
cctgttgggg ggtgggggcc tggaagaggg atagcgtttg gagaaatacc taatgtaaat  42240
gacgagctga tgggtgcagc aaagcaacat gatacatgta tacctatgta acaaacctgc  42300
```

```
acgttgtgca catgtaccct agaacttaaa gtataataat aataataaaa attacaggtg  42360
cctgggacta caccaagaaa ctactttggt aagtctgaaa aagggatcca aacatctata  42420
tttttaacaa aattctgaaa ggaggcttaa gagcaattgc tctagatggt ctcttctgtc  42480
attgtttaga aaccaaaatg tcttgactct tatttaatct caattcctat tatgactagt  42540
tatcatctgt gttgtataga cttataagga tgccagatta atacaaatct ccaaaatatg  42600
tttaaagtag gtcactactt tagaaccagc agatcacagt ctctcaggga cttatttaag  42660
gtacagctct aagggcatca ctataccgaa tctcaacttg tggagatggg gtgtgagaac  42720
cctaatgttt ccaactagca tctacataaa agttatttat gtagaagtat caggactgct  42780
taggccataa tgtttataga gtgtgtgtgt gtgtgtgcat gtgtgtgtgt gtattttaat  42840
gtttgaaaag aagtggagtg ttcctatcct aacttactaa tttcatttat tcaaacagca  42900
acatgagtga ctgttgagat ttatggatgt agataatcac agcctttctc tatacatggt  42960
ggggcagagc atcttgaagg aagtcgggaa tactaggttt ttttaatacc agctccacta  43020
ttacctggct gtgtggcctt ggacaaatca ctgaatcttt ctggcattca atttcctaat  43080
ttttcaaatg aggaacatgg acatgatcaa tagttattaa tctagggctg acaaacttca  43140
aatgcttaca catgaagctc agaattgtgc tgccttcata tgccttatgt tcatttctga  43200
ggagagtgtg tagcttttat catttctcag agaaatctaa gaccccaaag aagataagaa  43260
ctactaaatt agagaaactt ggaggccttt ttcagctttg aaattatttt attccataat  43320
gatgtttttt tcaggttgca cctcttggaa taattcaata ataactcgac tgaaggaggt  43380
tatataggat gagaggaatt tgctttgcag acataacctt gctacatttt atgtgaggga  43440
aagaaagtgg cctgacagtc catttttgcc tgtgctcaca gttattcctt caatggaaat  43500
cattcctttg cagcccctac cagtttcatc tttgcattag gtggcaacct gcactgtgcc  43560
cacacacttg aagttttttt gcttgaagtg attctcatgt cacagaagcc catgatttat  43620
gactttaatg tcaaattttt tttttaattt cttcttgaac actttgtact gcccccacgg  43680
tccccgtggt ttttattcga aatgcttctg gcctgtttac taagcataat agttcatcta  43740
tttacagaac attttgcttt gtttctaaaa aaatgttgca acatttgttt taaatggcaa  43800
actcagactt acctaaagaa agggtcaagt atctgggaag aggatgaatc aagcttttat  43860
aacttgtatc tatgggatag ttaggttgca gattttagta gttgtaattg ttcatatagg  43920
aaggaaatcc agatattgaa aaagttcaaa ctagttttct ctgtgtattc tccctactct  43980
tctctttgtt tgtgacgact ttgtttcttc atttgaggca atttaactca atatgatttt  44040
gttgctaaaa agaaaaaatg ttttgtcttt aactttctat tgggtaatga cttgtcttcc  44100
tcaaaatgtt tcttaaggtc ccatctccat ctcgtaaagg tgaaattact ctgtcttttc  44160
aaggtcagtc tacaaattag taagatagca ttagaacaaa ggaatctatt gtcttcctgg  44220
tcttgtgata ggcacttatt tcaagttggc tatatttata catgattcat ggagattatc  44280
gtaatgagag attataaaaa tatcctcaga taacacattt tcacactttg aatagacagt  44340
tttgattaat tctgattatt tttcttcttc aaatattatt gttctcaagt agaattacca  44400
ctgcattaaa gtgaagaatt ggagtctctg aatgtcccca tttctggatg aattctaagc  44460
ttttcttcag atgacctagg tatatcatta atagtgaaga tttcacataa ttttgtttga  44520
ccttcgaaaa ataatagttt gaaagatagt tttcaaattt tattttatta ggttgcaata  44580
tttagcattt taatttctgc tcctgtggtc agcagaaaat tctttctcta tttaaagcta  44640
```

```
aatttaggac attttgtatt ttaaaaaaag gactattaga aataatattt attaaaactc  44700
tagatagatt gctatattat caagcatatg agtcttattg ttaggaaaac attgttcttc  44760
ctttatagaa taaactactt ggataatatg tcttctgctc attgaatttt tatttttatc  44820
ttttgtagag atgtgggtcc cattatgttg cccaggctgg tctcaaactc ctggccccaa  44880
gagatcctcc cacctctgcc tctcaaaatt ctgggattac aggtgtaagc caccatgtgc  44940
agcctgctcc ttggtttttt agaacaatag ttatgagtac acagacacca tgcagaaaca  45000
ctttgcatgg attgtctcct ttacttttca taaccttaca agataactat ttttagccca  45060
gtatattggt tagaaagctg agatctagtg gtatttagta atctgattat catcacttgg  45120
gaaatagttg agtagaggtt tgacccctta actacctatc attgaggcac agtaatgcag  45180
ttcataattt ataatgcctt cccagtagtt taagatgtaa gtttcaacta caattaatga  45240
attatcattg taacctactg aattttattt cctgaatagt agtcacctta tcttactgtg  45300
attaggaagc tatcatattg tagaagctca gttagttact taattggaat catcatcata  45360
aggtgtgtca tcatcataag gtatgtcatc atcatgaggt attatacact ccctaaatat  45420
tgtagtttat aatctcttct atttgaaaga aaaaattgtt atctatcttt atttagatat  45480
tctttactga ggaacgatga ccttgaaaag cctcctgaag ttgtcatctt aatttttttt  45540
tgagacaggg tgtctatcac ccagtctggg gtacagtggt gcaatcatgg ctcactggag  45600
cctcaaactc ctgggctcaa gtgatcctcc tgcctcagcc tctctagtag ctgggactcc  45660
agagtagttg ccaccatacc tgactaattt tttaaatttt tttcttgaga tggactctca  45720
ctttgttgcc aagtctggtc tcaaactcct ggctttaagc aatcctctca ccttggcttc  45780
ttaaagcagt aggattacag gtatgaacca ctgtgccctg ccaatttatt tttaatcact  45840
aattgagtta ccattttaaa aaagtccagt tacatttgaa aactataggt aatacacctg  45900
gttggttaga tttttagtca atattagtgg tagataattt tttaggagaa acaaagaagc  45960
aaaaagcttt tttggggggt gttatttctg aaggttgaac aactaacata gtaagctact  46020
gtacctgagt gaacgatgat agaagtgtag agcttttttc ctctacagcc atgattatta  46080
aactttgcta ggtctgaaaa tcatagactc tttccccaga aaagttgaca taggcacagc  46140
attttgtaaa agtgtcaagg gagtcataga taactaatga attttgattc ctgccttgga  46200
cttgggagag acagcataac aagtaagggt cttgcaaaga tgtccaaggt ggccactgat  46260
ctcatgagat ttagggacct cagtgaccct tgaaccatga gatccaaagg tttttagatc  46320
agtgatctag agaggaagtt aagtgttctg actttgagtt atttttcttc tgagtccaaa  46380
tacctgcagg gtgtggtatg cagccagtgc cagtttggct tgcaaagact tcttgttggc  46440
caagtctcca gcatttccaa atgctgttct cccatggatg tttttccagt gtcactggac  46500
atggtcaatc attaagacat ccaaagaaga cagtaaatgg ttcccaccta gcacagttag  46560
ctcatcatcc agtaacttgt ttttgcagtt ttttatttta caatctggca tagtattgac  46620
atccttgcac tccaaaccag agctcattag aatgagttgg cctttggtaa aattttccgt  46680
caattaattt ttttttgcca tgaatttctt tagtagaaca gatttgtttt ttaaaatacg  46740
tagccttggt tacttatcca cttaacccta ccaataggga atactccctg gactctagac  46800
ctggttcctg cttttctagt ttccagtttg catgtaaaca tttaatgtat attcaaattc  46860
ctagtggtct tctaatcttt tgtctgtctc tgttttctct ttgctccaaa ctgtcttccc  46920
atactaatct tggtatttta ctaccaggtt ccttctctgc tgaaacacat tcagtgttgc  46980
atcaccactt acgtaagtaa gtcaaaccag actgaattta tagaaattat ctagtttgcc  47040
```

ctctttatct tacagacaag gagtagaact tccacagaga tgatgctatg tgtctaagca 47100
gaagcaactt gctgtggagt tctgatggta gaactgttcc tactgtacct tactacctac 47160
catttgacct ccctagctca acatttggag ggtctctctc aaaggcagtt ttcctggaat 47220
atttcttatc tcttaactgg tctccctaac acattatgag ctttcccatt tctttgcctt 47280
tgcataagac ccttcctcta tctagactgt cccactccct cgcatttagt attaatagaa 47340
attcatactc attcacatac catgcctaac taagcactta gtattttata tgagttattt 47400
tatccttata aatccatcag ctagattcta tatgattccc atgtgacaca tgtaaaaatt 47460
taggctgaag tagatgaagt gacttgccca agacttctga gttagtaggt ttcagggcca 47520
ggatccaacc tgagtggtct gtctccagaa cctgtgctat taatccatac attaaattca 47580
ctgcctctaa ggagtatttt ccaagttgca ggccataggc tccctctact ctgtgaaact 47640
ttccacagtg atatatatca gagaagcaga atttatttca tggttatctg tgctttctgg 47700
aaggtgagtc aatatactac ggggttgaat atttcctacc caaaatgctt gggaccaaaa 47760
gtgtttcaga tttcattttt tttttcaga ttttagaata tttgtggttt tttcttttta 47820
atatactttc aactattatt tttgattcag cagctacatt tgaaggttta ttacttgggt 47880
atattgtatg atgctgaggt ttggggtatg attgatccca tcacccaggt agtgaacatg 47940
gtacccaata ggtagttttt ttaaccctgt cttcctgctt cctatctagt tgtccctggt 48000
atctattgtt gccatcttta tttccatgag tatgcagtgt ttagtcccca cttgtaagtg 48060
agaacatgca atatttggtt ttctgttcct gtgttaattc actgacaatg atggcctcca 48120
gctgcatcca tattcctgcg aaagacatga ttttattgtt ttttttgtg gctgcatagt 48180 attccatggt gtatatgtat cacattgtct ttattcagtc cattgttgat aggcacatag 48240
gtcgattcca tgtctttcta ttgcgaatag tactgtgatg aacgtacaaa tgcatgggtt 48300
tatttggtag aaggacttat tttggatata cacccagcaa tgggattgct gggttgaatg 48360
gtagttctga attctttgag aaatccccaa atttctttcc acagtggctg aacagtgtat 48420
atgcattccc ttttctctgc agccacacca gcatctgttg ttttttgaca ttttttaaa 48480 ttatacttta agttctgggg tacaagtgca gaacgtgcag tttgttacat aggtatacac 48540
gtgccatggt ggtttgctgc agccatcaac ccctcaccta cattaggtat ttctcctagt 48600
gctatccttc gcctagcccc ccaataccca acaggccctg gtgtgtgatg tttccctccc 48660
tgtgtccatg tgttctcatt gttcaactcc cacttatgag tgagaacatg tggtgtttgg 48720
ttttctgttg ttgtgttagt ttactgagaa tgattgtttc cagcttcatc catgtctctg 48780
caaaggacat gaactcatcc tttttatggc tgcatattat tccatgctgt atatgtgcca 48840
cattttcttt atccagtcta tcactgatgg acatttgggt tggttccaag tctttgctat 48900
tgtgaatagt gccgcaataa acatacgtgt gaatgtgtct ttatagtaga atgatttata 48960
atcctttgtg tatataccca gtaatgggat cgctgggtca aatggtattt ctggttctag 49020
atccttgagg aatcgctaca ctatcttcca caatggttga actaatttac actcccacca 49080
acatgacagc cattctaacc cctatgagat ggtgtcttat tgtggttttg atttgcattt 49140
ctctgttgat tagtgaggtt aagcaatttt tcatatgttt cttggcccct tgcatatctt 49200
cttttgagaa atgtctgtgt cttttgctta cttgttgttt atggggttat tttttgcttg 49260
ttgaattgtt taagttcctt atagattctg gatattagat ctttgttgga tgcatagttt 49320
acaaatattt tcccccattc tgtaggttgt ctatttactc tgttagtagt ttcttttgct 49380

-continued gtgtagtagc tctttagttt aattagctcc caattgtcat tttttgtttc tgttggaatt 49440
gcttttgagg acttagtcat aaattattcc ccaaggccaa tgtccagaat ggtgtttact 49500 aagtttctt ccagcatttt tacagtgtgg ggccttacat tttaatcttt aattcctttt 49560
gagttaattt ttgtatgtgt tgaatagtag gggtctagtt ccattcttct gcatatagct 49620
agccagttat cccagcacca tttattgaat agggagtcct ttccctattg tgtatgtttg 49680
ttgactctgt caaagatgac atggcttgta tgcatgtagc tttattttag atttcagatt 49740
agagatgttc aatctgtata aatgcttaga aagtaatatt aacacaataa tttattaagc 49800
gaccacaaat atctacaact tgactttcta agttctcttc caaatgtaat tagaaggaaa 49860
ccaatgaaaa ccaaggacgt aataatggga tactgcgcta taggtagatg tgctgagccc 49920
cagcacacaa agccagggtt tgcatcctac ctgcaccagt tactcctaat gcgtgtacct 49980
tggggatacc ggttaacctc tctgagtttc catgacctca tttgtaaaat aagcttaata 50040
taatctctca tggggttgtg gtagagactg tatatgaaaa cttgttttaa attataaagc 50100
acgtttcaaa aacagtatta tttttcagtc tcaccagaaa ttgaatatca gtaaatcagc 50160
ttaacgaata aattacttta ttattataca ctgccctacc accagtggta gaatgtagat 50220
ttcagtgttt ttatcaggga acttcctata agccttcttt gaaccaatat ttgtatataa 50280
attattcatg aaatggaatt ggtcaccata ctctttacat tttctttgct ttttagacat 50340
atactcagat cccacacttt ctaaatacta atctagttga ttgtattttt gtatttttaa 50400
aataatataa attatgctta agaaagggct ggattgttaa gcagcttgtg ttcagaatac 50460
ctgccacttc ttgctgcgtt tttctatctg gaatgccttt aatttacctg gtttattcaa 50520
aatgagatag aatattgctg cttacttatc gctttcacat ctgcaacagg tctgctctgt 50580
ctttgtcact agggtttaca taaaatgact agacgctttt tcctttcaaa gatgaggatg 50640
aagattaaga agagaaaaga aattatggaa gcttggtgga aagtttgaga ggaagaaagt 50700
taagtgtaaa gaataaggga gttaacgcca aaaataaatg aacaaaaatg ccgtcatgtc 50760
tggcagctca ggtgtgtttt caataagcag caatggaatg gacacggtgg ctcatgactg 50820
taatcccagc attttgggag gccaaggcag gcagatcact tgaggccagg agtttgagac 50880
cagactggcc aacatagcaa aaccccgtct ctgctaaaaa tacaaaaatt agccaggtgt 50940
agtggtgcgt gcctgtaatc ccagaggctg acacatgcga ggattcctta agcccaggag 51000
gtggaggttg gagtgagcca ggattgtgct actgcactcc agcctgggtg acagagtgag 51060
actctgtacc aaaaaaagaa aaaaaaagca gcaatgattc taatatttta tttagggtgg 51120
tatgaagaag gttgatggtg aagattcaca agtggaaaat acccagaaca agtgcccaga 51180
gggtgtagag tgtgaaaata tgtagtggag ctaagagaca agggaggctc ttctctccag 51240
ggacctgagt tctagtctag acttaacatg tgatggctgt gtgaccttag tcaaggcact 51300 tgacccccttc tagcctcagt ttcttcatct gttaaataga ggtaatatgt cagcgggatc 51360
tgaggataaa ttgtaataat gcagcccaag cccatagtga gcacagtgcc tagcacatag 51420
taaatatttg atacgtgtta gacactgtta ctattttatg attatgtgaa cttagggaag 51480
aggaaccata ctaagtgcct cagttcagag ctgaaatgag tgtcaggtgg cattactgga 51540
agtaggatgg tagtaagcac catgagatca gttactatct tagctcccat gtgactactt 51600
atgcccatgc ctaaattcat ttatcaataa attgttctca gattctagaa gctattgaca 51660
agaccaagca gaatcataca gaaaatgtta tggtaaactt gtgcgagatg acctagtcta 51720
gcaaacatgc acatgatctt agctttctat aaggaagata aagtttttag agacaaggtg 51780

```
aaggaaaaaa taagtctaca aagcaagata gacccttgaa gatgtaatgg tgcaaaacta  51840
cttttttaata tatgttatct taatacccaa tggtctaagt cagttgttgg ctaaattatt  51900
catctgggaa ttttaatggt gacataagag aaggttgcgg acagcaaagt tggtacagtg  51960
tgtaggaagg aagagaacct agaactctgt aacttactag ggttatatgc ctccaaagtc  52020
agttgccggt atagctctca gtaaagaaca tggattgagt gtttataatg tgtttggcac  52080
attcatctgt cttaattcta aatgaccatt tgacataggt atcttgatct tcattgtata  52140
aatgagagga accaacatac agagtttaga tttgtcccag attcctttgt cctaaaccta  52200
ttgcttattc acttatgcca gaatgactga tgtaagtaag tcagacgtta tttaaagcct  52260
tcaaaagaac ctaggcaaat atttgagact tctcaaatgt tcagccgaag gtaagagaat  52320
taagttacat cacaaaatga atctttctaa attatttctt ataaagcatt tgcatctcat  52380
aagtagcatt gttttttga agtttcactg atcatttttt aggttcaaca taaaatagtt  52440
ctcaaatttg ggtgcacatc ggaatcacct ggaggacttg ttaagtaaga ttcagtagct  52500
ctggtatggc ctgagaatat gcatttctga cagattccct attgctggca catcactttg  52560
aggtccacat tttgagaacc actgacataa aaagcatgta ttttatgatt aatcctatgg  52620
aggaacaagt aggaaaatag tccttgaggg gaattccaag atcacaggtg gaagctgaaa  52680
ttcagatcat gtttccaaaa ctcagtaggt tatacctagc caggcataac tgaatttgga  52740
gtctaaaaga tctgtattat cactttttta ttttgaagga tgccttttga ttacagaggg  52800
aaatcaagga ttaaaaatca atatacatgt aaatattgaa attcattggt aactttaaaa  52860
agcacaacag ttttgtgtgc ttttctccaa agcactacaa atatgattaa ttgatgtata  52920
agaattttct tatggaattt ttttttttgt ctctgtaggt ggcaaatctt ccaaaagact  52980
acatgataac cctcaaatat gtccccggga tggatgtttt ggtatgtaaa ctacatttct  53040
gagtttcatt ttagtagctc atagaagaaa tgggatcatt catattgaga tagtacacta  53100
gctgctattt aggagcttgc ttattgtcag gatttgaaga atttatcttt ggaatttgac  53160
ttgcaggctt ttttttcccc ctcttaagca actgttaaac tttatcagtg atcatttcag  53220
cacatatatc ctagacctgt atagttgttc ttcactatcc ttaggaaatt ggttccagga  53280
caccttccga ccctccatcc tccccactca ctccaccatc aggataccca aatcctagga  53340
tgctcaagtc atttctatga atggcatagt atttgcatat aacctatgca cattcttctg  53400
tatactttat ttttaaattt ttatttttca ccatggaagg cacactggaa ctcctgtgtg  53460
ttccaggagt ttagttccag gaatttggaa ctaaattaaa ttatttctaa attaattcta  53520
aattaattct aatactgaat ataatgccta tattacataa atcattgtta tgctctgctt  53580
ttaaaatttg ctttatgttt tcttattgtt tgaatatttt ccatctttgg ttggttgaat  53640
ccgtggatac agagggccat ctgtacttcc aaagtaaata cgattatctt ctttagacct  53700
agccacagat tttctcattt tccttaagca tccccctaaa aaaggacttc agtgtaagtt  53760
tatgtaaatt ctttttcata gctgacctac ctcacttgtt taatttgaaa gcacaatttg  53820
atttactagc agtgcaatag attcttagaa ccttacaaca agtgtatgtg tttactatta  53880
taagtactac tctgttgctg aaaccaagaa attttaatta tttttctcat tacacagtat  53940
cagaattcat acattaagaa atatttcaag catagagaat aatgtaatat ctgtatacct  54000
atcacagagc ttatcaaacc ttaccattgt gcaatatttg cttcaaatat atttttaata  54060
atgaaacatt acaaatgtaa ctaatgccct atgtatgctc cttctctgtc ttcattaatc  54120
```

```
cccagtttgt ctcttagtgg taacacttat tctgagctgg actttttcat tccaatgtgt  54180
gctttcaggg cttgtaatgt ggacagcatt cactagtgtt atgtagagca ggaggagcat  54240
tctcttatat gtttactgca gtgtatgcac ccatacataa gacatggaac tttttgaata  54300
tttaataatt ttatgttaag cttctatact ttgaagttcg cttatatctt tcaacatgct  54360
ttgacaagtt gttttatgtt gactcatttc aactactgta ctgtgtttct tgagtaaatt  54420
taaaaccatt tgagttactc tcttctctac aactctcatc tttccataat ctaccaaaac  54480
ttattaaaca tctactttgt gtaggttttg accaattttt gtggatcagt ccatcaaagt  54540
tgttaccaat ttaaacacat cattatgtgc ttgtgcttaa aatgcatttc aaagactaca  54600
aggctgtcat ttcaagagaa tgtcaaagct acatttcttt ttattagtaa gcattttagc  54660
atgaactacc taaagttttt tttagaattc cttagaacat gtatcttcat gttgaaccat  54720
ttatcctcaa gcctatgtca atgtctatcc tattgagtta gggggagttc tctggaaata  54780
gaaatggaaa attattagca gcctgaaagt taattaattt tattatttgg ttactaagca  54840
agtatttagt taggaaaaac taaccaggag ccagcacttt ggcagacact tgaagaaaca  54900
aacacacacc aattaggcaa tgatctttag ttcaaaaagt ttagtaattg ggaaggcagg  54960
caggggggat tatgtggcct ttttataaca cttttccatt tgcaaaatga tttcacatat  55020
taattttctt ggctgattag aaaaactctg aggaaggtaa aatagctatt atgattccta  55080
ttttacaaat gatatattga gctttacagc gcaaaagtat tttgcccaag gctatacaat  55140
tagaacgtga cagagtctta aaaagaaacc cgtaggtcat cagactctta accctgggtt  55200
acggaaagtg aggatctata taattacaac acttagggaa agtgtttgaa gggaagcctc  55260
taggtaataa agacccaccc cagatccttc ctgactgcag cagcatttag gattgtgatt  55320
gccaagcacc caaagataac ctgctgctct ttgaaaaaca aatgctaaac tgaaaacaac  55380
taaatagaat tttttgtgct ggtataatca tagaatatgc taaatcatag atttcaatgt  55440
cggcttgtga tagcaagagc caagcttgtg aaaataaagc tgattcactg ccacatattt  55500
tgtgcttgtt tctgtaattg agaaaaatct actattgatt ctggcatgct atactggcac  55560
aactggagaa acactgttct tcttggccac caccatgggc aagaaaaaca aggccacgtt  55620
tagagcattg gacagaacca ggggtctcac cctttgtttt accttcattt tgacatgttc  55680
gtttctgcga agaccagagg agtttcccag tggggaggcc tctgattatt tgcgagtggt  55740
cagagtccca gctgccttat cttttgtctt taaacaatag agggtggagt gggaatgggt  55800
gccaaaaaga ttctctggtg ccaaagcaat aaaattctgc ccatgggcac tgggcagaag  55860
aaagctctag aatagaatac acttttattt ttatttttat tttgccttca ttttaaaaaa  55920
cagctaaatt ctcctagaaa agggagttca cttttccaag gtccttctta gaaaattacc  55980
tagcagattc tgtctcacaa atagcagggt gtgatcaacc acttagtatt taaatctaac  56040
gataatcacc aatgctattt taaactcttt gaaactatta tattgccgga ctgttgaaat  56100
ttcctttaac ttcctaacct taaagaatac ctggatattt ctggtctttt acatttactg  56160
gtaatgttat tgtagaaaga ataaaaatgg cattgctgaa ttgttgccac acaccttcat  56220
tcacttgaac ttccatagca tttacataaa ctgtgggttg cttgtaatat ttgagtttaa  56280
aaatcttcat ttttaaaaaa attttttat ttttagctat tatggataca taagagttgt  56340
gtatatttat ggggtacacg tgatattttg atgcaaccat acagtgtgta atgatcaaat  56400
cagagtaact ggaatattca tcagctcaac tttacaattt ctttgtgtta ggaacattcc  56460
aattccactc ttttagttat tttgaaacag acatttttat taactgtgcc acctattttg  56520
```

```
ctactgaaca ctggatctta ttcgtttttc aatttttact taaagtatat attcatcagt  56580
tttcttttag ttttttattt gcaaataatt ttaaatttac aaaaacgttg caagaatatt  56640
taaagaacac ccatgtgccg tttaatccag attcacctat ttcaagtatt tttaacattc  56700
tgcctcattt gctttatcag ttgctttctt tctatgtatg catgtgtgtt ttattatgtt  56760
tctgaacttc ttgaataagt tgtatactga tgcatacatg gccatttact cttaaatact  56820
tcagtgtgta tttcctatgt gaaggatatt ttcttaccta aacacagtac atttgcaact  56880
tcaacacatt ttacaataat tatagtactt taatctaggt ctgcatttca atttagcttt  56940
tttgtttttg tttttgtttt ttgtttttttg catttctttt ccttcagtat aagatcctat  57000
ctaggattgg aattttcatt ttgataccat gtaaataatg actcccaaag atgccttgtt  57060
ttgggaatat attacctgac atggcaaaaa ggactttgca gatgtaatta aattaaggat  57120
ttatagatgg aaaagttatt ttggattatc caggtggtcc cactctgatt tacatgagtt  57180
cttataaaag ggaggcagga gtgtcagagc cagagaggga gatttgaaaa tattacactg  57240
ctggcttcaa agatggaaga gggattcaca agccaaggaa cgcacatggc ctctgaaagc  57300
tggaaaaggc aaagaaaatg atttttcctt tacagcatcc aaaagaaaca cagccctaat  57360
gaataccttg gtattagcct attcagacct attttaaact tctgacctcc agaactgtaa  57420
aataacaaat ttgtgctgct ttaagccacc aagtttgtag tactttgtta tagcagcaat  57480
aataagctac tacatcctgt ctctctagtc tcctttaaga tttcctcagg ctttctttgt  57540
ctttatggca ctgacatttt tgaatgagac agtcctcccc tttaagaaaa gtgtttctct  57600
ttgcaacatt tgattgatgt ttcttaatgc ttctgtggag cttatgcaat tcaagtgaca  57660
atgctacgaa agtgatgatt tgtgctcagg taaccacatc cagaggcaca cagagtccat  57720
cctctcctca tggtgctgtt tgttttgatc atctggttaa gatgttcaac tgtttatgta  57780
tatttactca ttcacaattt ggggagagac actttaaggc catataagca atccttctcc  57840
ttctcaaagt ttctcccaca gatttagcat ctattgatga tacttacctg aaccaatctt  57900
tgctatcatt gtcagttttt cgttcagact ttttaaaggc acagctaaat atggaagtga  57960
ttggcagcat gtgatgccac tctaacaata agccttccaa acttcttccc tcttcagtac  58020
ccttcctcag gtatgcacaa tttcacttct tggctattct catctttttt tgcctggccc  58080
tgttacttac ctctgggctc tttccatttt ctttgatacc tgaggattta ttatttgatg  58140
ttttgattct tcctgaatag acagagtgat ttaaaaagaa atacatccaa tcatttcatt  58200
cctgtttctt tatattcatt gaatggcttt ttgctgctct taggaaacag gaaaaggagc  58260
tgcttcaaca aggcctccaa gactgtagtg atctagctgg gcacagtggc tcacgcctgt  58320
aatctcagca ttttgggagg ctgagacagg tggatcatga ggtcaggaga tcgagaccat  58380
cctggttaac acagtgaaac cccgtctata ctaaaaatac agaaaattag ctgggcgtgg  58440
tggcgggcgc ctgtagtccc agctactcag gaggctgaga caggagaatg gcgtgaacct  58500
gggaggtgga gttttcagtg agccaagatt gcaccactgc actccaggct gggtgacaga  58560
gcgagactcc gtctcaaaaa aaaaaaaaaa aaaaaaaaga ctatactgat ctggcacctt  58620
tccacatcct ttttcagtcc tttatcgtta tcgttaccag ttccttgctg ccacatagct  58680
tcttgcctgg ctttctctat tcctggaatc ctgattggtt cttttgtcta gctaacacct  58740
gattctttta gattttggtt ttgatttttg atgaaaccaa attgttctac tggaaactct  58800
tctcatcgca ctcctcagag tagcagtttt ggatgtattt gtgggatgat ttaatagata  58860
```

```
atcttccacc aacctgtaaa cttcacaaag gtaggaacta tattcttttt gctctgcatt  58920
agattctcag tgcctcatgg atgctcatat gcatttaatg aatatttgct gaaagaaagt  58980
gaagaaagga aggaggaaga aaatttccct accatataat catttgtaat ttccttgagg  59040
cacagatttg aacttagttc acaaggttat aatgatgagg tgagtgccta taactcgtca  59100
cacagtatct gcactgcaac gttattatct tcttttagat acgtgtgaat tttttgaaat  59160
attttaggtg taagaattgt attatgcaat tttggggaat cacagcttct ttaagccttt  59220
ggttctactg ctttaattga gttatttttg cattcaagaa cctgcttatt gttcccattt  59280
actaaaggct gagagccaga ttcctgaacc taatgttcat gactctctgt aatccttccc  59340
taccctaacc aactcatctg aatacccatt attccccaac acaaacttgc cacctcagcc  59400
acatgcatca ctgcctccta aaataatgcg cctgttctca aaggatgccc tttcttctcc  59460
catccactta tccaaattct acccatagaa tcatgcaata tcttggggct taacccatct  59520
tagtggtcat ctcctccaag gtcagtttaa gatttctctt tcacacaagg acattttctg  59580
ctctttcagc ccacattttc tctcccatgt atcatttgat caggtgctac tctgtgctga  59640
gtgttttgct tgatgctgga gcttggtggt cagcaatact atcattgcac ctgctatgtg  59700
gaccctatct tttagtttat tatcttgtga cttctatgga atttgtccag aagctattca  59760
tcttgggtac atgatcatat attgcttaca tagagcttaa tattttaagt gttatatatt  59820
tgtctcaaag tattatcgtg agaaataatt aaaatacaaa aaatatgagt tgtggtgtgc  59880
atataataac atcagatacc atcattatta ttttgttgtt gtgttctctt tttactatat  59940
tttgactatc tacagagcaa ggttgaaatc ttttactcct gtgtatctcc tcaccattct  60000
ttagacaatc caatgcatat agtcgctcct caaaaaatag ttatgaataa acatttaact  60060
cttggcaaaa atgctagatt tccaaatctt gaaggagccc atcttattag tttagattcc  60120
tgtggttttc actaatagta aaagtcccat tattataagg acactaaaga atagcatgtc  60180
acctaagggc atgggtgcaa caggccccat gaaaagactg gaaccaggat tggaaactat  60240
cagtttttcc ttctccatct ctgaatctct gtttctccgc ctcattctat ttgtgcagat  60300
attttctcct ttgttccagt cacttggtag aatgtaactg cccaagagct gccaggttta  60360
catatttcaa tttcagccct attcagagat taattatcag tttctaatga tcaataccaa  60420
ttttggggag gaacgttctg gttggcctat ccaagtcagg tgtctaccat catccaacca  60480
actatggcta cagggaaagt tcaccgtttg taagcatgga ttctgaggct ccactcctat  60540
gatgcggcat tctctctata aaaatagacg tcagccaaat agacacttgt agtcaactat  60600
ttatctgcct cgatctccca tgtaataaga aagtatttat ttaaaaggaa taagcataaa  60660
atgttagttg aatgaataaa atatgacatt aaatgctatt ttaagtagtt cttttgtata  60720
ctgtactaca gcacaggggc ccgtcttcct aataagtgat tatattaaga tgctgttcag  60780
attatctagg ccattattct ctgatagaaa tacaatggaa gccacgttca taatcttaat  60840
tgtctggtag caacactaaa aaaaaaataa ataaaaacga gcagctgaaa ttaagtataa  60900
tgaaatttat ttagccccat gtatccaaaa tattgtcatt tcaccttaaa atcaatataa  60960
aaattattaa tggaatgttt tatatgtttc atattattca aaatccacag tgtgttttac  61020
atctgcaaca tattacagtt catacactaa attttcatta gaaatagtta ttccatattt  61080
agatttttta ataaaattta ccattgagaa gatagtcaca tttctgtgtt ttccaaacat  61140
acttaaaagt tccagcctct aaatagggtg atattattga cttttcaatt taaagaaatt  61200
ataattaagt aaaatgaaaa ttttagctct gcagtcacat tcaatgcatt ttgagtgaga  61260
```

```
ggagctgcag atggatagtg ggattcccat attggccagc atcgattaga atttatttta  61320
tagatggaga aactgaagcc ctgaatagat taaatgactt gcctgaaatc acaaagtgaa  61380
ttgacagagt tgggactaaa aactgggcct ctagttcatc gttgctgccc tcactcccca  61440
aacccctgtg ctgttccttc actgttctat tttagggcgg gcctaggggc catttatagg  61500
tctgccctgg gaaataacac atatttagag tgctttggtt gattaccatc ttaatcagat  61560
tgagatttct acggcacttt aattcaaaca agaaatgtaa agttagatgc ctaaagtgaa  61620
cactgaagac ccaaattaat tgtttaggga gaggactaaa ataaatcatt acaaaaccca  61680
gctaatccaa agagaagtta agatttcgga gactacactg gcaacatgaa catgcaatat  61740
tttgcaaagt gcttttatag gaaactttta aatttgcctg cccatggaat gtttgagagt  61800
agaatgtcag ctttctagcc acaacgaaaa aaaccaaaag aacagtaaat aaagtccaca  61860
aatggcaatt gtcacaattc ctcagagaaa tttaccttca ttggtatgac tctggattaa  61920
ctgaaatgaa acagaaagaa ccatttctat tccaaagaga tttcttaatt gagccgaaga  61980
atcgtgtctg gtccagacgt gagaccacat gggtcatagt gaattcagca gaaaaaaaca  62040
cttcagtttt atgtgctttc actattctca tggctactag aacaaaatga gtgatcgaga  62100
gtcctggttt ctcgcgtttc tgtgtaaatt tgttatgtaa cctggaacga gacacttcac  62160
tactctaagc cttgattttc ccgcttatac aattggtgag actggtcctc agtattcctt  62220
ctaggtctgg aattctggtg attctgatga catggctcta gattttgatt gcacatccca  62280
gaggtagatg ctgaaagcac aaacagaaag gtacacttcg tgccctaggc atgcatacgt  62340
ctaattccag caagactgaa gtttgacacg aattaaagaa agtaaaacaa aaacaaactg  62400
ggtggtaatg ctggtattta gattaatcag attagaaggc tgggtgaata ctccttatga  62460
atattcttag aaacctcata gtttatgagc caggcttttc actctgagaa tctctaattg  62520
gtatttcacc aactcctgtg aaaagaacgt tctcactggg tagatactag ctttaggccc  62580
tataagaaag aacatagata tctctctgtg aatagctacc aaattgaaag taatgtaaag  62640
tgcttcagtg aagaagtgtt acagtattat tttgtctact ttcagcttct taatccgtaa  62700
atcttaccgt gactgctctt aaagactgtc tgtggggtgg gcgcggtggc tcactcctgt  62760
aatcccagca ctttgggaaa ccgagatggg tggatcacct ggagtcagga cttcaagatt  62820
agcctagcca acatggtgaa atcccatctc tactaaaaaa acaaaagtta gctgggcgtg  62880
gtggcagatg cccgtaatcc caactactca ggaggctgaa gcaggagaat cgcttgaacc  62940
caggaggcag aggttgcagt gagctgagac cacgccattg cactccagcg tgggcgagaa  63000
gagcaagact gtctcaaaaa aaaaaaaaaa aaaaagactg tgcatctaat accaatgtgg  63060
aataatgtgt caaattattt cacctaataa accagcacag tttcttgaat gaggcaggag  63120
atagagagga gaaagcatgc cagaattagc aagtctccag gatgatttta aaacacatgg  63180
tttatttcag ccggtttctc aaatttactg gttctggaac tacagagatt ctgtgtcaca  63240
tattctgtgg aattaatata ttacctttta aaaatttatg cttagtctta gaatgtgcat  63300
atatttctgt tgttggtctt tggaaacagt catattccta gttatgttta gaatactttt  63360
aattttattc attttaaatt atatatttta tttaatcatt tagcgagatc atgatttggt  63420
gttcatggta ctttaaaatt cctaaggaag ttcacagttt ttgactgaat tgtcagtggt  63480
agtgagatgc tagcagtcca atatcattga gtcaatatca ttgagtcagt ttggattcta  63540
gaataataac atgttataag tacataggga tagaaagcac atgtttttag tagtcctagc  63600
```

```
tagagctgct ataattaacc aagaaaacat aagacagaag ctatcaagaa agaaggtaag  63660
aaattgagag catggagtca agaaaaaagt ttttacactc aaagcagaat ctatatgttt  63720
cttcttttgg aaacaataca tacaggcgaa taaagcatca aattacatgc acatcaggaa  63780
tttaaaagca atcatttgtg tcacctttga catcctgtat gactgtcaat tttcttaatc  63840
ctttatattt tctagtgaaa gagagaacat tatatcttac tttcttctaa tgaatatcat  63900
tgagtaaata tttatataaa actatttaag tttaaaatat ctctgaaaaa taagaaacag  63960
tgataatatc atttattaag gcaaacaaaa agtacgtttg taaatttgac aatctttaat  64020
catttatttc ataatcataa tcgtggagga attgaaaaac agaaagacct gctatcacct  64080
cacaaatgaa atacttagtt cattgtgttt tattctcctt gcaaatcatt gacgatattt  64140
aattaaaaat tacaaaactg ctagacattc cagtcaaaac tagtttcctc tcttacaagc  64200
aggcagatca aaactgactg acatttaata ttatttgttt accttcattt tatctttaat  64260
aaactcaaga atcttaaaaa gccaatatat acatggttaa acaaattact gaaaaataga  64320
actttgaatt tatgattcag ccttttccaa agaaacaata gcacaagcaa aaataaaaaa  64380
tgagtgaaac atgattacaa gtgttttaga aatacacgat ttttcagctg tgtaggcacg  64440
tagtttatat caactatcaa caaattgttc atgactttag aagggcaaac attagagtag  64500
gattagattg tggaatttcc atggtttaac tctaagaaag cacaggattg gggttggaaa  64560
ttttactgga aagagttgat tgtttagact gttgatttag ttatgtgaaa atgggaggag  64620
gtagggtaat agctaaatag gaactagaat ataaaatgta aacatagagt tcggttgaaa  64680
atagtgatca acagaagtgg cagtaagtac cccagaattc ctcagcttaa aaataagaaa  64740
caaatcaaca aaacattttc tactttaacc acaaaaaaaa agcaaaatga acaaagtacc  64800
cattcatata agacaactac cacagaaact aaaggaatgt cttaattcaa aacaaggaat  64860
ttgattttgg ttcttacttg ccagagatcc taggcaagca tactcataaa gtgaggaaat  64920
agagtcctaa gagattaata cctggaattt cattgttaga aaaatttgca caatttcaac  64980
ggaatgaatt ggtgaaagct actctatcac ataaatacta ttcaaatagc aatttacagt  65040
gtatgctgtg ttccatatcc taggaaatct gttcattgtt gatagggctg acggtctata  65100
aggaattatc actccctaaa aggaaagaaa cttgcagagc aattcagcat ccaaggaaag  65160
actgacagct ttgaaagaga cctgataatg atgcaagtag gaacttgcat gtgcttgaag  65220
taagcactga tttaacaaaa caaagactct gttctgcaca tactttggaa acacatattc  65280
tttgagaact tggttatgac gagttgaaat ggccacttga actaaattcc catgttgaga  65340
tttgtttatc cttcttatct gaagccagag ccaacaatcc taaaagtttt gagtgacatt  65400
taatggttcc aggaattggg gcttacctat ctgcagataa acctgcttcc tttttggctg  65460
tattatatta agtaaaacag ttctgttaaa tgaatataaa gtggtccctt ctatacttta  65520
gaataaataa atgacttgag ccagatgcag tgactcacgc ctctaatccc agcattttag  65580
aatgctgagg agggaggatt gcttgaggcc aggagttcaa gagcagcctg agcagcaaag  65640
caagatccca tttatataaa aaaattaaaa attagccaca cttggtagca tgcgccttgt  65700
agtgccagct acttgggagg ctgaagtggg aagatcactt gggcccagga attcaacatt  65760
gcagtgaacc atgattgcac ccctgcacta cagcccagga ctcagagaga gagcctgtct  65820
ctgtaaaaaa ttaaagcata aataaataaa taaataaata aaaggcttga cttttcccac  65880
agagatattc tgctggtaaa tagagaaata aagcttagta gtttgattta ttttccatga  65940
catcagttac tctgagtaca atatttttgt tacaagttgt attaaattat ttgtgctttt  66000
```

```
aatgagccaa ttcaatgtta ttcttaataa caatgttatt tttgtcactg cagcatttca  66060
gcagtgttca aaatacatca gagtttccac ttaaaagatc tttataagag aaaagataac  66120
acattaaaat catataaagc atgcaaactt acaacctcct cctcctgtta caagagtccc  66180
tcctcctatt acaatagtcc ctcctcctcc tgtcacacta gtcccttctc ttcctgttac  66240
aataacccct gtcctcctat tacaacattt taagtaatgt aatattaatt ttaaaaatct  66300
ggccaggcac ggtggttcat gcttgtaatc ccagcacatt gggaagctga gacgggtgga  66360
tcatttgagg tcaggaagtt tgagacagcc tggccaacat ggtgaaactt cctctctact  66420
aaaaataaaa aagtagccag gcatggtggc aggcacttgt aatctgagct actcgagagg  66480
ctgaggcagg agaatcactt gagtaactaa aacgatagct ttgaagagta ctccgagttt  66540
tatggcactt acttattaaa atagctgttt tgtctctttt ttcatatctt gcagccaagt  66600
cattgttgga taagcgagat ggtagtacaa ttgtcagaca gcttgactga tcttctggac  66660
aagttttcaa atatttctga aggcttgagt aattattcca tcatagacaa acttgtgaat  66720
atagtggatg accttgtgga gtgcgtgaaa gaaaactcat ctaaggtaac tttgtgttca  66780
ttgggattat ttttcattac gcttctctaa aaacccatgc ttcttggtgc tgttggggaa  66840
aatgaggcac ctttatttat gatattttga ttgtataaac ttcaaattta aaaatcttgt  66900
tcagatgagc aaagaaaaca agtatttgca gttatactgc aatactgaag tgcacattca  66960
aacttaaatg ttgtcatcta atacaaaaat aaaacttatt tacattacaa tgcaaaatca  67020
gtcctgcctt tatctttatt cttcataagt gaagtccttg aaacctttct attaagttac  67080
aagtgttcat ttaaatggaa aattgtctgt aataaacaca tatcctttta tgcataatgt  67140
aatcacccca taggtcacag caaaggaata cattttggct cctcaaagtc attggataac  67200
tgatcatcac caacttcagg atatgggcat gacatatgga ataggcaatg tactccagaa  67260
aataagagtg agatattgga gtttaaattc tggctctgtc gctaatgagt tctgtgagcg  67320
taacttcttt gtacctcact ttctttatct ttaaaatggg ggcaatgcca gaattcatct  67380
aacagggtcg acgttaggtt atttgccatg agtactttaa caccctacct agcaaaataa  67440
atattaataa aatttgatgt tttttcatca cactgtgtct atagcaaaat catgcttagg  67500
agacctgatt tggtatacag ttcaaatggc caaagattag cttaggagac ttatgtaagt  67560
ttaaattcaa agttttaagc aggattctgt accttaatac ctaaatgctt tttcctgtgt  67620
cccatctaaa ttccagctat tctgtaagac ccaacttcaa tcccatttgt actatcctat  67680
cttataattc ttaccatact aataatccaa tcactacctt taatctttgt attattttct  67740
aatttccaaa gtcagaatgt ggtgttaacc actctttcat attactactg catatagtgt  67800
gccaatggca ttcaaaagaa gtagagatca caaaaagtag agtgcatcac acaaggtgtc  67860
acaaaggaaa taacatgtgc attagagcct taaagatgag ttaggtaaat gagttaggtc  67920
aatggtgatg ttgggaagaa cactgcaaac aacaaagaat gtgcatttac taatcatggc  67980
actttggtgg gaacccagga gattaccaat tatatttctc agttgttttg gagattgagt  68040
tactgtatat aaagcactta gaatagtcca tagtaagtaa cagatagttg tttattttgg  68100
ttacctactt ttctttataa tccattatgt atccctacaa catagctttg atttgctttg  68160
gggaatttta tattaatttt atatcaatta atcataccat ttttattatt ttgggacttg  68220
cctctttcac tcagctttag gtttagaaga tgtatccact ttaaagcata tagctgtagt  68280
taaccttctc ttgaattgaa ctccactaat tcaatatatc actagttatt aagccactct  68340
```

-continued

```
gtctggattg acataagtga tacagatatt gctgcaaaaa aactttttta tatgtctgat  68400
ggtatatatg tgcaatagtt tcagtaggtt atttacctga gaatggaatt tctgagtcac  68460
aggatggtca catgtctaac tttactggat aatatcaaat gtaccaactt acattatctc  68520
agcagtatgt aagagttccc ttgccaatat ttagtatcat ctgactttct aatttttgga  68580
tattagagca tgcattatgg tgtggttttt tttttttttt tctaaagact ggaagttctt  68640
gtaatggagg ggtcttttaa aaataaaccc tcatgttttt aatgagcatc tctaaagaaa  68700
aatatcccca gcttgttttt aaggttattt attttatttt attttttgcc atgacattgt  68760
gttcactgcc ccagattcaa cttgtgatcc cactgggatc actaccctgc attaccaatc  68820
tgaattacat acgttaaaac agccatctaa aagtgctagt tgtaagagtc taaatacttg  68880
aatctttgag agacatattt atagtccatt atcttcacct cagttaagtc tgaagactat  68940
ttgaaaaatg taatcctatt ttttcttcta ggatctaaaa aaatcattca agagcccaga  69000
acccaggctc tttactcctg aagaattctt tagaattttt aatagatcca ttgatgcctt  69060
caaggacttt gtagtggcat ctgaaactag tgattgtgtg gtttcttcaa cattaagtcc  69120
tgagaaaggt aagacatgta agcatttcca gttcaaatgt aaacaacaaa cttaaatctt  69180
ccctatgtag taagaatcta cctctgtgtt aagctgtagc aagatacatg catgtacgtc  69240
taataaaaaa gcagatatca atagcacaga agaaactaat gattgtagat ttgtgggttt  69300
ctaacccaaa gcaatattca tcagtttcaa attagtgagc tgtttgtgag taaacaatat  69360
atgagatggc cactcatacc ttttctcatc taatatttgc cagtaattac aattatatta  69420
ttctgtacct ccagtctact taatggtcct tctcaaattt tttcttaagg atctaactct  69480
aagtcacaaa ttctgatcct ccccagttac tctgtattaa gactcttttt tcccttcact  69540
gggtccctat aatacaaacc tggattcatt gctttctttt tttaatgaga aattaccatc  69600
aatgtgtcat tatttgtatt tattaacata tttattcaat aagtatttgt tctacaaggt  69660
gataatggtg gatttcttag taaaatagaa tagcaggacc cagtatgaaa taaataggat  69720
ctgaatactc tagatttggg aagcagacct ggcaagtaat ctggtattgc acttcacctt  69780
tcagggactc tataactcat acaaatcacc atataacact gacacattat tgctttctat  69840
ttagattcca gagtcagtgt cacaaaacca tttatgttac cccctgttgc agccagctcc  69900
cttaggaatg acagcagtag cagtaatagt aagtacatat atctgattta atgcatgcat  69960
ggctccaatt agcacctata ggagtattgc atgggctttc aaggaaactt ctacatttat  70020
tattattgat actgttctgt tactgttatt ccttttatgg tcttcttgag acttaagttt  70080
gtagaattaa atttccctag agctggagat aatgtttaga gaattaggcc aataaatttt  70140
ctgctgaggt tattttaaat aagacataaa attaatttta gaaatatgat ttatgccttt  70200
tgttgaatca ttaacatata ttctgtgtgg aatgtgtctg acaaaaacgg aagtttaaaa  70260
ttaagtgtat aaatgctggt tgttaacata tattctgtgt ggaatgtgtc tgacaaaaac  70320
ggaagtttaa ttgtataaat gctggttgta tagaattcca aagatatttt cagatttgtg  70380
tatatcagta tttactattg cgcatttgga aatttgatga ttttgttatt ttaccacaga  70440
attatatgct tgatgagaat aggcttattt ttctgaaatt tctgtcctct tttgccaaga  70500
acccaatttt ctttgaaaat ccagacaaag gtcattataa agtttattgt atttactaaa  70560
tactctctag cctcatggaa ggtgcaggaa gaataaaaac catcttgtga tctaggctaa  70620
aaaagtcatc ccttaggact tataaatggg gcactgtcat ttgttcaggg acttagaaga  70680
cctatctgtg aaaagaagta atcaatttat tactaattca taatagcttg ttacaatgca  70740
```

gaacatttaa aaaaactcta aaatacaatt tacttatttt ggaatttttt gccaccaaaa 70800
cctgacctga agtgatttga ggctatttat agtctattta tctttctaaa agtgaatata 70860
tattttacta atgaaatatt aatgtatttg attacagaat gctacccagg attcactggg 70920
gatagtatat gttatacatt atgtgcagga cagaatcttc tgaaacctaa aattctaaat 70980
tacgtagcat atcagttcta aaatgtgtca aaaagggact agagccctgt ttgtgtgtta 71040
gtcaattaag ggttttctta ccaactatgg attttattaa cattttcaaa ggagcaactt 71100
ttgtcttctt aaattctctg cttatatttc attgatttct aatctttatt atttccttcc 71160
atttgctttg tgtttcattt actccacttt ttctagcttt tcgaagtgga aaaattagat 71220
cattgatttt aaactatttt tgctaattac aagcacttaa aggtataaat tttcttaaat 71280
acactgcttt agctgcacct cacacatttt tgtgttgtga ttttattatt ttttctaaata 71340 tttgtcaact gtgatttctt ctttgattca tggataatat aaaagtgcgt tgtttgatgt 71400
caaaaagttt gagattttcc tatatatctt attgttacta gtctatgaat tttgttgtca 71460
gaaaacatac tctataattt ttttgaaatg tactgaaact attttatgta tgttatttaa 71520
ctgttgaatg cagcattcaa atttggccaa aatggttgat agtgttgttt atatcttccc 71580
ttccttatta agctttttgt ctaattttta ttaattattg agaaaaggga attgaaaata 71640 ttaactttg attgtggatt tgtctgattt tccatttggt tttgggtttt ttgcttcata 71700
tattttaaag ctttattatt atgggcttat acattgatta ttgttagatc ttccctgttt 71760
aattgacctt ttaatcttac tgaaatatcc ctcattatct ctgatagtgc tttttgtctt 71820
gaagtttatt ttgtctgata ttagagcaaa tctttcttat gcttactgtt ttcatggtat 71880
atgtttggct ttcctttatt ttcagtctgt tgtctgtatt tttaaagtac atctctagta 71940
gacaacatac acttgggctt cactatttta tttagtgtat ctctgattgt taattagagt 72000
gcttcatcca tttctatgta ataaatcatt ggtatagttg gattttaatc caccatttcc 72060
ttacttgttt tttatctgtc ccatttgtgt attgaccttc tgttccttat ttctagccct 72120
ttttttttgg ttaattattt tttttctagt gtttaattag tgttggattt tcaacagcac 72180
ccttttgcat tattttgtgg ttattttgga aattaaagta tacactttaa cttgtaatat 72240
tctacttaga gttactattg tagcacttga gaaaaaaatg caagaacctt gaaacagggt 72300
agttttattt acccataccc atcttttgtg tcatcattga catatattaa catatctaca 72360
tcagttataa atttcacaat acagtctaca atacacaatg cagttcaatt atttctttga 72420
actgtcatac gtattttaaa gtaagagaag aagaaatata ttgtctttta tattaacctg 72480
catatttatt atttcctgta cccttcattc cctcttgtca gtccaggttt ccatttggta 72540
ttaatttcct tcaggctgaa aaacattcta tagcatctct tataatacag atctgctggc 72600
aacaaattct tttttctttt taattggaaa atatctttgt tttgtcttcc atgtagcagg 72660
tactttttac tagatattga agtctgggta cacaggattt tttttctttt agtcttttaa 72720
aaatatcact atagtattcc tgcagttatt gtttctgaaa aaaataaaaa aggtagccac 72780
catttgtctt atttttaccc tgtatgtaca gggtcatttc ttcctctgcg ttctttcaaa 72840
gtgttctcct ttttaacatt tgagctagaa tatgcctatg agtggttttc tttgtattta 72900
tctttcttga gatttgtcaa gcttttggat ctatatattt gttttccctc aaatttgggg 72960
aaaaaatagt cataaatttt tcaaattttt taatccattt tatctatcct ctcattctga 73020
gatactactt gcatatatgt tagcagattg ctagtgtgtc ataggtcgca gaagttttgt 73080

-continued

```
tcatttattt atcctctttt ctctgtgttc ttctgagtaa tttctacttg tctgctttca  73140
agttcattga ccttttgttc tgccatctct gatctgctga atttttcatc cagtgaatta  73200
ttctatttat gaatttatat tttctgttct agaatgtcca gttaattgtt taatgtattt  73260
catatttctc tgctggaatt ttccatctgc atactcatta tgaaaaaaaa ttctttttttg  73320
tcacttaaat ataatagctg ctctaaagtt cttgtctcca aatttcaaca cataggtcat  73380
ctcagagttg atgtctattg acttcttcct ctctgattag ggtcacatt tcctttttaaa  73440
tggttagtga ttgtttaata tatgctggat attatgaatt ctatgctgtt gaatatcttt  73500
cagattctat agcgtttctt tagaggctat tgaattgtgt tttggtagga ggttcgaata  73560
gtagcagatg aggtttatct tttctcccag ccttgttttt aaactttctt gggtacaagg  73620
gaaagtagcc ttattcctaa ggcatggaat atctgagata tctgtaaagt gctcagaaaa  73680
tctctccaat attgcttgtc ttaataattt tgtccccatt gttctgtgtc tgctagggcc  73740
tctactaaga ttatagcttc ccatgagttt ggtgtttggt tatttttttt tattataatt  73800
ttattttttg gtcaggtttt gtgacttctc tactggtgca tatacagctt attattggac  73860
cagtaactta aggagattca tctagggatt tctgatgctc cttctttgca cagctcccctt  73920
cttccaaata acctagatct agaaactcca gctgcatcgg cagccctgaa cttcaatctc  73980
tgactcctta gcttagtgag gccattggtc cttgtttgaa ctctgtcttc cacacctcaa  74040
tctgaaagtg caccccagac aggagagctg aaagccagaa aaccagggca aacatgagcc  74100
tcacttagtg tggatgccct gtctcgtgaa ttacacattt gtactgctgt tcactaattt  74160
ctgaaaagag ttgcctcata atttgtctag aattataatt acttaggttg gaaaggctag  74220
tctgctacca tcgtatttgg aaacaaaagt ctttcctact aattttaaaa gacaaactaa  74280
atataaaata cctattcaat cccgtgcctc tgaatctgag attacttttt aaattgcaag  74340
atgaatggac agccttcttt tttgttcact gtttcttttt tcttcctttt taaaaaattt  74400
tgagtcttgc attgtcagca acttttagct aggtgatgtc actcatgaat atgccactta  74460
gatacctctg cacaggacaa gattttgtgg tgctaacatt cagagagaaa cagacgtaaa  74520
taaaatactc atagtacagt atacaatatg tatcataata gaattatgca aatgttttta  74580
ggtgtagcac aaagggggta agactttttt gggagaaggg ttagggaaat ttgaagaaag  74640
catgctagtt ttcagggata actcaaaagc tggccatgtc agagtaccag ggcatatgaa  74700
aacttattac agagatgtga gtgtgtaagg aaaagtcatg ggagaatgga ataacataca  74760
aacctattag ttatccaaag ggaattatgt ttatagcata acagtaatat cctttatgat  74820
aagcaaagag aatgtttaaa agatgtttta tgtttgagat tcttgcagac agtacctaaa  74880
tgatagagaa agaaatccta actttgacat tatcttatac attttctaga aatagtcttg  74940
acccaacctt cctggactca tataccagtc aagttaaact cttttgactc ttcggtcaaa  75000
tggaagatca taatacctcc ttcacagagt ttctgtgagt tttaagtgag ttagtacaca  75060
tgtgcttgga gacataactg atgtcttata agagttcatc attaagtact agaacaatga  75120
gatgcaataa gactttggat cagtaattat gttgaacctt tagtgagctc tggatctgaa  75180
tcaaggaaga atactcattt gcttgtttca taagcaccaa gataaccatg tcacaggcat  75240
ggtgctccta aaaatgctca ctctaaaaag aagttcagca aaattatagc acaattcttt  75300
gtgttctgta tttctacaga tgttggttat tattagtcaa atgaaacaag tcagttccca  75360
agatttctgg acagtgaata gttttggtaa taaggagata taattaatat ggtaataacc  75420
caggaatttg ggattactca aatccggccc agatgagctt cctctccaca taaattctct  75480
```

gcaggctatc tttgcataaa atcaaaactt tgttgtcagc ttaagttttg tccccaaata 75540
cccttcattt gggccttgag gcatgcaatt caaatctcat tgattcctac tcgatagctg 75600
cagtggaaag tattgaaagt cattccctgg aggtataagc aaatctcttc tgataaagtt 75660
ctttttgtct gcctgcaaga gggacagtag tatccctgat ggaccaaagg cctggttctt 75720
aagccccacg catgaacaag tgaaataaaa aaagtgaggt aacattgacc tctatgggag 75780
gtgaagctca gtaacctatg ggcgcttccc ccaaccctcc tctccactgc cgccccgcca 75840
tccagtcttt gctgtttctc tccctccctg tctcctgcag gaagattgct gctgtgtctt 75900
agtcagactc caggattgtg tattggctca cagtcttagg gatggaactg tcaacatggt 75960
agtcaccgca ctctcagaga gcaagtctga gctttcttta gtaaggcctc ccacacagct 76020
ttgttggaag cccccttcctt agatgctatc cttctgcctg agaaaggttt taggtagcaa 76080
attccagaat atctcactct ttagtaagct gctttttgct tttgagtctg gtctttcctt 76140
tggtctgagt ggtgaatttc aagacttagg tttggtcttt gtatagaaca agaagaacat 76200
ggtgtttggc taccttgatt acagggcatc tggctgaccc aacgtagata atggagttct 76260
ccatagcatc ttcctagctt gttagagttt tccattggat tttaaggaca aaatcttaat 76320
taatttattt gttctctctg tgtacattga ttatggcctc ttaaggaggt tacctagtaa 76380
atctattgta attacatacc agcaatccca atagataatg ggggccacag cagattggcc 76440
ttcaaggaga accaaaacag ccaaatgatt tatttacaaa cagtattatt aaaattcctc 76500
aaatggtgcg aattgtttgt aaccctgaat ccatttcata tagagagcac ttttatagat 76560
agtagttaaa tcccaaacga gtccacgtaa tcttacataa tccttaaaat agctctgtta 76620
ttgtaatgat agtactttaa ttataccaaa tcccatttta ttactcagat ttattttggt 76680
gagaaaattc acattgggct ccaacttgag atggtaaaac atatctccca tggggctata 76740
ggatgtgggg tgggccagga ggaggaatcc taaggaggat attcatggtt atgtgaatgg 76800
aagaccctat ttctgacaac tccctacgtg gggatcacca gcaccttatt gttcatccct 76860
cactgtctcc tcccccaaca cacacacaca cacacacaca cacacgtgag cacacatcca 76920
tacatcccat cattagagtc tccttggaaa cataccattt ataggatgag ggaatttcct 76980
gctctcagtt cacatatggt agaggaatgg gctgttcctg tcctcaccat agtagataaa 77040
atctatttct gacttatcaa gttaaatcta tgaattaatt tttccctgta agatgttgat 77100
acacacatag tagatctatt attttatatt atgtactcta ggtactttgt atgttaaata 77160
ggtataggta tatagaaaaa tctgtcaaaa taagtttcat gttggaagag acccttgtgg 77220
gagatgtgtt ttgtttattt aattcgtgaa tcattctgct cctttttttt ttttaaagac 77280
agagtcttgc tctgttgccc aggctggagt gcagtgacat gatctcggct cattacgact 77340
tccgcctccc gggttcatgc gattctcctg cctcagcctc cgtagtagcc gggattacag 77400
gcatgcgcca ccacacccag ctaatttttg tatttttagt agagacgggg ttttaccgtg 77460
ttggctgggc tggtcttgaa ctctggatct caggtgatct gcttgactcg gcctcccaaa 77520
gtgctgggat tacaggggtg agccaccaca tccaacctaa attcatgaat cattttgctt 77580
ctcatggaag agccaggcag gatcaagaaa ggtgtcccaa accaattcca tatatgttct 77640
ctctcattga gtttcttatt tagacgtagt atgggacaac actagtgcct tcaaccattc 77700
cccttagtgt tagtcttaag ctttccaaca ttaaaagtcc aaactcttag tccgttgcac 77760
agtggcatcc gacaaatgtg tgttgaagat atgaacgtgg aaacagccat gattctaagc 77820

```
atgagatacc taaaaatact ataaccacag tgcacataca attatttaat attttcaaca  77880
gtccaaacat agctgaatgc atacagatct tgatccaggt tgtaaaatgt catgtttaaa  77940
atttctgagc aagctgtcaa gagtgagaaa gcaaaaagat tttagaagat aaaggcatgg  78000
gagatagatt tgcttgatag tataagtcat tttcccccca gaaatatatt aagtctgtgt  78060
tccatatgtg tcagaattac ccaagccaga tctctttctg tctctgtgat ttctttcttt  78120
tttaatgcat tcatcttttg gagactacat ggatttatat tgccttgcaa aagcaatatt  78180
cagcagaaaa atcaatcttt tgaatacttt aaacagatat aggtccagaa tgtgttacag  78240
aaacagttaa aaacaaccac agcataagag caaaacttct agaatggata tgctgtattc  78300
atcagtgtgt tctttaaatt atagggaagg ccaaaaatcc ccctggagac tccagcctac  78360
actgggcagc catggcattg ccagcattgt tttctcttat aattggcttt gcttttggag  78420
ccttatactg gaaggtaagt ggtaccattc cttttttaa aaatatgcta tgtttacata  78480
aattatcatc ttttttcct caagaaatga tcctttaaga aaacagtgaa ttctacctta  78540
gcttataatc taaacaaaat ttaaatttta taaagtttcc tgtttctcat tatgtctgga  78600
gacaatccct ctagctgata attcacgctt aagaattagg aactggtgtt aatagcctga  78660
actaaatatg aaaaggaaga tctgacgaaa atcatatgat atacttaaaa gacaaataga  78720
aatgtcattt gtattatctg ctattttgga tttctactct tttgttctct tcttattgaa  78780
gcctgtctaa aattttaaaa tgtgcaaaaa tcattgtgac tcagcttctt gaaatgtctt  78840
ttgaatttga ttaagtgtca gcttctttat tactctttag cccccaacat cctaaaaatg  78900
ttgagttgat agtaccatgc agctttcata atttttttatt acaaagatat tttgcatgct  78960
acatgctgaa aaaactgtta ttggagttat tgccataaaa gataaaagtg gagtccactt  79020
acctcttaaa tattagacca ttcattgatt attttacagt atatgtcttt cttctttttc  79080
cagaagagac agccaagtct tacaagggca gttgaaaata tacaaattaa tgaagaggat  79140
aatgagataa ggtattttgt tttgctaaat gtgtgcccaa tcaagcatga cattgccatt  79200
tcacacactg tgtacctgcc cataatgtct ttaagaagtc cttcactcat gacagtagct  79260
cctaaccagt gagtcccaac tctatccatg tttctgatgt ctcactctct cttcagtgct  79320
gcatctccat ttacctacag aataccttca cataattgtc ttcatgactc ttcttagggt  79380
ttgtaaaggg gttacctctg ctttcttatt taagtaaggc agcagaatct tctcagactc  79440
ctggttgtgg aactctggag gcacatttgc tcatgttctg tcttttccac acttttatca  79500
aaacatactg attcagctct tggagcgtct tcctaagctt agttctttca gtaggaagca  79560
ttatcatcac tgacatcttt atgatctcat gagttgctgc cactgatctt ttctttagcc  79620
cttctaaact caacctttag tcacactctt ctgtaaaccc tggttcatag tgtgacttct  79680
tattcaaaat acgttcagtg attttctctt gtatatttta tatatctttt attttactct  79740
ggctttcaga gcccttaact attctcaaca tactcgttgt tttctctaaa gctgaataca  79800
aaatttgctg taagatgact ttccattcac tgtagctggc tcttgtcatt ctttcacctt  79860
accctatact gcccagcact catatgttcc cttacctttg attataattt tcatttggtg  79920
tgttgccttc tctcatgtca tgcctgtatg tatacacaga cacatatgaa atgcatatag  79980
gcatgcttgg tatgtgtata tgcatataca gagaaagaaa tgttttaact acttggaaag  80040
actaccttaa gacaaatgaa gtcttccctc ttccctatag taataagaag gtaggctccc  80100
cattcaattt tgcaatcttc tgctactata tttacagaaa agctgccttt tacaatgccg  80160
agatcatggt gtacctcaga atctctgacc aagagcaaat aagcattttt tcttattgtt  80220
```

```
tttcagtatg ttgcaagaga aagagagaga gtttcaagaa gtgtaattgt ggcttgtatc  80280
aacactgtta ctttcgtaca ttggtaagtt tttttcttct ttcctttttt tttctttttt  80340
ttattatact ttaagttcta gggtacatgt gcacaatgtg caggtttgtt acgtatgttt  80400
acatgtgcca tgttggtgtg ctgcacccat taactcgtca tttacattag gtatatctcc  80460
taatgctatc ccttccccct ccccccaccc catgacaggc tccattgtgt ggtgttccct  80520
accctgtgtc caagtgttct cattgttcaa ttcccaccta tgagtgagaa cacgcagtgt  80580
ttggttttct gtccttgcga tagtttgctc agaatgatgg tttccagcct cagtcataca  80640
tgtgcatgtg tctttagagc agcatgattt ataattttat aatcctttgg gtatataccc  80700
agtaatggga tgcctgggtc aaatggtgtt tctagttcta gatccctgag gaatcaccac  80760
actgacttcc acaatggttg aactacttta cagtcccacc aacagtgtaa aagtgttcct  80820
atttctccac atcctctgca gcacctgttg tttcctgact ttttaatgat caccattcta  80880
actggtgtga gatggttatc tcattgtggt tttgatttgc atttctctga tggccagtga  80940
tgatgagcat tttttcacgt gtctgttggc tgcataaata tcttcttttg agaagtgtct  81000
gttcatatcc ttcgcccact ttttgatggg gttgtttgat tttttcttgt aaatttgttt  81060
aagttctttg cagattctgg atattagtcc tttgtcagat gggtagattg taaaaatttt  81120
aattcaaact gaaatattta gcaagaacta tacagcatat gagatgccaa agtttagaaa  81180
caaacttcat tagtaagtct tctatcaagc agatgtcagt atgttggctg aagctgttac  81240
ataattgaaa tgtgcatatc taattcattg tgtattctcc agttttgaaa ggtaagcagt  81300
gtttgtcctg actagtggat tcatctagtg tgggatatgc acaaaaaatta acagttgtat  81360
gtttacttag actgtttttg agaccagaaa attaattaga caagggaaat atagcaaatt  81420
aggactaaaa ttaagtatta ctaatagaat aaaaatatat ggaatcaatt ttatttaggt  81480
gtgaccacta taacatgact gtatcccatg tgttagatgc tgaaacaaga gaaaaccaga  81540
atgtttccct gccattttca ggaaaaagag aaaacatcca aatatcttag agtcaggaga  81600
gtaagatttt ccaggtcaat tgccaccttc cacatgacta gtaataatta tgcattataa  81660
tagttcagag cccaggatgc acggaacata aacgcatggc agacaggtgc tgtgactgtg  81720
tgggtctgcg gagggattgt gggagaaagg agagtaagat gtggctagaa ggtactggta  81780
tcattatctc ctgtcccgtc tgctttctct gctcccttgc tgcagatact gttgcgggaa  81840
gacccacagc tgcattaact taatcagtat tgattcatgc tgtccctcac ttttgcttct  81900
gctaattggc tgttattttt gttactggca tggaatcctg agagcattta ccacagttgc  81960
atgcgaatat tctctcctct ttcaaattcc tcatttcttc tgtgcattcc ctcattgtca  82020
aaggattatt tactctcctc tttattacct agatagtctg tggtggattc cttctttacc  82080
ctgcaagtca ctgcccttcc agctttaact cctgtcccag gttcagagat ttgtctctag  82140
acttaatctt cttcagtgga actgagtcat aaattatctt gcctcctgta tgagcttact  82200
tttatggtta tacagcaaca ttttttaaca actcaagata acatgatata attatgttgc  82260
acatttctct aacactgtaa tactttattc tacacactct gtcactttta ccttcaatca  82320
tactcttgat taacatgtcc gtagcatgaa tagcaccctc tattttctgc tgcccattgc  82380
cacttctttc taggctcatt cttcctgtca aataatgtaa atggatagac cgtttgcttg  82440
acacttttta ttttccgaag caatatttcc caagctgaaa ccatgctttt tcctagaaat  82500
tcattttttt gcctttgaac cataagatga gattcactgt tttctttttt ttttccttcc  82560
```

```
ttttcttctt cttgacagcc atttcagttc tctcaagtgg cattcacaaa ccacacatta  82620
aatggttaat tgagtcttaa atgctcaaat gctcaagtaa tgtcctctgt tgtttggttt  82680
gggattgcat tgctgggatc ctgttttggc acacaggtct ttaatcatgt ggttttaatt  82740
acgacattcg tcccatgaca tttgggagtg gattaggata cggaaaccca ggccatttgt  82800
ttaggaggaa aaaagatggt attttaaagc aaccatagtc aaacaactta tgaatgtgtt  82860
gaatagtcag ttagcattcc aagaaaagag ttaggtcttt ctgtttcttg ctgtaccctc  82920
aacacctaac ttgctgcccg tgcattgttg gctctctata aatgtttgtt gaatgagaga  82980
ctgagtgagt gactcagccc taaatgaaag tttaagcaaa tggcaaagaa gattgttctt  83040
ctgaagtagg gtttgttttt atcttttgtg tgaatgtgtg tatttaatgt attgggttgg  83100
attaatgaga cagcaaggta tgcatatcaa gggggaatat aatcacatga gaaattaact  83160
aataaattat ttttcttaag gtatgaatta ttactcatgt ataaaatgaa tcacattagc  83220
caggttaaag aagccagaat tatccagaaa aaaacccagc tcacttattc agtagtcaat  83280
gggaaataga tggcagaatg aatgaaaaca tgactcattc tccttcacaa agtgccttac  83340
tcgtcatctc tgcaaagctc caccaaggct caggtcacat actgccacct acaaaaacct  83400
gacttcccaa atgaaaataa tctctatttc tggccctcta aatagatttc atatgacact  83460
tggtaggaca tcacagtcac ctaaatgaac attttgtgcc cttttcaaaa ccataaactc  83520
ttagggggca ggattttttt ttcttaattt agttttggag ccccactaaa caatgtcact  83580
tatactgtgc acatataaat gatgaataac tatttgttga ataaattaat ggaaagatga  83640
atgaatatct cagaattaca ataagatgag aataaaatat atgaaaataa aaacagaaat  83700
aaacttgtat gtgtctatga gtacataaga attcaaatgc tgagggaaaa gtaggaaaag  83760
aggtagaaaa gggccagttc gtcctcagaa tctgaaaacc ccaaagtaaa aatgtgtgta  83820
tatcatttgt aatcatctat tgactaccca ttatatgaag taaaccctta catttggcct  83880
tctaccagca gagatggaaa accctccaag gaactcttaa gtctagttcc tagataggtg  83940
tgtagtagag ggaaggtctg ggagaacaaa ctgtgatgtg gttggagaga aaatcttcta  84000
aaaaataaga ataaccgtag taaaaaatgc caagacagaa ataaaatgtg gagttgcaat  84060
tatacattta aaaaatagat ataatttgga ttataatcat tttcttggtt aacaaggaag  84120
gggaaaaata caaggaatga ctcaggttta tggcaaggat ttctccctga aatggaagtt  84180
tcaccaacta aaacaaatta aatcaagaca aatattggaa cactagaata gagaacatat  84240
gggctagttc tcttaaggaa ataacctata attggaaaat gaaaagaagg agggtttaat  84300
atcttaacta caaggaacaa acgtggaagg aatgtattga actagaaaca acaacaaaaa  84360
aagttgcacc taggaataaa taggccagga gtggtagctc attcctgtaa tcccagtacc  84420
ttggggggct gaggtgggag gatcacttga gcccaggagt tcgagaccag cctgggaaac  84480
ataggaagac cccatctcta caaataattt aaaaattggg tgggcatagt ggtatgcacc  84540
tatggtctca gctactcagg aggctgaggc aggaggattg cctgagcccg agaggttgag  84600
gctgtaataa gccatgatca aatcacagca ttccaacctg ggtgatagag caaggcctgg  84660
tctcaaaata taaaaataaa aaattaactg aagtgtgttt atttgacacc atgcgtgaga  84720
acagctatgt gaaaagttaa aaatttactt ggtcacatag cttatgccaa atatccatag  84780
tagcatccta caaaaacctt tttcatattg ggttgtggat agcaaagatt aagatagata  84840
aataaaacag atggattaca ttaaaaactt tatgttaata cgttacagga aacttttgct  84900
ctttactctt cccacaaatg tgattccaac aaactctagc aggtgcattg atggatgcaa  84960
```

```
agcttaatat aactttgttg tgtcctcaaa ttgtttatag cctacaaaag gaaatcagac  85020
atatacataa taaccaattt ttaaaagtga actaaaagtt tacagagtta ctttgatcaa  85080
agtccaggcc tctgcatatg ttcatacaag ttgtgaattc aacacagttc tagatactgg  85140
aatgaatgac atattagaat tgagcacacc caaatacagt tacctatttt tgaaaggaga  85200
gagaaatcac taacaatagg agaaaagctt cactttgtaa gtggtggagg tagcatctgt  85260
actgagcaca tggcgtaaac taagtcagta tagtcccaaa gtagaaactg tgttcaaggg  85320
tcagtttgga cagttggatt ccagtggaag tcacatataa agagttaaat gctgagaaga  85380
aagggtgagc atcggtttga gaaagggttt gaattccagg aatggggctt aaatgccttg  85440
tgtcacataa ggaggtattg ggagaaaatg gtgtaggaaa gatgtgggtg acaatcaaag  85500
ctgaggtgtg agaaaactaa tcgggtgttg gtatggcaag atgtacggga gtggttaact  85560
agagaaattg agtccactta ccaggccagt ctttaaataa gatgtgagag agaatgacaa  85620
ctgaattagc atcagggcca ggaaataaga aagcatagac catttgaaga cattgcagta  85680
aaagaatcaa caaatcctag ttactaatgg gatgtgagac ttggcatcac aggcagaact  85740
caagaatgat ttggagacta tgggacttac cagagtgcgg tggcattaac aggaaatgga  85800
aaatcaggag aagaagctgt tggtaaatat tattgaaact aaccagtggc caaatatgtt  85860
agactggaac ttcagataac agtcaggcct ggaaagaatg atttgcaatt tgagagttat  85920
ctgcaaagaa tcttatttga gaccttgaaa gagaaattgc ttagtcacag aaatggcccc  85980
gtgtggttga tagtaaatag catgggtttg attgtggaga ggttcactaa agaaatacaa  86040
acaaaatttt ggtatatctg agctaagggg gaagaaaata aatcttagaa ttggaataaa  86100
ggacaagctg aagacaagct tggaaattta ggcctcaagg cttggcaatg gttggttacc  86160
aaatagcaag acctgtgatt ctttgctaga tgtttcctaa gactttcaaa gctttgggag  86220
tttggtttct gtagatacat tgtaaagcag atgattagaa aggattaggc ttggattcaa  86280
gccttgactc tttggtgtag aatactagat gaatttatat cagttatcag ttcatgtctt  86340
ttaaaccctg gtttttcatg tgtaatgagg gttagtgata aatgtactct tcttatttca  86400
caagggttct tgcaagaacc caggttatca ttataaaaat tgtagttttg ttctatggga  86460
aaacaggtgc cagtctttac gtttattttc tttgctaagt gacccgggga caaaaatcaa  86520
aaatagattt ccaatcttct ctacatttaa ttctctctct ctctctttct ttcttgagag  86580
tctttctttc ttaagagtct tgctctgtag cccaggctgg agtgcagtgg cgtgatctca  86640
gctcactgca acctccgcct cctgggttga agggggtttt gtgcctcacc cccagagtag  86700
ctgggactac agatgtgcac taacacaccc agctaatttt tgtattttta gtagagacag  86760
ggtttcacca tgttggccag gctggtctca aactcctgac ttcagatgat ccgcctacct  86820
cagcctctca aagtgctggg attacaggtg tgagccacca tgcctgtcct atatttaatt  86880
ctctatatta agctttgtgt ttccaattat ttatacattt aaaaaataca tccttttgct  86940
ttttgtgatt ccccttttgct ttctaaccat gcttttaaaa tatcttctat atattttgga  87000
tttctgaagt tttatcttag tatctcttaa tttttgttct agatttaatt ctgatttcct  87060
aaatacaggt tgtctagctt ctagagttct ctgcttggta aattgttgta taagacagtt  87120
tttaatatat tacatttaga gagactggaa aaatattgca attcttatta cactatggaa  87180
ttttatggct aatctgtgta atgatctcaa tactttaaaa acagtgatct gtgatgctgg  87240
gttgataaac aaggacaaaa gtagtgaaag agattgagca gagaagacga gaaatgcaaa  87300
```

```
acacatttat ttagagactg ggattgaaga tgggatgata ccatctatat gtattttttt  87360
taagtagaga aggaaataca aatactttac tggaaagttg aaacatctga aagctagtag  87420
attaacacaa gtactgaata actaaaacaa aatatggctt tcatgcttca acaagtacaa  87480
taagctatgc tgaggccaaa cgaactttcc ccagaacttt gttgggatgc ggtgccaaga  87540
ttacagtctt tcttttttg gttggaagta ttgaacgaaa tctttctgct gctatttcct  87600
cagctggaag aaatgattgc tagaacctaa ctagatagtc aagatactag agcggctcag  87660
tggccatgtg aggctattac ttgttggtgg ccattgacca gcttctccac ctgtcttagg  87720
gatctctttc atgctactcc atctatctcc atttctctaa tctccactct ccagacactt  87780
tgttcgtcaa tccttctccc ttcacccctg tttactacct tttataatct tgctagagaa  87840
attcaaagct aactaagttg ataattatat tatcacaaac tgagatcatt ggtagaatgt  87900
caggaggtat gaaagtcaca gggtgaaata tttattgagt gtctattaag tgccagacat  87960
tattataaga gtggaggtac agcagtaaaa gagatagaga agctccctgc cctcatggag  88020
cttacatttt aatgggagga catagataat aaacaaaaag taagattgtt tcagataatg  88080
tgttaccaag gagatcatag aaaatgactg atcactgcat ctaagaaaat atttatgaag  88140
ttcttttctg ctatataagt gaagcataca ttgcaaattt gttactcatt ctgtggtcat  88200
atatgatttc ggctattgag atttttaaaa aggcagaagg cagatacacc ataatctctc  88260
ttttcttcct tcctttctag gctggtaaca gttcatgttt gcttcataaa tgaagcagct  88320
ttaaacaaat tcatattctg tctggagtga cagaccacat ctttatctgt tcttgctacc  88380
catgacttta tatggatgat tcagaaattg gaacagaatg ttttactgtg aaactggcac  88440
tgaattaatc atctataaag aagaacttgc atggagcagg actctatttt aaggactgcg  88500
ggacttgggt ctcatttaga acttgcagct gatgttggaa gagaaagcac gtgtctcaga  88560
ctgcatgtac catttgcatg gctccagaaa tgtctaaatg ctgaaaaaac acctagcttt  88620
attcttcaga tacaaactgc agcctgtagt tatcctggtc tctgcaagta gatttcagct  88680
tggatagtga gggtaacaat ttttctcaaa gggatctgga aaaaatgttt aaaactcagt  88740
agtgtcagcc actgtacagt gtagaaagca gtgggaactg tgattggatt tggcaacatg  88800
tcagctttat agttgccgat tagtgatatg ggtctgattt cgatctcttc ctgatgtaaa  88860
ccatgctcac ccatatccca ctatacaaat gcaaatggtt gcctggttcc atttatgcaa  88920
gggagccagt actgaattat gccttggcag aggggagact ccaaaagagt catcgcagga  88980
agaagttaag aacactgaac atcagaacag tctgccaaga aggacattgg catcctggga  89040
aagtccgcct tttcccttga ccactatagg gtgtataaat cgtgtttgca aaatgtgtta  89100
tgatgtgttt atattctaaa actattacag agctatgtaa agggacttag gagaaaatgc  89160
tgaatgtaag atggtcccat ttcaatttcc accatgggag agcctaaaaa taaattatga  89220
catttagtat ctaaggttag aaaaccacgc ccacatgcta atatgggtgt tgaaaactag  89280
gttacttata atgcaaggaa tcaggaaact ttagttattt atagtataat caccattatc  89340
tgtttaaagg atccatttag ttaaaatcgg gcactctata ttcattaagg tttatgaatt  89400
aaaaagaaag ctttatgtag ttatgcatgt cagtttgcta tttaaaatgt gtgacagtgt  89460
ttgtcatatt aagagtgaat ttggcaggaa ttcccaagat ggacattgtg cttttaaact  89520
agaacttgta agacattatg tgaatatccc ttgccaattt tttttataat aagaaaacat  89580
ctgactaaag tcaaagaatg atttcttatg gtttattttg atgaaagttc ttttaacatg  89640
tcttgaatgt acacataaag gaatccaaag ctttccattc taacttaatc tttgtgataa  89700
```

```
cattattgcc atgttctaca accgtaagat gacagttttc aatgtagtga cacaaaaggg  89760
catgaaaaac taactgctag ctttcctttc atttcaaaag tccaagaatt tctagtatat  89820
ttggatttta gcttctgttc aaagcaaatc cagatgcaac tccagtaagt ggcctttgct  89880
ctttttgta ccaaagagcc cagatgattc ctacagtccc tttcttctct aacatgctgt  89940
ggttccttaa atatgagtaa tttctctaag atataaccca ggtgctttga gaagctgcat  90000
taaggtgttc aggccctcag atatcacatg gtacacttga ttagtaataa aaccagagat  90060
caatttaaat tgctgatagg tcctgtctca gtgtgtggca ttgactgttt tcaggaaaat  90120
agatacagat taatatgagt tatgcgtgta ggttgtgtat agattgagaa gatagatact  90180
tctcaatcta gtagtttgat ttatttaacc aatggtttca gtttgcttga gcatatgaaa  90240
atcctgctta atgtgcttaa gagtataata aatgtgtact tttgtcctca aacctagtag  90300
ctgggtttta acactcatgg acatggtctt aatcaatgga gttaaataaa caaattcagc  90360
aagttattaa atctgacatg gtaggagagg ggagatgtgt cctgcttatt aaatgtgttg  90420
gtccattgaa agttacatgg attgccaatt tttaaaacac taaagttgaa taaaatgcat  90480
gaacaataga aaaatgctga acattatttt ggatgctagc tgcttggaca ttaactgtgt  90540
tatttctgct ttgagatgaa aatatatatt tatctttgct tattttatcc cagatgtgtt  90600
ctgaatatcc ttcttcataa atcatggaaa actcactgct gagatagtaa accatgaaat  90660
cgccttttca gttggtgcca tgtatctgac agttccatct tggaaggttt caaaattacc  90720
ttttaaaatg atctcagaag tctgtagatt ctcaatgata ctgaaagctt tgcacctctt  90780
tggtagaaac caggtctatt tagaaaatgg ctttatgata aatgttgcct cctgagtgat  90840
aatgaagtgt tcctggatat tgtattgtaa tttaatgtgc ttaccacact gccacatttt  90900
aatgagtcag agaaaaatta atttttcttc aatacaataa tagaacaagt agcctattct  90960
cttaaaaagt atgtgaaaag aaaattatga aaaaatatgc atacctaatg aagtattggt  91020
tttagtaaga attaaataca tttcattgag ctttaaagta ctttggagaa actttggggc  91080
acgttttcct actctaattc aactaaagtt ataaataaag agaaaaactc attcagaaat  91140
catggatttt aaaaatattt tactgcagcc aagttttcat ttcaaaatgt aatttcagtt  91200
tggagctttt aggcattatg tatatttaaa aaatatattc ttcaaaaatg cattttggca  91260
tggtgggatg gatgttgcaa aagatatccg gagcctccag tctgtcatta actgatatgg  91320
taaatcacct ctcttctttg ggtctcaatt ttttatttat ctatatggta aactcagaga  91380
tcactcctta ggggtgagtc ctattgcaat atgaccgaca aagaagacaa aatagcattg  91440
aaactaaccc atacaaaata tccaactctg gattctgtga ataagtatct tgaccataaa  91500
aagtcattgc tgttcttgtt tctaatgtaa atagtgtcca ttagtaaaag tgaaattcag  91560
tcttaagtag ggtgaattgg atcaccattt acacaagaga tggctttttc ctttgcttga  91620
ataaacattt tggatcacct ccaaagaatg aaaaccagta gtacgtttta gtcatattag  91680
tcaggatgag aaactataag atgtgtgtaa catttggaaa tgcaccaaag tgagcgttta  91740
aatcttctca ttttattgaa aactaagagc agaaaatgta aaatgctcat gaaggttttg  91800
aatgccaaaa gatattttag aatcaattta taaaggggta attcattaat tacactttaa  91860
aattggaaag tgggataaga aatctaaagt aaaccagctt atctttgaaa caatattatt  91920
ttgaaattgg ctttaaaata aaaccattca gattgaaatt ctaattagct catttgtgga  91980
gtttgatcac acaattcata atgttgctgc tttccattaa ctagtcttga aatgcctttg  92040
```

```
tttgtaaaaa taaaataatg gtactttcat tttataacaa ggtgtttttt tcaagaaata  92100
atccatgcta aaatggatat ttgtgatcct gaaatgttta ctaagcattg taaatttatt  92160
tataactgcc atctccaact acatccttat gatgttttta acaataaaat taaaacaact  92220
gttaaactaa aaaccacacc gttttccagt acttgatctc tgagctacaa tactcactaa  92280
atataatttt ccaatcaaaa tattctattc tatattctaa gggttaatat gtgattatag  92340
tgtccacttg ccaccatttt tttaaatcaa tggacttgaa aagtattaat ttagatggat  92400
gcgcagatat accctcagtt cagtcataga ttggagtttg catataataa tgtaaatgta  92460
tgtcgacact attctaaata gttctattat gactgaaatt taattaaata aaaaaggttg  92520
taaaatgtga tgtgtatgtg tatatactgt atgtgtactt tttaaaatag gtgtatgtcc  92580
caacccttt ttatacaggt ttgaatttaa aattacatga tatatacata tactttattg  92640
ttctaaataa agaattttat gcactctcat aaatttaccc tgtcatttta tatcttaagg  92700
ttatcacata tgtctacaac atggttgaac atttattaag ctacagtcaa aattttctgt  92760
ggaaactttt gtcattaatc tagattttat taagctacag tcaaaatttt ctatggaaac  92820
ttttgtcatt aatctagatt ttgttgaaat atggacacaa ggggataaga aattatttaa  92880
attcaataaa tatttattga ttactaaaat aagtaatcaa ggaaaataaa aaatgaatta  92940
acacgacgtt tgctttcaag agatttataa cttgtctgga gaaaagaaat gcaatagata  93000
tatagaaaag cactataata gatatagata cagaaaatag atacagatat agaaaagcag  93060
tataatatgt atagtccctg aagtaaatac ctacatgcaa aacagaggtc cagttaatgt  93120
gcttagggca tgcaggaagg agaaatggat acagaataag ggagactgtg gaggaattga  93180
tgtttgggct aatacttaga aggatgagac aaatttttat agtgagaatt atgcccagtc  93240
agggcagcat tttccataga aagaagttat aaaatttcta agcttatttt accaactcaa  93300
acaggtatgt ccttagcata caccaaataa aaagacacac ggagagataa gaccagaccc  93360
ttcaatgtaa cagtgagtgc agacactatt cttagggtcc ctgagaagcc tagactcctt  93420
tgcttgtttc tgagaagagg aatgacgaga tcaaaacgca ctacggatcc tgtgatttag  93480
gcagtagata atcatcctgc ttaaccactg gttgctattt gactctcaag cacataccct  93540
tgctatatga caccacactt attcacccac catttctttt cagaatttgc tgattctctc  93600
tcctctgttt accttttata ttgccaactt cgaccaatat atgactagat aactagaata  93660
gcctcctaac tgatcacatg attctacttt cacccttttt caatcagttc atcacattat  93720
agtcaataat agggagacat ctggtgtgtg tgtgtgtgtg tatgtgtgtg tgtgtgtgtg  93780
tgtgtgtgtg tgtgtttctg gctaaaacac ttggatggct tctcattatt ttttagctaa  93840
agcccaaact cttcaacaca gcctacaagg ctctacttga gccatctcat ctttttttgtt  93900
ttgttttgtt ttggattgct gattgttttt gcctttaatc cataaacaac atgaaggttg  93960
ggcccataaa tactaatata actgcagtcc taaaatttag tgcaaattat tagtggaatt  94020
gaaacaaaat gtgatctaaa tagctatcac ctgttgtact gagaagttat tttttaagat  94080
ttttattatg gacaatttga aatatatgca aaagtcgata agatagtgta ataaattcat  94140
ataaccataa ccctacttca accttactca actcctgaat aatcttgttt tatctaaact  94200
ccctatccac tccccatttt gtatcatttt caggaaagta cttaaaagta tttgatctgg  94260
aaacatttct atgtatatct ctgttaactt tcagaaagcg taaccctgat acccttgtta  94320
tacctaagaa aagttattaa caatttctta ataccaagga gccaacaagt atttacattt  94380
taactctttt acactgtaca ctgcagtatt gcactagagt agggtataaa atacagttaa  94440
```

```
aagtccccct tgaacattaa agttagtttc cctggaggta aacactgcta attattcctc  94500

attaacttct agaatttttt ggcatgtaca aactatatat acatgtatat acaatactag  94560

tctctaactt tatctctttc atttattagg agaacgcaga acactacatc agcctagata  94620

aatctttacc cactgcacca taataaccag gaaattatag ataggcatta cga         94673


<210> SEQ ID NO 8
<211> LENGTH: 11
<212> TYPE: PRT
<213> ORGANISM: Homo sapiens

<400> SEQUENCE: 8

Glu Gly Ile Cys Arg Asn Arg Val Thr Asn Asn
1               5                   10
```